US012521449B2

(12) United States Patent
Thon et al.

(10) Patent No.: US 12,521,449 B2
(45) Date of Patent: Jan. 13, 2026

(54) COMPOSITIONS AND METHODS RELATED TO MEGAKARYOCYTE-DERIVED EXTRACELLULAR VESICLES FOR FANCONI ANEMIA

(71) Applicant: STRM.bio Incorporated, Cambridge, MA (US)

(72) Inventors: Jonathan Thon, Cambridge, MA (US); David Raiser, Cambridge, MA (US); Laura Goldberg, Cambridge, MA (US)

(73) Assignee: STRM.bio Incorporated, Cambridge, MA (US)

( * ) Notice: Subject to any disclaimer, the term of this patent is extended or adjusted under 35 U.S.C. 154(b) by 257 days.

(21) Appl. No.: 18/556,796

(22) PCT Filed: Apr. 26, 2022

(86) PCT No.: PCT/US2022/026412
§ 371 (c)(1),
(2) Date: Oct. 23, 2023

(87) PCT Pub. No.: WO2022/232193
PCT Pub. Date: Nov. 3, 2022

(65) Prior Publication Data
US 2024/0216532 A1 Jul. 4, 2024

Related U.S. Application Data

(60) Provisional application No. 63/209,085, filed on Jun. 10, 2021, provisional application No. 63/179,808, filed on Apr. 26, 2021.

(51) Int. Cl.
*A61K 31/7105* (2006.01)
*A61K 9/50* (2006.01)
(Continued)

(52) U.S. Cl.
CPC ........ *A61K 48/0041* (2013.01); *A61K 9/5068* (2013.01); *A61K 31/7105* (2013.01);
(Continued)

(58) Field of Classification Search
CPC .............. A61K 48/0041; A61K 9/5068; A61K 31/7105; A61K 38/465; A61K 48/005;
(Continued)

(56) References Cited

U.S. PATENT DOCUMENTS 9,085,778 B2 7/2015 Lötvall et al.
9,629,929 B2 4/2017 Lötvall et al.
(Continued)

FOREIGN PATENT DOCUMENTS

WO WO 2015/179301 A1 11/2015
WO WO 2017/044149 A1 3/2017
(Continued)

OTHER PUBLICATIONS

French, et al., "Platelet-derived extracellular vesicles infiltrate and modify the bone marrow during inflammation," Blood Advances, vol. 4, No. 13, pp. 3011-3023, Jul. 14, 2020.
(Continued)

*Primary Examiner* — Ernst V Arnold
(74) *Attorney, Agent, or Firm* — Morgan, Lewis & Bockius LLP

(57) ABSTRACT

Disclosed herein are compositions and methods related to megakaryocyte-derived extracellular vesicles derived from human pluripotent stem cells, where the megakaryocyte-derived extracellular vesicles may be utilized for treating Fanconi anemia (FA).

20 Claims, 27 Drawing Sheets

(51) Int. Cl.

| | |
|---|---|
| ***A61K 38/00*** | (2006.01) |
| ***A61K 38/46*** | (2006.01) |
| ***A61K 48/00*** | (2006.01) |
| ***A61P 7/06*** | (2006.01) |
| ***C12N 15/88*** | (2006.01) |

(52) U.S. Cl.
CPC .......... *A61K 38/465* (2013.01); *A61K 48/005* (2013.01); *A61P 7/06* (2018.01); *C12N 15/88* (2013.01)

(58) Field of Classification Search
CPC .... A61K 9/0019; A61K 9/5089; A61K 38/00; A61P 7/06; C12N 15/88
See application file for complete search history.

(56) References Cited

U.S. PATENT DOCUMENTS

| | | | |
|---|---|---|---|
| 9,856,477 | B2 | 1/2018 | Lötvall et al. |
| 9,889,210 | B2 | 2/2018 | Lötvall et al. |
| 10,195,290 | B1 | 2/2019 | Dooley et al. |
| 10,370,663 | B2 | 8/2019 | Lötvall et al. |
| 10,538,738 | B2 | 1/2020 | Papoutsakis et al. |
| 10,561,740 | B2 | 2/2020 | Dooley et al. |
| 10,695,443 | B2 | 6/2020 | Lötvall et al. |
| 10,723,782 | B2 | 7/2020 | Lewis et al. |
| 11,512,315 | B2 | 11/2022 | Sathyanarayanan et al. |
| 12,090,234 | B2 * | 9/2024 | Thon .................... A61K 9/0014 |
| 2001/0005591 | A1 | 6/2001 | Qasba et al. |
| 2004/0152628 | A9 | 8/2004 | Tandon et al. |
| 2008/0069807 | A1 | 3/2008 | Jy et al. |
| 2008/0213377 | A1 | 9/2008 | Bhatia et al. |
| 2012/0238020 | A1 | 9/2012 | Mitchell et al. |
| 2012/0315338 | A1 | 12/2012 | Li et al. |
| 2012/0321723 | A1 | 12/2012 | Bruno et al. |
| 2017/0058262 | A1 | 3/2017 | Papoutsakis et al. |
| 2018/0055891 | A1 | 3/2018 | Zhao |
| 2019/0202892 | A1 | 7/2019 | Lewis et al. |
| 2019/0203225 | A1 | 7/2019 | Roncero et al. |
| 2020/0115681 | A1 | 4/2020 | Papoutsakis et al. |
| 2021/0275464 | A1 | 9/2021 | Papoutsakis et al. |
| 2022/0143095 | A1 | 5/2022 | Hett et al. |
| 2023/0190815 | A1 | 6/2023 | Thon |
| 2023/0390202 | A1 | 12/2023 | Papoutsakis et al. |
| 2023/0392168 | A1 | 12/2023 | Thon |

FOREIGN PATENT DOCUMENTS

| | | | | |
|---|---|---|---|---|
| WO | WO 2018/049273 | A1 | 3/2018 | |
| WO | WO 2018/165308 | A1 | 9/2018 | |
| WO | WO 2019/136318 | A2 | 7/2019 | |
| WO | WO 2020/006539 | A1 | 1/2020 | |
| WO | WO 2020/018950 | A1 | 1/2020 | |
| WO | WO 2020/028430 | A1 | 2/2020 | |
| WO | WO-2020113059 | A1 * | 6/2020 | ........... A61K 9/5184 |
| WO | WO 2021/138332 | A1 | 7/2021 | |
| WO | WO 2021/173828 | A1 | 9/2021 | |
| WO | WO 2021/231425 | A1 | 11/2021 | |
| WO | WO 2022/081836 | A1 | 4/2022 | |
| WO | WO 2022/087505 | A1 | 4/2022 | |
| WO | WO 2023/070122 | A1 | 4/2023 | |
| WO | WO 2023/086590 | A1 | 5/2023 | |
| WO | WO 2023/086595 | A1 | 5/2023 | |

OTHER PUBLICATIONS

International Search Report & Written Opinion PCT Application No. PCT/US22/26412, dated Jul. 28, 2022, 9 pages.
Arraud, et al., "Extracellular vesicles from blood plasma: determination of their morphology, size, phenotype and concentration," Journal ofThrombosis and Haemostasis, vol. 12, pp. 614-217, 2014.
Berge, et a/., "Pharmaceutical Salts," Pharmaceutical Sciences, vol. 66, No. 1, 19, pp. 1977.
Brisson, et al., "Extracellular vesicles from activated platelets: a semiquantitative cryo-electron microscopy and immuno-gold labeling study," Platelets, vol. 28, No. 3, DD. 263-271, 2017.
Buatois et al Mol Cancer Ther (2018) 17 (8): 1739-1751.
Bulcha, et al., "Viral vector platforms within the gene therapy landscape," Signal Transduction and Targeted TheraDv, vol. 6, No. 53, 24 Daqes, 2021.
Epstein, "Cosmeceutical vehicles," Clinics in Dermatology, vol. 27, pp. 453-460, 2009.
Escobar, et al., "Human megakaryocytic microparticles induce de novo platelet biogenesis in a wild-type murine model," Blood Advances, vol. 4, No. 5, pp. 804-814, 2020.
Flaumenhaft, et al., "Megakaryocyte-derived microparticles: direct visualization and distinction from platelet-derived microparticles," Blood, vol. 113, No. 5, DD. 1112-1121, 2009.
Gilligan, Cells 2020, 9, 224; doi:10.3390/cells9010224.
Jaiswal, Siddhartha, et al., "CD47 is upregulated on circulating hematopoietic stem cells and leukemia cells to avoid phagocytosis.", Cell 138.2 (2009): 271-285. (Year: 2009).
Jiang, et al., "How do megakaryocytic microparticles target and deliver cargo to alter the fate of hematopoietic stem cells?" J Control Release, vol. 247, DD. 1-18, 2017.
Jiang, et al., "Shear enhances thrombopoiesis and formation of microparticles that induce megakaryocytic differentiation of stem cells," Blood, vol. 124, No. 13, pp. 2094-2103, 2014.
Kamerkar, Nature. Jun. 22, 2017; 546(7659): 498-503. doi:10.1038/nature22341.
Kanada, et al., "Diferential fates of biomolecules delivered to target cells via extracellular vesicles," PNAS, vol. 112, No. 12, pp. E1433-E1442, Feb. 23, 2015.
Kao, et al., "Engineering human megakaryocytic microparticles for targeted delivery of nucleic acids to hematopoietic stem and progenitor cells," Sci. Adv., vol. 4, 11 paqes. 2018.
Kao, et al., "Extracellular vesicles: exosomes, microparticles, their parts, and their targets to enable their biomanufacturing and clinical applications," Current Opinion in Biotechnology, vol. 60, pp. 89-98, 2019.
Kotmakçi, J Pharm Pharm Sci 18(3) 396-413, 2015.
Nicoletti, E. et al. Ann Hematol 99, 913-924 (2020).
Pham, et al. J. Extracellular Vesc. 10(4): e12057 (Feb. 2021).
Rio, P. et al. Blood 130, 1535-1542 (2017).
Rio, P. et al. Nat Med 25, 1396-1401 (2019).
Román-Rodríguez, F. J. et al. Cell Stem Cell 25, 607-621.e7 (2019).
Schlinker, Biotechnol Bioeng. Apr. 2015; 112(4): 788-800.
Stahl, et al., "Handbook of Pharmaceutical Salts: Properties, Selection, and Use," Journal of Medicinal Chemistry, vol. 46, No. 7, pp. 1277-1278, 2003.
Zeltner, et al., "Near-perfect infectivity of wild-type AAV as benchmark for infectivity of recombinant AAV vectors," Gene Ther., vol. 17, No. 7, DD. 872-879, 2010.
Zhou, et al., "A pneumonia outbreak associated with a new coronavirus of probable bat origin," Nature, vol. 579, 20 pages, 2020.

* cited by examiner

Negative control

CD41/CD61+MkEVs

Unfiltered MkEV Product

650nm Filtered MkEV Product

Key:
WBM: Whole bone marrow
Lin+ cells: Lineage + cells
Lin- cells: Lineage negative cells
LSK cells: lineage negative/c-Kit+/Sca-1+

Key
Mock: electroporated unloaded MkEVs
DP-EVs: pDNA loaded MkEV
0.1X: 1/10th pDNA loading dose
1X: baseline pDNA loading

COMPOSITIONS AND METHODS RELATED TO MEGAKARYOCYTE-DERIVED EXTRACELLULAR VESICLES FOR FANCONI ANEMIA

CROSS-REFERENCE TO RELATED APPLICATIONS

This application is a 35 U.S.C. § 371 national phase application of International Patent Application No. PCT/US2022/26412, filed Apr. 26, 2022, which claims the benefit of priority to U.S. Provisional Patent Application Nos. 63/179,808, filed Apr. 26, 2021, and 63/209,085, filed Jun. 10, 2021, all of which are incorporated by reference herein in their entireties.

FIELD

The present disclosure relates to compositions and methods related to megakaryocyte-derived extracellular vesicles derived from human pluripotent stem cells for the treatment of Fanconi Anemia (FA).

BACKGROUND

Treatment using nanodelivery vehicles can have several advantages, including reducing renal clearance, improving site-specific delivery, simultaneous delivery of multiple therapeutic agents, protection from enzymatic degradation, immunoevasion, sequential multistage release, stimuli-responsive activation, and theranostic capabilities, among others. Nevertheless, the majority of these features are not yet in clinical use, partially due to complex and costly manufacturing required to achieve multi-functionality. Liposomes can trigger adverse effects in a patient, including immune reactions and cytotoxicity, in addition to target non-specificity and inefficient unloading of therapeutic agents, because liposomes are foreign, synthetic entities, with limited cell or tissue targeting machinery. Adenovirus, retrovirus, AAV, and lentivirus vectors are currently the most popular viral vectors for gene therapy today; however, these modalities suffer from targeting, scalability of manufacture, immunogenicity, and safety concerns.

Fanconi anemia (FA) is an autosomal recessive disorder characterized by congenital abnormalities, bone marrow failure, and a predisposition to malignancies, including myelodysplastic syndrome and acute myelogenous leukemia. Most patients experience bone marrow failure at a median age of five years. Progressive pancytopenia and congenital malformations, including short stature, radial aplasia, urinary tract abnormalities, hyperpigmentation, and developmental delay are common symptoms. Fanconi Anemia is associated with a predisposition to cancer, particularly acute myeloid leukemia and an increased risk of developing solid tumors.

The FA gene products play an important role in protecting the integrity of the human genome; mutations in any of the FA genes lead to genomic instability due to failure to repair DNA damage. Over the last decade, the role for Fanconi Anemia gene products in DNA repair has been established. However, the source and chemical agents that cause excessive genomic instability leading to the phenotype of developmental abnormality, BMF, and predisposition malignancy in FA patients had been elusive, and treatments for FA are mainly focused on symptoms, not cures.

Accordingly, there is a need for delivery vehicles that can be generated cost-effectively at scale and that eliminate or reduce adverse effects when administered to a patient, and that can also provide novel treatments for FA capable of repairing DNA damage and improving chromosomal stability.

SUMMARY

Disclosed herein are compositions and methods related to megakaryocyte-derived extracellular vesicles. Specifically, inter alia, the present megakaryocyte-derived extracellular may be utilized for drug delivery and treatment of Fanconi Anemia (FA). The methods disclosed herein may be in vivo or ex vivo and may be used in for example, gene therapy, gene replacement therapy and gene-editing.

In one aspect, the present disclosure relates to a method for modifying a cell. The disclosed method comprises: (a) contacting the cell with a composition comprising a plurality of substantially purified megakaryocyte-derived extracellular vesicles (MkEVs) comprising a lipid bilayer membrane surrounding a lumen, wherein: the MkEVs lumen comprises a cargo comprising an agent suitable for modifying the cell; and/or, a cargo comprising an agent suitable for modifying the cell is associated with the surface of the MkEVs; and the lipid bilayer membrane comprises one or more proteins associated with or embedded within, and (b) modifying the cell to provide a functional Fanconi anemia (FA) related gene and/or to repair a mutated functional FA-related gene therein.

In another aspect, the present invention relates to a method for treating Fanconi anemia (FA), the method comprising (a) obtaining a plurality of substantially purified megakaryocyte-derived extracellular vesicles; (b) incubating the plurality of substantially purified megakaryocyte-derived extracellular vesicles with a therapeutic agent to allow the therapeutic agent to populate the lumen of the megakaryocyte-derived extracellular vesicle and/or associate with the surface of the megakaryocyte-derived extracellular vesicle and yield a deliverable therapeutic agent, wherein the therapeutic agent is capable of treating FA; and (c) administering the deliverable therapeutic agent to a patient or contacting the deliverable therapeutic agent with a biological cell in vitro and administering the contacted biological cell to a patient, wherein the megakaryocyte-derived extracellular vesicles are substantially purified and comprise a lipid bilayer membrane surrounding a lumen, the megakaryocyte-derived extracellular vesicle lumen comprises the therapeutic agent and/or is associated with the surface of the megakaryocyte-derived extracellular vesicle; and the lipid bilayer membrane comprises one or more proteins associated with or embedded within.

In another aspect, the present invention relates to a method for treating Fanconi anemia (FA), the method comprising (a) obtaining a plurality of substantially purified megakaryocyte-derived extracellular vesicles; the megakaryocyte-derived extracellular vesicles comprising a lipid bilayer membrane surrounding a lumen, wherein: the lipid bilayer membrane comprises one or more proteins associated with or embedded within; (b) incubating the plurality of substantially purified megakaryocyte-derived extracellular vesicles with a therapeutic agent to allow the therapeutic agent to populate the lumen of the megakaryocyte-derived extracellular vesicle and/or associate with the surface of the megakaryocyte-derived extracellular vesicle and yield a deliverable therapeutic agent, wherein the therapeutic agent is capable of increasing or restoring the FA-related gene expression and/or levels and/or function of one or more FA-related proteins; and, (c) administering the deliverable therapeutic agent to a patient or contacting the deliverable therapeutic agent with a biological cell in vitro and administering the contacted biological cell to a patient, thereby restoring or increasing FA-related gene expression in the patient to reach a normal level of a patient not afflicted with FA.

BRIEF DESCRIPTION OF THE DRAWINGS

FIGS. 2A-2B are representative graphs demonstrating the flow cytometry gating strategy. FIG. 2C is a representative graph demonstrating the marker profile of CD41+ MKEVs of the disclosure, CD41+ PFP MkEVs, and CD41+ PLT EVs. MKEVs of the disclosure have different surface marker phenotypes compared to naturally occurring MkEVs and platelet-derived EVs. Differential expression of surface markers co-expressed on CD41+ STRM MkEVs (black bars) when compared to CD41+ naturally occurring platelet free plasma (PFP) MkEVs (hashed bars) and CD41+ platelet-derived EVs (dotted bars). For MKEVs of the disclosure and PFP MkEVs, bars represent average percent±standard deviation, n=2 biologic replicates. Fold change is relative to PFP EVs. FIG. 2D is a representative graph demonstrating the fold change in marker expression between MkEVs of the disclosure and PFP MkEVs. For CD32a, GPVI, and CD18, fold change calculations were made by changing values of 0 to 0.01. FIG. 2E is a representative graph demonstrating the fold change in marker expression between MkEVs of the disclosure and PLT EVs. For CD32a, fold change calculations were made by changing values of 0 to 0.01. The data shows that MkEVs of the disclosure exhibit different expression of surface markers compared to PFP MkEVs and PLT EVs and establish a marker profile of the present MkEVs relative to PFP MkEVs and PLT EVs. FIG. 2F is a representative graph demonstrating the minimal presence of DRAQ5 positive events showing the lack of cellular contamination.

FIG. 3A is a cryo-EM image of MkEVs of the disclosure with immunogold labeling of CD41. FIG. 3B is a cryo-EM image of MkEVs of the disclosure with immunogold labeling of phosphatidylserine. Measuring of MkEVs in cryo-EM images showed a range of MkEV sizes between 100-500 nm, averaging ~250 nm in diameter.

FIG. 5A shows unfiltered MkEV product. FIG. 5B shows 650-nm filtered MkEV product. Successful clearance of large aggregate material (observed by EM in frozen MkEV samples) was demonstrated by post-harvest filtration with 650 nm size exclusion filter. Images are from flow cytometry experiments.

FIG. 10B shows fluorescent signal detected by IVIS in femurs dissected from mice. N=5 mice/group. Fluorescence in each homogenized tissue, was assayed by plate reader and normalized by tissue weight (FIG. 10C). FIGS. 10D and 10E show graphs of experimental data of bone marrow cells stained using antibodies against CD45, Lineage markers, CD150, CD201, and CD48 and analyzed by flow cytometry to determine the % of hematopoietic (CD45+ cells; left panel, FIG. 10D) and % of very primitive long-term hematopoietic stem cells (CD45+/Lin−/CD150+/CD201+/CD48− cells; right panel, FIG. 10E) that were positive for MkEVs. MkEVs preferentially target the hematopoietic cells within the bone marrow (FIG. 10D) and within that compartment, are targeting the very rare (<0.03% of marrow cells) long-term hematopoietic stem cells (FIG. 10E). There were no changes in the peripheral white blood cell count (FIG. 10F), hemoglobin (FIG. 10G), platelet count (FIG. 10H), WBC differential (FIG. 10I), or % of CD45+ and CD45− cells (FIG. 10J), or % of the long-term hematopoietic stem cells in the marrow (FIG. 10K) 16 hours following MkEV injection indicating lack of hematopoietic toxicity following in vivo injection.

FIG. 11A shows a graph of experimental data demonstrating a 9.8 kb pDNA encoding wildtype FANCA electroporated (EP) into MkEVs Following electroporation, all samples were treated with DNase to remove any noninternalized pDNA cargo prior to DNA extraction. DNA was then extracted and qPCR was performed. Loaded pDNA was quantified (ng) based on a standard curve run in parallel, and number of pDNA copies/MkEV was calculated. FIG. 11B. shows a graph of experimental data demonstrating Cas9 loading into MkEVs. MkEVs were electroporated with Cas9, treated with proteinase K to remove any un-internalized cargo (free cargo and vesicle surface-associated cargo), or with filtration to remove any free cargo, and then analyzed by western blotting for quantification of Cas9. Controls included MkEVs plus Cas9 without electroporation±Proteinase K±filtration. Cas9 was present in electroporated MkEVs, but not in control un-electroporated MkEVs, following filtration indicating the successful vesicle association and/or internalization of protein cargo. Cas9 was present in electroporated MkEVs, but not in control un-electroporated MkEVs following proteinase K digestion indicating successful internalization and protection of loaded protein cargo following electroporation.

FIG. 12A shows a gel demonstrating that cells cocultured in duplicate with DP-EVs showed strong expression of human FANCA from MkEV-mediated delivery of the pDNA. In contrast, the mock controls (cells co-cultured with MkEVs processed in parallel but without a pDNA cargo loaded) showed no human FANCA expression. FIG. 12B shows a graph of densitometry readings indicating an 18.5× increase in FANCA mRNA expression in the cells treated with DP-EVs compared to mock treated cells.

FIG. 13A shows a gel demonstrating that cells cocultured with DP-EVs showed strong expression on human FANCA from MkEV-mediated delivery of the pDNA. In contrast, the mock control (cells co-cultured with MkEVs processed in parallel but without a pDNA cargo loaded) showed no FANCA expression. FIG. 13B shows a graph of densitometry readings indicating a 1.3 and 4.4× increase in FANCA mRNA expression in the cells treated with low dose and high dose DP-EVs, respectively, when compared to mock-treated cells.

FIG. 14A shows a gel demonstrating that cells cocultured with DP-EVs showed strong expression of human FANCA from MkEV-mediated delivery of the pDNA. In contrast, the mock controls (cells co-cultured with MkEVs processed in parallel but without a pDNA cargo loaded) showed no FANCA expression. FIG. 14B shows a graph of densitometry readings indicating an 60× increase in FANCA mRNA expression in the cells treated with DP-EVs compared to mock treated cells.

Figure 1A:
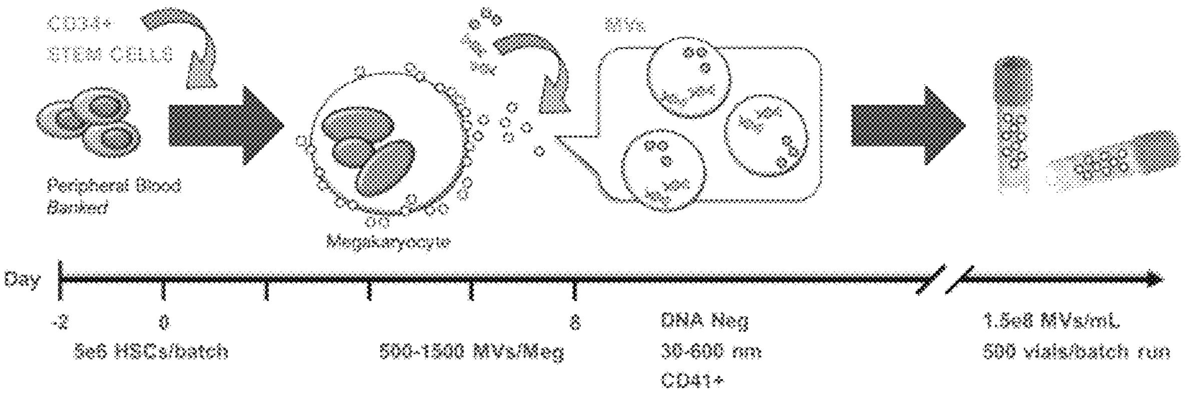
FIG. 1A is a schematic showing the differentiation steps of megakaryocyte-derived extracellular vesicles ("MkEVs" or "MVs"), with the duration of each stage, timing of harvest, and associated yields indicated.

were co-cultured with FANCA-deficient human cells (e.g., FA patient derived lymphoblastic cells that were immortalized). Cells alone and cells treated with MkEVs processed in parallel but without RNP cargo (Mock) served as controls. Following 24 hours in co-culture, 100% of cells co-cultured with DP-EV were GFP-positive and no changes in viability when compared to untouched cells was observed, indicating no toxicity (data not shown). The cells cocultured with DP-EVs showed an increased number of cells after 14 days in culture when compared to the cells alone and mock controls. These data indicate successful restoration of FANCA expression in the DP-EV treated cells leading to their proliferative advantage, a functional benefit of successful restoration of FANCA expression.

DETAILED DESCRIPTION

The present disclosure is based, in part on the discovery of compositions and methods useful for the treatment of Fanconi Anemia (FA). In embodiments, the treatment of Fanconi Anemia (FA) also includes the treatment of symptoms related to FA and/or the likelihood of a patient developing one or more diseases and disorders associated with FA. In embodiments, the compositions comprise substantially purified megakaryocyte-derived extracellular vesicles that are characterized by particular sets of physical characteristics, such as biomarker makeup (e.g. the presence, absence, or amount of a biomarker) and size, and can carry cargo in the lumen for use in delivering agents, such as therapeutic agents, useful for treating Fanconi Anemia (FA). In embodiments, the megakaryocyte-derived extracellular vesicles of the disclosure are distinct from the naturally occurring products, which are collected from whole blood (Platelet Free Plasma) or derived from activated platelets (Platelet EVs). Accordingly, in aspects, the present disclosure provides compositions and methods useful for the treatment Fanconi Anemia (FA), using megakaryocyte-derived extracellular vesicles that are consistently produced, with desirable properties, and carry specific cargo-making their therapeutic use for the treatment of Fanconi Anemia (FA) more likely to be successful.

Methods of Modifying a Cell Using Megakaryocyte-Derived Extracellular Vesicles

In one aspect, the present disclosure relates to a method for modifying a cell the method comprising: (a) contacting the cell with a composition comprising a plurality of substantially purified megakaryocyte-derived extracellular vesicles (MkEVs) comprising a lipid bilayer membrane surrounding a lumen, wherein: the MkEVs lumen comprises a cargo comprising an agent suitable for modifying the cell; and/or, a cargo comprising an agent suitable for modifying the cell is associated with the surface of the MkEVs; and the lipid bilayer membrane comprises one or more proteins associated with or embedded within, and (b) modifying the cell to provide a functional Fanconi anemia (FA) related gene and/or to repair a mutated functional FA-related gene therein. In embodiments, the megakaryocyte-derived extracellular vesicles comprise a cargo in the lumen and is associated with the surface of the megakaryocyte-derived extracellular vesicles.

In one aspect, the present disclosure relates to a method for modifying a cell the method comprising: (a) contacting the cell with a composition comprising a plurality of substantially purified megakaryocyte-derived extracellular vesicles (MkEVs) comprising a lipid bilayer membrane surrounding a lumen, wherein: the MkEVs comprises a cargo comprising an agent suitable for modifying the cell; and the lipid bilayer membrane comprises one or more proteins associated with or embedded within, and (b) modifying the cell to provide a functional Fanconi anemia (FA) related gene and/or to repair a mutated functional FA-related gene therein. In embodiments, the megakaryocyte-derived extracellular vesicles comprise a cargo in the lumen or a cargo associated with the surface of the megakaryocyte-derived extracellular vesicles. In embodiments, the megakaryocyte-derived extracellular vesicles comprise a cargo in the lumen and is associated with the surface of the megakaryocyte-derived extracellular vesicles.

In embodiments, the disclosed methods for modifying a cell are methods for modifying the gene expression of the cell.

In embodiments, the cargo and/or the agent suitable for modifying the cell comprise(s) one or more therapeutic agents.

In embodiments, the therapeutic agent comprises a FA-related gene or a fragment thereof comprising FANCA, FANCB, FANCC, FANCD1 (BRCA2), FANCD2, FANCE, FANCF, FANCG, FANCI, FANCJ (BRIP1), FANCL, FANCM, FANCN (PALB2), FANCO (RAD51C), FANCP (SLX4), FANCQ (ERCC4), FANCR (Rad51), FANGS (BRCA1), FANCT (UBE2T), FANCU (XRCC2), FANCV (REV7) and FANCW (RFWD3) or a fragment thereof.

In embodiments, the therapeutic agent increases or restores the FA-related gene expression and/or levels and/or function of one or more FA-related proteins.

In embodiments, the FA-related proteins comprise FANCA, FANCB, FANCC, FANCD1 (BRCA2), FANCD2, FANCE, FANCF, FANCG, FANCI, FANCJ (BRIP1), FANCL, FANCM, FANCN (PALB2), FANCO (RAD51C), FANCP (SLX4), FANCQ (ERCC4), FANCR (Rad51), FANGS (BRCA1), FANCT (UBE2T), FANCU (XRCC2), FANCV (REV7) and FANCW (RFWD3).

In embodiments, the therapeutic agent is a small molecule therapeutic agent, or a biologic therapeutic agent. In embodiments, the biologic therapeutic agent is used for gene therapy. In embodiments, the biologic therapeutic agent encodes a functional protein or a recombinant protein. In embodiments, the functional protein or the recombinant protein comprises a wild-type protein, a fusion protein, a cytokine, an antigen, and a peptide, an antibody or an antibody fragment. In embodiments, the therapeutic agent is a nucleic acid therapeutic agent. In embodiments, the nucleic acid therapeutic agent expresses a wild-type functional FA gene, and/or comprises a nucleic acid encoding a functional FA-related gene, or a protein product thereof, or a nucleic acid encoding a gene-editing protein capable of creating a functional FA-related gene, or a protein product thereof, or a ribonucleoprotein gene-editing complex capable of creating a functional FA-related gene or a protein product thereof. In embodiments, the nucleic acid therapeutic agent is selected from one or more non-autologous and/or recombinant nucleic acid constructs selected from mRNA, tRNA, rRNA, siRNA, microRNA, regulating RNA, non-coding and coding RNA, linear DNA, plasmid DNA, or DNA fragments.

In embodiments, the one or more non-autologous and/or recombinant nucleic acid constructs are incorporated into a vector.

In embodiments, a vector is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. In embodiments, a vector includes an autonomously replicating plasmid or a virus. In embodiments, a vector includes non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

For instance, the expression of natural or synthetic nucleic acids encoding FA-related genes can be achieved by, but is not limited to, operably linking a nucleic acid encoding the FA-related genes or portions thereof to a promoter, and incorporating the construct into an expression vector. In embodiments, a vector used in this invention is suitable for replication and, optionally, integration in eukaryotic cells. Typical vectors contain transcription and translation terminators, initiation sequences, and promoters useful for regulation of the expression of the desired nucleic acid sequence.

In embodiments, a vector used in the present disclosure may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In embodiments, the present disclosure provides a gene therapy vector.

In embodiments, the nucleic acids of the present disclosure provide a functional Fanconi anemia (FA) related gene or fragments thereof which can be cloned into a number of types of vectors. For example, the nucleic acids can be cloned into a vector including, but not limited to a plasmid, a phagemid, a phage derivative, an animal virus, and a cosmid. Vectors of particular interest include expression vectors, replication vectors, probe generation vectors, and sequencing vectors. Further, the vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

In embodiments, operably linked sequences include both expression control sequences that are contiguous with the gene of interest and expression control sequences that act in trans or at a distance to control the gene of interest. In embodiments, expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1$\alpha$ (EF-1$\alpha$). However, other constitutive promoter sequences may also be used, including, but not limited to, the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the present invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Enhancer sequences found on a vector also regulates expression of the gene contained therein. Typically, enhancers are bound with protein factors to enhance the transcription of a gene. Enhancers may be located upstream or downstream of the gene it regulates. Enhancers may also be tissue-specific to enhance transcription in a specific cell or tissue type. In one embodiment, the vector of the present invention comprises one or more enhancers to boost transcription of the gene present within the vector.

In embodiments, the vector is an expression vector comprising an expression control sequence operatively linked to a nucleotide sequence. In embodiments, the vector is a plasmid, a phagemid, a phage derivative, a cosmid, or a viral vector. In embodiments, the viral vector comprises an adenovirus vector, an adeno-associated virus vector, a poxvirus vector, a retrovirus vector, a lentivirus vector, a sendai virus vector, herpes simplex virus vector, a cytomegalovirus vector, or chimeric viral vectors.

In embodiments, the therapeutic agent is any nucleic acid delivery system known in the art useful for vaccination. In one embodiment, the nucleic acid delivery system is a vaccine vector, a DNA plasmid, or an mRNA vaccine. In embodiments, the therapeutic agent is a vaccine and/or an immunogenic antigen.

In embodiments, the nucleic acid therapeutic agent encodes a gene-editing protein, and/or associated elements for gene-editing functionality, gene-editing protein is selected from a zinc finger (ZF), transcription activator-like effector (TALE), meganuclease, and clustered regularly interspaced short palindromic repeat (CRISPR)-associated protein. In embodiments, CRISPR-associated protein is selected from Cas9, xCas9, Cas12a (Cpf1), Cas13a, Cas14, CasX, CasY, a Class 1 Cas protein, a Class 2 Cas protein, MAD7, and gRNA complexes thereof.

Methods of Treatment Using Megakaryocyte-Derived Extracellular Vesicles

In embodiments, the present disclosure relates to a method for treating Fanconi Anemia (FA) with the present megakaryocyte-derived extracellular vesicles. In embodiments, the present disclosure relates to a method for treating FA by delivering a therapeutic cargo, e.g. a gene therapy cargo, in, or associated with, the present megakaryocyte-derived extracellular vesicles (MkEVs).

In one aspect, the present invention relates to a method for treating Fanconi anemia (FA). The disclosed method comprises (a) obtaining a plurality of substantially purified megakaryocyte-derived extracellular vesicles; (b) incubating the plurality of substantially purified megakaryocyte-derived extracellular vesicles with a therapeutic agent to allow the therapeutic agent to populate the lumen of the megakaryocyte-derived extracellular vesicle and/or associate with the surface of the megakaryocyte-derived extracellular vesicle and yield a deliverable therapeutic agent, wherein the therapeutic agent is capable of treating FA; and (c) administering the deliverable therapeutic agent to a patient or contacting the deliverable therapeutic agent with a biological cell in vitro and administering the contacted biological cell to a patient, wherein the megakaryocyte-derived extracellular vesicles are substantially purified and comprise a lipid bilayer membrane surrounding a lumen, the megakaryocyte-derived extracellular vesicle lumen comprises the therapeutic agent and/or is associated with the surface of the megakaryocyte-derived extracellular vesicle; and the lipid bilayer membrane comprises one or more proteins associated with or embedded within.

In another aspect, the present invention relates to a method for treating Fanconi anemia (FA). The disclosed method comprises (a) obtaining a plurality of substantially purified megakaryocyte-derived extracellular vesicles; the megakaryocyte-derived extracellular vesicles comprising a lipid bilayer membrane surrounding a lumen, wherein: the lipid bilayer membrane comprises one or more proteins associated with or embedded within; (b) incubating the plurality of substantially purified megakaryocyte-derived extracellular vesicles with a therapeutic agent to allow the therapeutic agent to populate the lumen of the megakaryocyte-derived extracellular vesicle and/or associate with the surface of the megakaryocyte-derived extracellular vesicle and yield a deliverable therapeutic agent, wherein the therapeutic agent is capable of increasing or restoring the FA-related gene expression and/or levels and/or function of one or more FA-related proteins; and, (c) administering the deliverable therapeutic agent to a patient or contacting the deliverable therapeutic agent with a biological cell in vitro and administering the contacted biological cell to a patient, thereby restoring or increasing FA-related gene expression in the patient to reach a normal level of a patient not afflicted with FA.

In embodiments, treatment includes therapeutic treatment as well as prophylactic, or suppressive measures for the disease or disorder. In embodiments, the term "treatment" and associated terms such as "treat" and "treating" mean the reduction of the progression, severity and/or duration of a disease condition or at least one symptom thereof. In embodiments, treatment refers to any regimen that can benefit a subject. The treatment may be in respect of an existing condition or may be prophylactic (preventative treatment). Treatment may include curative, alleviative or prophylactic effects. In embodiments, "therapeutic" and "prophylactic" treatments are to be considered in their broadest context. In embodiments, the term "therapeutic" does not necessarily imply that a subject is treated until total recovery. In embodiments, the term "prophylactic" does not necessarily mean that the subject will not eventually contract a disease condition. In embodiments, the term treatment includes the administration of an agent prior to or following the onset of a disease or disorder thereby preventing or removing all signs of the disease or disorder. In embodiments, administration of the agent after clinical manifestation of the disease to combat the symptoms of the disease comprises "treatment" of the disease.

In embodiments, treating may include suppressing, inhibiting, preventing, treating, delaying the onset of or a combination thereof. Treating refers inter alia to increasing time to sustained progression, expediting remission, inducing remission, augmenting remission, speeding recovery, increasing efficacy of or decreasing resistance to alternative therapeutics, or a combination thereof. In embodiments, "suppressing" or "inhibiting", refers inter alia to delaying the onset of symptoms, preventing relapse to a disease, decreasing the number or frequency of relapse episodes, increasing latency between symptomatic episodes, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In embodiments, the present disclosure relates to a method for treating FA, comprising administering an effective amount of a composition disclosed herein, wherein the composition comprises megakaryocyte-derived extracellular vesicles, which comprise cargo. In embodiments, the megakaryocyte-derived extracellular vesicles comprise a lipid bilayer membrane surrounding a lumen and derived from a human pluripotent stem cell, wherein the megakaryocyte-derived extracellular vesicle lumen comprises the cargo. In embodiments, in addition to or as an alternative to the cargo located in the lumen of the megakaryocyte-derived extracellular vesicle, the cargo is associated with the surface of the vesicle. In embodiments, the cargo is selected from one or more of a RNA, DNA, protein, carbohydrate, lipid, biomolecule, and small molecule. In embodiments, the cargo is one or more therapeutic agents.

In embodiments, the present disclosure relates to a method for treating FA, comprising administering an effective amount of a composition described herein, wherein the composition comprises megakaryocyte-derived extracellular vesicles which comprise a nucleic acid encoding a FA-related gene, or a protein product thereof, or a nucleic acid encoding a gene-editing protein capable of creating a functional FA-related gene, or a protein product thereof, capable of creating a functional FA-related gene or a protein product thereof.

In embodiments, the present disclosure relates to a method for treating FA, comprising administering an effective amount of a composition comprising a cell which is contacted with a composition described herein in vitro, wherein the composition comprises megakaryocyte-derived extracellular vesicles which comprise a nucleic acid encoding a functional FA-related gene, or a protein product thereof, or a nucleic acid encoding a gene-editing protein capable of creating a functional FA-related gene, or a protein product thereof, or a ribonucleoprotein gene-editing complex capable of creating a functional FA-related gene or a protein product thereof.

In embodiments, the present methods are performed in vivo or ex vivo.

In embodiments, the present disclosure relates to a method for treating FA, comprising administering an effective amount of a composition comprising a cell which is contacted with a composition described herein ex vivo, wherein the composition comprises megakaryocyte-derived extracellular vesicles which comprise a nucleic acid encoding a functional FA-related gene, or a protein product thereof, or a nucleic acid encoding a gene-editing protein capable of creating a functional FA-related gene, or a protein product thereof, or a ribonucleoprotein gene-editing complex capable of creating a functional FA-related gene or a protein product thereof.

In embodiments, the present disclosure relates to a method for treating FA, comprising administering an effective amount of a composition comprising a cell which is contacted with a composition described herein in vivo, wherein the composition comprises megakaryocyte-derived extracellular vesicles which comprise a nucleic acid encoding a functional FA-related gene, or a protein product thereof, or a nucleic acid encoding a gene-editing protein capable of creating a functional FA-related gene, or a protein product thereof, or a ribonucleoprotein gene-editing complex capable of creating a functional FA-related gene or a protein product thereof.

In embodiments, the compositions are administered by injection into the subject. In embodiments, the compositions are administered by injection intravenously into the subject.

In embodiments, the method for treating Fanconi anemia (FA) allows restoring or increasing FA-related gene expression in the patient to reach a normal level of a patient not afflicted with FA.

In embodiments, the level of FA-related gene expression in the patient is compared to a reference (i.e. the control) level of expression of FA-related gene expression measured in a patient not afflicted with FA and/or not showing any FA-related symptoms. For example, the patient not afflicted with FA may include a healthy subject. Preferably, the healthy subject is a subject of similar age, gender, race as the patient treated for FA based on the presently disclosed methods.

In embodiments, the level of FA-related gene expression in the patient is compared to a reference (i.e. the control) level of expression of FA-related gene expression based on the average or the mean level of FA-related gene expression in a normal population where the subjects are not afflicted with FA and/or not showing any FA-related symptoms. In embodiments, the average or the mean level of FA-related gene expression is based on a value known in the art.

Examples of methods to assessing level of gene expression are known in the art, and include, but are not limited to, microarrays, PCR, RT-PCR, quantitative PCR, or Next Generations Sequencing technologies.

In embodiments, the method for treating Fanconi anemia (FA) allows restoring or increasing FA-related gene expression in the patient to reach 5% or about 5% of the normal level of a patient not afflicted with FA; 10% or about 10% of the normal level of a patient not afflicted with FA; 15% or about 15% of the normal level of a patient not afflicted with FA; 20% or about 20% of the normal level of a patient not afflicted with FA; 25% or about 25% of the normal level of a patient not afflicted with FA; 30% or about 30% of the normal level of a patient not afflicted with FA; 35% or about 35% of the normal level of a patient not afflicted with FA; 40% or about 40% of the normal level of a patient not afflicted with FA; 45% or about 45% of the normal level of a patient not afflicted with FA; 50% or about 50% of the normal level of a patient not afflicted with FA; 55% or about 55% of the normal level of a patient not afflicted with FA; 60% or about 60% of normal level of a patient not afflicted with FA; 65% or about 65% of normal level of a patient not afflicted with FA; 70% or about 70% of normal level of a patient not afflicted with FA; 75% or about 75% of normal level of a patient not afflicted with FA; 80% or about 80% of normal level of a patient not afflicted with FA; 85% or about 85% of normal level of a patient not afflicted with FA; 90% or about 90% of normal level of a patient not afflicted with FA; 95% or about 95% of normal level of a patient not afflicted with FA; or 100% or about 100% of the normal level of a patient not afflicted with FA.

In embodiments, the cargo and/or the agent suitable for modifying the cell comprise(s) one or more therapeutic agents.

In embodiments, the therapeutic agent comprises a FA-related gene or a fragment thereof comprising FANCA, FANCB, FANCC, FANCD1 (BRCA2), FANCD2, FANCE, FANCF, FANCG, FANCI, FANCJ (BRIP1), FANCL, FANCM, FANCN (PALB2), FANCO (RAD51C), FANCP (SLX4), FANCQ (ERCC4), FANCR (Rad51), FANGS (BRCA1), FANCT (UBE2T), FANCU (XRCC2), FANCV (REV7) and FANCW (RFWD3) or a fragment thereof.

In embodiments, the therapeutic agent increases or restores the FA-related gene expression and/or levels and/or function of one or more FA-related proteins.

In embodiments, the FA-related proteins comprise FANCA, FANCB, FANCC, FANCD1 (BRCA2), FANCD2, FANCE, FANCF, FANCG, FANCI, FANCJ (BRIP1), FANCL, FANCM, FANCN (PALB2), FANCO (RAD51C), FANCP (SLX4), FANCQ (ERCC4), FANCR (Rad51), FANGS (BRCA1), FANCT (UBE2T), FANCU (XRCC2), FANCV (REV7) and FANCW (RFWD3).

Any FA-related gene is contemplated by the disclosure. Non-limiting examples of FA-related genes include FANCA, FANCB, FANCC, FANCD1 (BRCA2), FANCD2, FANCE, FANCF, FANCG, FANCI, FANCJ (BRIP1), FANCL, FANCM, FANCN (PALB2), FANCO (RAD51C), FANCP (SLX4), FANCQ (ERCC4), FANCR (Rad51), FANGS (BRCA1), FANCT (UBE2T), FANCU (XRCC2), FANCV (REV7) and FANCW (RFWD3).

In embodiments, the present treatments of FA provide for a gene therapy cargo, in or associated with the present megakaryocyte-derived extracellular vesicles (MkEVs), the gene therapy cargo comprising a nucleic acid encoding a wild type, unmutated and/or functional FA-related gene, selected from FANCA, FANCB, FANCC, FANCD1 (BRCA2), FANCD2, FANCE, FANCF, FANCG, FANCI, FANCJ (BRIP1), FANCL, FANCM, FANCN (PALB2), FANCO (RAD51C), FANCP (SLX4), FANCQ (ERCC4), FANCR (Rad51), FANGS (BRCA1), FANCT (UBE2T), FANCU (XRCC2), FANCV (REV7) and FANCW (RFWD3). In embodiments, the gene therapy cargo is DNA or RNA.

In embodiments, the present treatments of FA provide for a gene therapy cargo, in or associated with the present megakaryocyte-derived extracellular vesicles (MkEVs), the gene therapy cargo comprising a nucleic acid encoding a wild type, unmutated and/or functional FA-related gene, selected from FANCA, FANCB, FANCC, FANCE, FANCF, FANCG, FANCL, FANCM, FANCD1, FANCJ, FANCN and FANCP. In embodiments, the gene therapy cargo is DNA or RNA.

In embodiments, the present treatments of FA provide for a gene therapy cargo, in or associated with the present megakaryocyte-derived extracellular vesicles (MkEVs), the gene therapy cargo comprising a gene-editing protein and/or associated elements for gene-editing functionality directed against a FA-related. In embodiments, the present treatments of FA provide for a gene therapy cargo, in or associated with the present megakaryocyte-derived extracellular vesicles (MkEVs), the gene therapy cargo comprising a gene-editing protein and/or associated elements for gene-editing functionality directed against a FA-related gene, selected from FANCA, FANCB, FANCC, FANCD1 (BRCA2), FANCD2, FANCE, FANCF, FANCG, FANCI, FANCJ (BRIP1), FANCL, FANCM, FANCN (PALB2), FANCO (RAD51C), FANCP (SLX4), FANCQ (ERCC4), FANCR (Rad51), FANGS (BRCA1), FANCT (UBE2T), FANCU (XRCC2), FANCV (REV7) and FANCW (RFWD3). In embodiments, the gene-editing protein provides a corrective edit that allows for a functional FA protein.

In embodiments, the present treatments of FA provide for a gene therapy cargo, in or associated with the present megakaryocyte-derived extracellular vesicles (MkEVs), the gene therapy cargo comprising a gene-editing protein and/or associated elements for gene-editing functionality directed against a FA-related. In embodiments, the present treatments of FA provide for a gene therapy cargo, in or associated with the present megakaryocyte-derived extracellular vesicles (MkEVs), the gene therapy cargo comprising a gene-editing protein and/or associated elements for gene-editing functionality directed against a FA-related gene, selected from FANCA, FANCB, FANCC, FANCE, FANCF, FANCG, FANCL, FANCM, FANCD1, FANCJ, FANCN and FANCP. In embodiments, the gene-editing protein provides a corrective edit that allows for a functional FA protein.

In embodiments, the present disclosure relates to a method for increasing or restoring the levels and/or function of Fanconi Anemia protein (FANG) e.g. in a target cell, e.g. hematopoietic stem cells, by delivering a therapeutic cargo, e.g. a gene therapy cargo, loaded in or associated with the present megakaryocyte-derived extracellular vesicles (MkEVs). In embodiments, the level and/or function of one or more FA-related genes is restored to reach undiseased levels and/or undiseased function and/or the normal level of a patient not afflicted with FA. In embodiments, the level and/or function of one or more FA-related genes is restored to substantially the same levels and/or function as undiseased levels and/or undiseased function and/or the normal level of a patient not afflicted with FA. In embodiments, the level and/or function of one or more FA-related genes is restored to about 1% to about 99%, about 1% to about 5%, about 5% to about 10%, about 10% to about 20%, about 20% to about 30%, about 30% to about 40%, about 40% to about 50%, about 50% to about 60%, about 60% to about 70%, about 70% to about 70%, about 80% to about 90%, about 90% to about 99% of undiseased levels and/or undiseased function and/or the normal level of a patient not afflicted with FA. In a non-limiting example, the level and/or function of one or more FA-related genes is restored to about 5% to about 10% of undiseased levels and/or undiseased function and/or the normal level of a patient not afflicted with FA, resulting in clinical benefits and/or a favorable risk/benefit profile.

In embodiments, the level and/or function of one or more FA-related genes improves over time after treatment with the present megakaryocyte-derived extracellular vesicles (MkEVs). In embodiments, the level and/or function of one or more FA-related genes is improved to reach to substantially the same levels and/or function as undiseased levels and/or undiseased function and/or the normal level of a patient not afflicted with FA. In embodiments, the level and/or function of one or more FA-related genes is improved by about 1% to about 99%, about 1% to about 5%, about 5% to about 10%, about 10% to about 20%, about 20% to about 30%, about 30% to about 40%, about 40% to about 50%, about 50% to about 60%, about 60% to about 70%, about 70% to about 70%, about 80% to about 90%, about 90% to about 99% as compared to undiseased levels and/or undiseased function and/or the normal level of a patient not afflicted with FA. In a non-limiting example, the level and/or function of one or more FA-related genes is improved to about 5% to about 10% as compared to undiseased levels and/or undiseased function and/or the normal level of a patient not afflicted with FA, resulting in clinical benefits and/or a favorable risk/benefit profile.

In embodiments, the present disclosure relates to a method for increasing or restoring the levels and/or function of one or more FA-related genes, e.g. in a target cell, e.g. hematopoietic stem cells, by delivering a therapeutic cargo, e.g. a gene therapy cargo, loaded in or associated with the present megakaryocyte-derived extracellular vesicles (MkEVs). In embodiments, the level and/or function of one or more FA-related genes is restored to undiseased levels and/or undiseased function. In embodiments, the level and/or function of one or more FA-related genes is restored to substantially the same levels and/or function as undiseased levels and/or undiseased function. In embodiments, the one or more FA-related gene is selected from FANCA, FANCB, FANCC, FANCD1 (BRCA2), FANCD2, FANCE, FANCF, FANCG, FANCI, FANCJ (BRIP1), FANCL, FANCM, FANCN (PALB2), FANCO (RAD51C), FANCP (SLX4), FANCQ (ERCC4), FANCR (Rad51), FANGS (BRCA1), FANCT (UBE2T), FANCU (XRCC2), FANCV (REV7) and FANCW (RFWD3).

In embodiments, the FA is caused by and/or the subject receiving treatment has and/or the present methods correct, mutations in one or more of genes of the FA pathway.

In embodiments, the FA is caused by and/or the subject receiving treatment has and/or the present methods correct, mutations in one or more of genes of the FA core complex.

In embodiments, the FA is caused by and/or the subject receiving treatment has and/or the present methods correct mutations in one or more of FANCA, FANCB, FANCC, FANCD1 (BRCA2), FANCD2, FANCE, FANCF, FANCG, FANCI, FANCJ (BRIP1), FANCL, FANCM, FANCN (PALB2), FANCO (RAD51C), FANCP (SLX4), FANCQ (ERCC4), FANCR (Rad51), FANGS (BRCA1), FANCT (UBE2T), FANCU (XRCC2), FANCV (REV7) and FANCW (RFWD3).

In embodiments, the FA is caused by and/or the subject receiving treatment has and/or the present methods correct mutations in one or more of FANCD1 (BRCA2), FANCJ (BRIP1), FANCB, FANCD2, FANCE, FANCF, FANCI, FANCQ (ERCC4), FANCL, FANCM, FANCN (PALB2), FANCO (RAD51C), FANCP (SLX4), and FANCT (UBE2T).

In embodiments, the FA is caused by and/or the subject receiving treatment has and/or the present methods correct mutations in one or more of FANCA, FANCB, FANCC, FANCE, FANCF, FANCG, and FANCL.

In embodiments, the FA is caused by and/or the subject receiving treatment has and/or the present methods correct mutations in one or more of FANCM, FANCD1, FANCJ, FANCN and FANCP.

In embodiments, the FA is caused by and/or the subject receiving treatment has and/or the present methods correct mutations in one or more of FANCA, FANCC, and FANCG.

In embodiments, the FA is caused by and/or the subject receiving treatment has and/or the present methods correct mutations in FANCR (Rad51).

In embodiments, the FA is caused by and/or the subject receiving treatment has and/or the present methods correct mutations in one or more of the following genes or loci: FANCA (16q24.3) FANCB (Xp22.31), FANCC (9q22.3), FANCD1 (BRCA2) (13q12.3), FANCD2 (3p25.3), FANCE (6p21.3), FANCF (11p15), FANCG (XRCC9) (9p13), FANCI (KIAA1794) (15q25), FANCJ (BRIP1) (17q22.3), FANCL (PHF9/POG) (2p16.1), FANCM (Hef) (14q21.3) FANCN (PALB2) (16p12.1), FANCO (RAD51C) (17q25.1), FANCP (SLX4) (16p13.3), and FANCQ (XPF/ERCC4) (16p13.12), FANCR (Rad51) (15q15), FANGS (BRCA1) (17q21.31), FANCT (UBE2T)(1q32.1), FANCU (XRCC2)(7q36.1), FANCV (REV7) (1p36.22), and FANCW (RFWD3) (16q23.1).

In embodiments, the FA is caused by and/or the subject receiving treatment has and/or the present methods correct mutations in one or more of the following genes or loci: FANCA (16q24.3) FANCB (Xp22.31), FANCC (9q22.3), FANCD1 (BRCA2) (13q12.3), FANCD2 (3p25.3), FANCE (6p21.3), FANCF (11p15), FANCG (XRCC9) (9p13), FANCI (KIAA1794) (15q25), FANCJ (BRIP1) (17q22.3), FANCL (PHF9/POG) (2p16.1), FANCM (Hef) (14q21.3) FANCN (PALB2) (16p12.1), FANCO (RAD51C) (17q25.1), FANCP (SLX4) (16p13.3), and FANCQ (XPF/ERCC4) (16p13.12).

In embodiments, the FA is caused by and/or the subject receiving treatment has and/or the present methods correct one or more mutations in one or more FA-related genes. Non-limiting examples of mutations can be found in US 2014/0087397 and the Rockefeller University Fanconi Anemia Mutation Database (see, rockefeller.edu/fanconi/), both of which are incorporated by reference herein in their entireties. In embodiments, the FA is caused by and/or the subject receiving treatment has and/or the present methods correct the one or more of the following mutations:

*FANCC c.456+4A>T (IVS4)*

*FANCD1 c.6174delT*

*FANCA c.3788_3790del*

*FANCG c.1077−2A>G*

*FANCC c.67delG (322delG)*

*FANCG c.1480+1G>C*

*FANCA c.2172dupG, 4275delT, c.2574C>G, c.890−893del*

*FANCA c.2546delC, c.3720_3724del*

*FANCC c.456+4A>T*

*FANCG c.307+1G>C, c.1066C>T*

*FANCA c.2546delC, c.3720_3724del*

*FANCG c.307+1G>C, c.1066C>T*

*FANCC c.165+1G>T*

*FANCA c.1007−?_3066+?del, c.1007−?_1626+?del, c.3398delA*

*FANCG c.637_643del*

*FANCA c.295C>T*

*FANCD2 c.1948−16T>G.*

In embodiments, the FA subject, i.e. the subject receiving treatment is characterized by chromosome instability.

In embodiments, the FA subject, i.e. the subject receiving treatment is characterized by autosomal recessive inheritance of one or more of BRCA2, BRIP1, FANCB, FANCD2, FANCE, FANCF, FANCI, ERCC4, FANCL, FANCM, PALB2, RAD51C, SLX4, and UBE2T.

In embodiments, the FA subject, i.e. the subject receiving treatment is characterized by X-linked recessive inheritance of FANCB.

In embodiments, the FA subject, i.e. the subject receiving treatment is characterized by autosomal dominant inheritance of RAD51.

In embodiments, the subject is a member of a population known to have a founder mutation related to FA, e.g. Ashkenazi Jews (FANCC, BRCA2/FANCD1), northern Europeans (FANCC), Afrikaners (FANCA), sub-Saharan Blacks (FANCG), or Spanish Romas (FANCA).

In embodiments, the therapeutic agent is capable of increasing the expression of a functional FA-related gene or a protein product thereof by about 1-fold, about 2 fold, about 3 fold, about 4 fold, about 5-fold, about 10 fold, about 15-fold, about 18-fold about 20-fold, about 30-fold, about 40-fold about 50-fold, about 60-fold, about 100-fold, about 500-fold, or about 1000-fold compared to expression of the non-functional and/or deficient FA-related gene or protein product.

In embodiments, the therapeutic agent is a small molecule therapeutic agent, or a biologic therapeutic agent. In embodiments, the biologic therapeutic agent is used for gene therapy. In embodiments, the biologic therapeutic agent encodes a functional protein or a recombinant protein. In embodiments, the functional protein or the recombinant protein comprises a wild-type protein, a fusion protein, a cytokine, an antigen, and a peptide, an antibody or an antibody fragment. In embodiments, the therapeutic agent is a nucleic acid therapeutic agent. In embodiments, the nucleic acid therapeutic agent expresses a wild-type functional FA gene, and/or comprises a nucleic acid encoding a functional FA-related gene, or a protein product thereof, or a nucleic acid encoding a gene-editing protein capable of creating a functional FA-related gene, or a protein product thereof, or a ribonucleoprotein gene-editing complex capable of creating a functional FA-related gene or a protein product thereof. In embodiments, the nucleic acid therapeutic agent is selected from one or more non-autologous and/or recombinant nucleic acid constructs selected from mRNA, tRNA, rRNA, siRNA, microRNA, regulating RNA, non-coding and coding RNA, linear DNA, plasmid DNA, or DNA fragments.

In embodiments, the present methods of treatment reduce, ameliorate or eliminate various symptoms or presentations of FA, e.g. a bone marrow dysfunction, a deficiency in blood cells or the production of abnormal cells. In embodiments, the present methods of treatment reduce, ameliorate or eliminate the patient deficiency in one or more of white blood cell count, neutrophil count, reticulocyte count, platelet count, and red blood cell count, bone marrow, or producing of normal cells.

In embodiments, the present methods of treatment reduce, ameliorate or eliminate various symptoms or presentations of FA, e.g. anemia, thrombocytopenia, and neutropenia.

In embodiments, the present methods of treatment reduce, ameliorate or eliminate various secondary complications of FA, such as, but not limited to, the likelihood of the patient developing one or more of headaches, dizziness, fatigue, shortness of breath, anemia, thrombocytopenia, neutropenia, myelodysplastic syndromes (MDS), kidney-related diseases and acute myeloid leukemia (AML).

In embodiments, the present methods reduce, ameliorate or eliminate FA, as detected or detectable using one or more of a chromosome breakage test (optionally with DEB (diepoxybutane) and/or MMC (mitomycin C)), cell cycle analysis in peripheral blood lymphocytes, complete peripheral blood counts, mitomycin C resistance testing, and mutation analysis (e.g. chromosomal, sequencing, etc.), measurement of complete blood count, and/or restoration or partial restoration of FANG protein production and localization.

In embodiments, the present methods supplement or supplant one or more FA treatment agents or modalities, selected from androgen, hematopoietic growth factors, transfusion support, hematopoietic stem cell transplantation (HSCT), and surgery (e.g. to correct skeletal malformations such as those affecting the thumbs and forearm bones, cardiac defects, and gastrointestinal abnormalities such as tracheoesophageal fistula or esophageal atresia, as well as anal atresia).

In embodiments, the wherein the treating obviates the need for blood and/or bone marrow transplantation, androgen therapy, synthetic growths factors therapy, chemotherapy and/or surgery.

In embodiments, the present treatments of FA provide for gene replacement of any of the FA-related gene described herein.

In embodiments, the present treatments of FA provide for a gene therapy cargo, in or associated with the present megakaryocyte-derived extracellular vesicles (MkEVs), the gene therapy cargo comprising a nucleic acid encoding a wild type, unmutated and/or functional FA-related gene, selected from FANCA, FANCB, FANCC, FANCD1 (BRCA2), FANCD2, FANCE, FANCF, FANCG, FANCI, FANCJ (BRIP1), FANCL, FANCM, FANCN (PALB2), FANCO (RAD51C), FANCP (SLX4), FANCQ (ERCC4), FANCR (Rad51), FANGS (BRCA1), FANCT (UBE2T), FANCU (XRCC2), FANCV (REV7) and FANCW (RFWD3). In embodiments, the gene therapy cargo is DNA or RNA.

In embodiments, the present treatments of FA provide for a gene therapy cargo, in or associated with the present megakaryocyte-derived extracellular vesicles (MkEVs), the gene therapy cargo comprising a nucleic acid encoding a wild type, unmutated and/or functional FA-related gene, selected from FANCA, FANCB, FANCC, FANCE, FANCF, FANCG, FANCL, FANCM, FANCD1, FANCJ, FANCN and FANCP. In embodiments, the gene therapy cargo is DNA or RNA.

In embodiments, the present treatments of FA provide for a gene therapy cargo, in or associated with the present megakaryocyte-derived extracellular vesicles (MkEVs), the gene therapy cargo comprising a gene-editing protein and/or associated elements for gene-editing functionality directed against a FA-related. In embodiments, the present treatments of FA provide for a gene therapy cargo, in or associated with the present megakaryocyte-derived extracellular vesicles (MkEVs), the gene therapy cargo comprising a gene-editing protein and/or associated elements for gene-editing functionality directed against a FA-related gene, selected from FANCA, FANCB, FANCC, FANCD1 (BRCA2), FANCD2, FANCE, FANCF, FANCG, FANCI, FANCJ (BRIP1), FANCL, FANCM, FANCN (PALB2), FANCO (RAD51C), FANCP (SLX4), FANCQ (ERCC4), FANCR (Rad51), FANGS (BRCA1), FANCT (UBE2T), FANCU (XRCC2), FANCV (REV7) and FANCW (RFWD3). In embodiments, the gene-editing protein provides a corrective edit that allows for a functional FA protein.

In embodiments, the present treatments of FA provide for a gene therapy cargo, in or associated with the present megakaryocyte-derived extracellular vesicles (MkEVs), the gene therapy cargo comprising a gene-editing protein and/or associated elements for gene-editing functionality directed against a FA-related. In embodiments, the present treatments of FA provide for a gene therapy cargo, in or associated with the present megakaryocyte-derived extracellular vesicles (MkEVs), the gene therapy cargo comprising a gene-editing protein and/or associated elements for gene-editing functionality directed against a FA-related gene, selected from FANCA, FANCB, FANCC, FANCE, FANCF, FANCG, FANCL, FANCM, FANCD1, FANCJ, FANCN and FANCP. In embodiments, the gene-editing protein provides a corrective edit that allows for a functional FA protein.

In embodiments, the nucleic acid therapeutic agent encodes a gene-editing protein, and/or associated elements for gene-editing functionality, gene-editing protein is selected from a zinc finger (ZF), transcription activator-like effector (TALE), meganuclease, and clustered regularly interspaced short palindromic repeat (CRISPR)-associated protein. In embodiments, CRISPR-associated protein is selected from Cas9, xCas9, Cas12a (Cpf1), Cas13a, Cas14, CasX, CasY, a Class 1 Cas protein, a Class 2 Cas protein, MAD7, and gRNA complexes thereof.

Megakaryocyte-Derived Extracellular Vesicles

In one aspect, the present disclosure relates to a composition comprising: a plurality of substantially purified megakaryocyte-derived extracellular vesicles comprising a lipid bilayer membrane surrounding a lumen and the lipid bilayer membrane comprises one or more proteins associated with or embedded within. In embodiments, the megakaryocyte-derived extracellular vesicles are derived from a human pluripotent stem cell. In embodiments, the megakaryocyte-derived extracellular vesicle lumen comprises one or more megakaryocyte-derived nucleic acid molecules selected from mRNA, tRNA, rRNA, siRNA, microRNA, regulating RNA, and non-coding and coding RNA.

In embodiments, the megakaryocyte-derived extracellular vesicles comprise a cargo in the lumen or a cargo associated with the surface of the megakaryocyte-derived extracellular vesicles. In embodiments, the megakaryocyte-derived extracellular vesicles comprise a cargo in the lumen and is associated with the surface of the megakaryocyte-derived extracellular vesicles. In embodiments, the megakaryocyte-derived extracellular vesicles comprise cargo suitable for modifying a cell and/or cargo associated with the surface of the megakaryocyte-derived extracellular vesicles. In embodiments, the modifying the cell includes gene therapy, including but not limited to the use of a biologic therapeutic agent encoding a functional protein or a recombinant protein. In embodiments, the modifying the cell includes gene editing. In embodiments, the megakaryocyte-derived extracellular vesicles comprise cargo suitable for gene editing the cell and/or cargo associated with the surface of the megakaryocyte-derived extracellular vesicles. In embodiments, in addition to or as an alternative to the cargo located in the lumen of the megakaryocyte-derived extracellular vesicles, the cargo is loaded into the megakaryocyte for packaging into the extracellular vesicles. In embodiments, in addition to or as an alternative to the cargo located in the lumen of the megakaryocyte-derived extracellular vesicles, the cargo is loaded directly into the megakaryocyte-derived extracellular vesicles.

In another aspect, the present disclosure relates to a composition comprising: a plurality of substantially purified megakaryocyte-derived extracellular vesicles comprising a lipid bilayer membrane surrounding a lumen and the lipid bilayer membrane comprises one or more proteins associated with or embedded within. In embodiments, the megakaryocyte-derived extracellular vesicles are derived from a human pluripotent stem cell. In embodiments, the megakaryocyte-derived extracellular vesicle comprises one or more nucleic acid molecules selected from mRNA, tRNA, rRNA, siRNA, microRNA, regulating RNA, and non-coding and coding RNA associated with the surface of the vesicle, and the lipid bilayer membrane comprises one or more proteins associated with or embedded within. In embodiments, the nucleic acid molecule is exogenously derived. In embodiments, the megakaryocyte-derived extracellular vesicles comprise cargo suitable for modifying a cell and/or cargo associated with the surface of the megakaryocyte-derived extracellular vesicles. In embodiments, the modifying the cell includes gene therapy, including but not limited to the use of a biologic therapeutic agent encoding a functional protein or a recombinant protein. In embodiments, the modifying the cell includes gene editing. In embodiments, in addition to or as an alternative to the cargo located in the lumen of the megakaryocyte-derived extracellular vesicles, the cargo is loaded into the megakaryocyte for packaging into the extracellular vesicles. In embodiments, in addition to or as an alternative to the cargo located in the lumen of the megakaryocyte-derived extracellular vesicles, the cargo is loaded directly into the megakaryocyte-derived extracellular vesicles.

In one aspect, the present disclosure relates to a composition comprising: a plurality of substantially purified megakaryocyte-derived extracellular vesicles comprising a lipid bilayer membrane surrounding a lumen and the lipid bilayer membrane comprises one or more proteins associated with or embedded within. In embodiments, the megakaryocyte-derived extracellular vesicles are derived from a human pluripotent stem cell. In embodiments, the megakaryocyte-derived extracellular vesicles are suitable for loading with cargo into the lumen. In embodiments, the cargo comprises one or more agent. In embodiments, the agent is one or more therapeutic agents, including therapeutic agents described herein. In embodiments, the cargo comprises one or more megakaryocyte-derived nucleic acid molecules selected from mRNA, tRNA, rRNA, siRNA, microRNA, regulating RNA, and non-coding and coding RNA. In embodiments, the megakaryocyte-derived extracellular vesicles comprise a cargo in the lumen or a cargo associated with the surface of the megakaryocyte-derived extracellular vesicles. In embodiments, the megakaryocyte-derived extracellular vesicles comprise a cargo in the lumen and is associated with the surface of the megakaryocyte-derived extracellular vesicles. In embodiments, in addition to or as an alternative to the cargo located in the lumen of the megakaryocyte-derived extracellular vesicles, the cargo is loaded into the megakaryocyte for packaging into the extracellular vesicles. In embodiments, in addition to or as an alternative to the cargo located in the lumen of the megakaryocyte-derived extracellular vesicles, the cargo is loaded directly into the megakaryocyte-derived extracellular vesicles. In embodiments, the megakaryocyte-derived extracellular vesicles are suitable for loading with cargo associated with the surface of the megakaryocyte-derived extracellular vesicles.

In another aspect, the present disclosure relates to a composition comprising: a plurality of substantially purified megakaryocyte-derived extracellular vesicles comprising a lipid bilayer membrane surrounding a lumen and derived from a human pluripotent stem cell, wherein: the megakaryocyte-derived extracellular vesicle lumen comprises cargo and the lipid bilayer membrane comprises one or more proteins associated with or embedded within. In embodiments, the cargo comprises one or more agents. In embodiments, the agent is one or more therapeutic agents, including therapeutic agents described herein. In embodiments, the cargo comprises one or more megakaryocyte-derived nucleic acid molecules selected from mRNA, tRNA, rRNA, siRNA, microRNA, regulating RNA, and non-coding and coding RNA. In embodiments, the megakaryocyte-derived extracellular vesicles comprise a cargo in the lumen or a cargo associated with the surface of the megakaryocyte-derived extracellular vesicles. In embodiments, the megakaryocyte-derived extracellular vesicles comprise a cargo in the lumen and is associated with the surface of the megakaryocyte-derived extracellular vesicles. In embodiments, in addition to or as an alternative to the cargo located in the lumen of the megakaryocyte-derived extracellular vesicles, the cargo is loaded into the megakaryocyte for packaging into the extracellular vesicles. In embodiments, in addition to or as an alternative to the cargo located in the lumen of the megakaryocyte-derived extracellular vesicles, the cargo is loaded directly into the megakaryocyte-derived extracellular vesicles. In embodiments, the megakaryocyte-derived extracellular vesicles are suitable for loading with cargo associated with the surface of the megakaryocyte-derived extracellular vesicles.

In one aspect, the present disclosure relates to a composition comprising: a plurality of substantially purified megakaryocyte-derived extracellular vesicles comprising a lipid bilayer membrane surrounding a lumen and derived from a human pluripotent stem cell, wherein: the megakaryocyte-derived extracellular vesicle lumen comprises one or more megakaryocyte-derived nucleic acid molecules selected from mRNA, tRNA, rRNA, siRNA, microRNA, regulating RNA, and non-coding and coding RNA and the lipid bilayer membrane comprises one or more proteins associated with or embedded within.

In another aspect, the present disclosure relates to a pharmaceutical composition comprising a composition comprising megakaryocyte-derived extracellular vesicles and/or a plurality of megakaryocyte-derived extracellular vesicles disclosed herein and a pharmaceutically acceptable excipient or carrier.

In another aspect, the present disclosure relates to a method for transferring a deliverable therapeutic agent, comprising: (a) obtaining the megakaryocyte-derived extracellular vesicles of a composition comprising megakaryocyte-derived extracellular vesicles and/or a plurality of megakaryocyte-derived extracellular vesicles disclosed herein; (b) incubating the megakaryocyte-derived extracellular vesicle with a therapeutic agent to allow the therapeutic agent to populate the lumen of the megakaryocyte-derived extracellular vesicle and yield a deliverable therapeutic agent; and (c) administering the deliverable therapeutic agent to a patient or contacting the deliverable therapeutic agent with a biological cell in vitro and administering the contacted biological cell to a patient afflicted by FA, experiencing FA-related symptoms and/or likely to develop FA.

In another aspect, the present disclosure relates to a method for transferring a deliverable therapeutic agent, comprising: (a) obtaining the megakaryocyte-derived extracellular vesicles disclosed herein; (b) incubating the megakaryocyte-derived extracellular vesicle with a therapeutic agent to allow the therapeutic agent to populate the lumen of the megakaryocyte-derived extracellular vesicle and/or associate with the surface of the megakaryocyte-derived extracellular vesicle and yield a deliverable therapeutic agent; and (c) administering the deliverable therapeutic agent to a patient or contacting the deliverable therapeutic agent with a biological cell in vitro and administering the contacted biological cell to a patient afflicted by FA, experiencing FA-related symptoms and/or likely to develop FA.

In another aspect, the present disclosure relates to a method of generating the megakaryocyte-derived extracellular vesicles disclosed herein, comprising: (a) obtaining a human pluripotent stem cell, the human pluripotent stem cell being a primary CD34+ hematopoietic stem cell sourced from peripheral blood or cord blood or bone marrow; (b) differentiating the human pluripotent stem cell to a megakaryocyte in the absence of added erythropoietin and in the presence of added thrombopoietin; and (c) isolating megakaryocyte-derived extracellular vesicles from the megakaryocytes, further wherein the generated megakaryocyte-derived extracellular vesicles comprise a cargo for modifying a cell to provide a functional Fanconi anemia (FA) related gene and/or to repair a mutated functional FA-related gene therein.

Biomarker Profile or Fingerprint

In various embodiments, the megakaryocyte-derived extracellular vesicles of the disclosure are characterized by a unique biomarker profile or fingerprint that distinguishes them from, for instance, naturally-occurring megakaryocyte-derived extracellular vesicles and/or vesicles or extracellular vesicles derived from platelets. In various embodiments, the present megakaryocyte-derived extracellular vesicles are characterized by a such a biomarker profile or fingerprint, which comprises the identity (e.g. the presence or absence) or amount (e.g. substantial presence or substantial absence of a biomarker in a megakaryocyte-derived extracellular vesicle population; or presence on or absence from a majority of megakaryocyte-derived extracellular vesicle in a population; or percentage megakaryocyte-derived extracellular vesicles having a biomarker).

In embodiments, the substantially purified megakaryocyte-derived extracellular vesicles comprise a lipid bilayer membrane surrounding a lumen and derived from a human pluripotent stem cell, wherein the lipid bilayer membrane comprises one or more proteins (a.k.a. biomarkers) associated with or embedded within.

In embodiments, the substantially purified megakaryocyte-derived extracellular vesicles comprise a lipid bilayer membrane surrounding a lumen, wherein the lipid bilayer membrane comprises one or more proteins (a.k.a. biomarkers) associated with or embedded within. In embodiments, the megakaryocyte-derived extracellular vesicles are derived from a human pluripotent stem cell.

In embodiments, the lipid bilayer membrane comprises proteins selected from CD18, CD43, CD11 b, CD62P, CD41, CD61, CD21, CD51, phosphatidylserine (PS), CLEC-2, LAMP-1 (CD107a), CD63, CD42b, CD9, CD31, CD47, CD147, CD54, CD32a, and GPVI.

In embodiments, the lipid bilayer membrane comprises phosphatidylserine, e.g., without limitation by testing for Annexin V.

In embodiments, the lipid bilayer membrane comprises one or more proteins selected from CD62P, CD41, and CD61.

In embodiments, greater than about 40%, greater than about 50%, greater than about 60%, greater than about 70%, greater than about 80%, greater than about 90%, greater than about 95%, or greater than about 99% of the megakaryocyte-derived extracellular vesicles comprising a lipid bilayer membrane comprising CD41 also comprise CD61 in the lipid bilayer membrane.

In embodiments, the present megakaryocyte-derived extracellular vesicles are characterized by the expression and/or presence of one or more of CD54, CD18, CD43, CD11 b, CD62P, CD41, CD61, CD21, CD51, and CLEC-2. In embodiments, the present megakaryocyte-derived extracellular vesicles are characterized by the expression and/or presence of one or more of PS, CD62P, LAMP-1 (CD107a), CD42b, CD9, CD43, CD31, and CD11b. In embodiments, the present megakaryocyte-derived extracellular vesicles are characterized by the expression and/or presence of one or more of PS, CD61, CD62P, LAMP-1 (CD107a), CLEC-2, and CD63. In embodiments, the present megakaryocyte-derived extracellular vesicles are characterized by the expression and/or presence of one or more of PS, CD62P, CLEC-2, CD9, CD31, CD147, CD32a, and GPVI. In embodiments, the present megakaryocyte-derived extracellular vesicles are characterized by the expression and/or presence of one or more of PS, CD62P, LAMP-1 (CD107a), CLEC-2, CD9, and CD31. In embodiments, the present megakaryocyte-derived extracellular vesicles are characterized by the expression and/or presence of one or more of CD62P, CD41, and CD61. In embodiments, the present megakaryocyte-derived extracellular vesicles are characterized by a substantial expression and/or presence of one or more of CD54, CD18, CD43, CD11 b, CD62P, CD41, CD61, CD21, CD51, and CLEC-2. In embodiments, the present megakaryocyte-derived extracellular vesicles are characterized by a substantial expression and/or presence of one or more of CD62P, CD41, and CD61. In embodiments, the present megakaryocyte-derived extracellular vesicles are characterized by not expressing and/or comprising a substantial amount of DRAQ5. In embodiments, the present megakaryocyte-derived extracellular vesicles are characterized by being substantially free of DRAQ5.

In embodiments, greater than about 50% of the megakaryocyte-derived extracellular vesicles comprise a lipid bilayer membrane comprising CD62P. In embodiments, greater than about 40% of the megakaryocyte-derived extracellular vesicles comprise a lipid bilayer membrane comprising CD62P. In embodiments, greater than about 60% of the megakaryocyte-derived extracellular vesicles comprise a lipid bilayer membrane comprising CD62P. In embodiments, greater than about 70% of the megakaryocyte-derived extracellular vesicles comprise a lipid bilayer membrane comprising CD62P. In embodiments, greater than about 80% of the megakaryocyte-derived extracellular vesicles comprise a lipid bilayer membrane comprising CD62P. In embodiments, greater than about 90% of the megakaryocyte-derived extracellular vesicles comprise a lipid bilayer membrane comprising CD62P. In embodiments, greater than about 95% of the megakaryocyte-derived extracellular vesicles comprise a lipid bilayer membrane comprising CD62P. In embodiments, greater than about 99% of the megakaryocyte-derived extracellular vesicles comprise a lipid bilayer membrane comprising CD62P.

In embodiments, about 50% or less of the megakaryocyte-derived extracellular vesicles comprise a lipid bilayer membrane comprising CD62P. In embodiments, about 40% or less of the megakaryocyte-derived extracellular vesicles comprise a lipid bilayer membrane comprising CD62P. In embodiments, about 60% or less of the megakaryocyte-derived extracellular vesicles comprise a lipid bilayer membrane comprising CD62P. In embodiments, about 70% or less of the megakaryocyte-derived extracellular vesicles comprise a lipid bilayer membrane comprising CD62P. In embodiments, about 80% or less of the megakaryocyte-derived extracellular vesicles comprise a lipid bilayer membrane comprising CD62P. In embodiments, about 90% or less of the megakaryocyte-derived extracellular vesicles comprise a lipid bilayer membrane comprising CD62P. In embodiments, about 95% or less of the megakaryocyte-derived extracellular vesicles comprise a lipid bilayer membrane comprising CD62P. In embodiments, about 99% or less of the megakaryocyte-derived extracellular vesicles comprise a lipid bilayer membrane comprising CD62P.

In embodiments, less than about 50% of the megakaryocyte-derived extracellular vesicles comprise a lipid bilayer membrane comprising CD62P. In embodiments, less than about 40% of the megakaryocyte-derived extracellular vesicles comprise a lipid bilayer membrane comprising CD62P. In embodiments, less than about 30% of the megakaryocyte-derived extracellular vesicles comprise a lipid bilayer membrane comprising CD62P. In embodiments, less than about 25% of the megakaryocyte-derived extracellular vesicles comprise a lipid bilayer membrane comprising CD62P. In embodiments, less than about 20% of the megakaryocyte-derived extracellular vesicles comprise a lipid bilayer membrane comprising CD62P. In embodiments, less than about 15% of the megakaryocyte-derived extracellular vesicles comprise a lipid bilayer membrane comprising CD62P. In embodiments, less than about 10% of the megakaryocyte-derived extracellular vesicles comprise a lipid bilayer membrane comprising CD62P. In embodiments, less than about 5% of the megakaryocyte-derived extracellular vesicles comprise a lipid bilayer membrane comprising CD62P. In embodiments, less than about 1% of the megakaryocyte-derived extracellular vesicles comprise a lipid bilayer membrane comprising CD62P.

In embodiments, between about 1% to about 99% of the megakaryocyte-derived extracellular vesicles comprise a lipid bilayer membrane comprising CD62P. In embodiments, between about 1% to about 50% of the megakaryocyte-derived extracellular vesicles comprise a lipid bilayer membrane comprising CD62P. In embodiments, between about 1% to about 25% of the megakaryocyte-derived extracellular vesicles comprise a lipid bilayer membrane comprising CD62P. In embodiments, between about 1% to about 10% of the megakaryocyte-derived extracellular vesicles comprise a lipid bilayer membrane comprising CD62P. In embodiments, between about 1% to about 5% of the megakaryocyte-derived extracellular vesicles comprise a lipid bilayer membrane comprising CD62P. In embodiments, between about 1% to about 2% of the megakaryocyte-derived extracellular vesicles comprise a lipid bilayer membrane comprising CD62P. In embodiments, between about 50% to about 99% of the megakaryocyte-derived extracellular vesicles comprise a lipid bilayer membrane comprising CD62P. In embodiments, between about 75% to about 99% of the megakaryocyte-derived extracellular vesicles comprise a lipid bilayer membrane comprising CD62P. In embodiments, between about 90% to about 99% of the megakaryocyte-derived extracellular vesicles comprise a lipid bilayer membrane comprising CD62P. In embodiments, between about 95% to about 99% of the megakaryocyte-derived extracellular vesicles comprise a lipid bilayer membrane comprising CD62P.

In embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD62P.

In embodiments, the megakaryocyte-derived extracellular vesicles are free of, or substantially free of CD62P.

In embodiments, the megakaryocyte-derived extracellular vesicles of the disclosure are characterized by a higher expression and/or presence of CD62P than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD62P than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles of the disclosure are characterized by a lower expression and/or presence of CD62P than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD62P than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 4-fold to about a 32-fold or about an 8-fold to about a 16-fold lower amount of CD62P than platelet free plasma (PFP) MkEVs. In embodiments, the megakaryocyte-derived extracellular vesicles have about a 15-fold or about a 16-fold lower amount of CD62P than platelet free plasma (PFP) MkEVs. In embodiments, the megakaryocyte-derived extracellular vesicles have about a 32-fold to about a 128-fold, about a 50-fold to about a 75-fold, or about a 60-fold to about a 70-fold lower amount of CD62P than platelet derived extracellular vesicles (PLT EVs). In embodiments, the megakaryocyte-derived extracellular vesicles have about a 60-fold, about a 64-fold, or about a 70-fold lower amount of CD62P than platelet derived extracellular vesicles (PLT EVs).

In embodiments, greater than about 50% of the megakaryocyte-derived extracellular vesicles comprise a lipid bilayer membrane comprising CD41. In embodiments, greater than about 40% of the megakaryocyte-derived extracellular vesicles comprise a lipid bilayer membrane comprising CD41. In embodiments, greater than about 60% of the megakaryocyte-derived extracellular vesicles comprise a lipid bilayer membrane comprising CD41. In embodiments, greater than about 70% of the megakaryocyte-derived extracellular vesicles comprise a lipid bilayer membrane comprising CD41. In embodiments, greater than about 80% of the megakaryocyte-derived extracellular vesicles comprise a lipid bilayer membrane comprising CD41. In embodiments, greater than about 90% of the megakaryocyte-derived extracellular vesicles comprise a lipid bilayer membrane comprising CD41. In embodiments, greater than about 95% of the megakaryocyte-derived extracellular vesicles comprise a lipid bilayer membrane comprising CD41. In embodiments, greater than about 99% of the megakaryocyte-derived extracellular vesicles comprise a lipid bilayer membrane comprising CD41.

In embodiments, about 50% or less of the megakaryocyte-derived extracellular vesicles comprise a lipid bilayer membrane comprising CD41. In embodiments, about 40% or less of the megakaryocyte-derived extracellular vesicles comprise a lipid bilayer membrane comprising CD41. In embodiments, about 60% or less of the megakaryocyte-derived extracellular vesicles comprise a lipid bilayer membrane comprising CD41. In embodiments, about 70% or less of the megakaryocyte-derived extracellular vesicles comprise a lipid bilayer membrane comprising CD41. In embodiments, about 80% or less of the megakaryocyte-derived extracellular vesicles comprise a lipid bilayer membrane comprising CD41. In embodiments, about 90% or less of the megakaryocyte-derived extracellular vesicles comprise a lipid bilayer membrane comprising CD41. In embodiments, about 95% or less of the megakaryocyte-derived extracellular vesicles comprise a lipid bilayer membrane comprising CD41. In embodiments, about 99% or less of the megakaryocyte-derived extracellular vesicles comprise a lipid bilayer membrane comprising CD41.

In embodiments, less than about 50% of the megakaryocyte-derived extracellular vesicles comprise a lipid bilayer membrane comprising CD41. In embodiments, less than about 40% of the megakaryocyte-derived extracellular vesicles comprise a lipid bilayer membrane comprising CD41. In embodiments, less than about 30% of the megakaryocyte-derived extracellular vesicles comprise a lipid bilayer membrane comprising CD41. In embodiments, less than about 25% of the megakaryocyte-derived extracellular vesicles comprise a lipid bilayer membrane comprising CD41. In embodiments, less than about 20% of the megakaryocyte-derived extracellular vesicles comprise a lipid bilayer membrane comprising CD41. In embodiments, less than about 15% of the megakaryocyte-derived extracellular vesicles comprise a lipid bilayer membrane comprising CD41. In embodiments, less than about 10% of the megakaryocyte-derived extracellular vesicles comprise a lipid bilayer membrane comprising CD41. In embodiments, less than about 5% of the megakaryocyte-derived extracellular vesicles comprise a lipid bilayer membrane comprising CD41. In embodiments, less than about 1% of the megakaryocyte-derived extracellular vesicles comprise a lipid bilayer membrane comprising CD41.

In embodiments, between about 1% to about 99% of the megakaryocyte-derived extracellular vesicles comprise a lipid bilayer membrane comprising CD41. In embodiments, between about 1% to about 50% of the megakaryocyte-derived extracellular vesicles comprise a lipid bilayer membrane comprising CD41. In embodiments, between about 1% to about 25% of the megakaryocyte-derived extracellular vesicles comprise a lipid bilayer membrane comprising CD41. In embodiments, between about 1% to about 10% of the megakaryocyte-derived extracellular vesicles comprise a lipid bilayer membrane comprising CD41. In embodiments, between about 1% to about 5% of the megakaryocyte-derived extracellular vesicles comprise a lipid bilayer membrane comprising CD41. In embodiments, between about 1% to about 2% of the megakaryocyte-derived extracellular vesicles comprise a lipid bilayer membrane comprising CD41. In embodiments, between about 50% to about 99% of the megakaryocyte-derived extracellular vesicles comprise a lipid bilayer membrane comprising CD41. In embodiments, between about 75% to about 99% of the megakaryocyte-derived extracellular vesicles comprise a lipid bilayer membrane comprising CD41. In embodiments, between about 90% to about 99% of the megakaryocyte-derived extracellular vesicles comprise a lipid bilayer membrane comprising CD41. In embodiments, between about 95% to about 99% of the megakaryocyte-derived extracellular vesicles comprise a lipid bilayer membrane comprising CD41.

In embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD41.

In embodiments, the megakaryocyte-derived extracellular vesicles comprise CD41.

In embodiments, the megakaryocyte-derived extracellular vesicles are characterized by a higher expression and/or presence or CD41 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD41 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence or CD41 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD41 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about an 8-fold or about a 2-fold to about a 4-fold greater amount of CD41/CD61 than platelet free plasma (PFP) MkEVs. In embodiments, the megakaryocyte-derived extracellular vesicles have about a 2-fold, about a 3-fold, or about a 4-fold greater amount of CD41/CD61 than platelet free plasma (PFP) MkEVs. In embodiments, the megakaryocyte-derived extracellular vesicles have about a 1.1-fold to about a 2-fold greater amount of CD41/CD61 than platelet derived extracellular vesicles (PLT EVs). In embodiments, the megakaryocyte-derived extracellular vesicles have about a 1.1-fold or about a 1.2-fold greater amount of CD41/CD61 than platelet derived extracellular vesicles (PLT EVs). In embodiments, the megakaryocyte-derived extracellular vesicles have an amount of CD41/CD61 that is substantially the same as platelet derived extracellular vesicles (PLT EVs).

In embodiments, greater than about 50% of the megakaryocyte-derived extracellular vesicles comprise a lipid bilayer membrane comprising CD61. In embodiments, greater than about 40% of the megakaryocyte-derived extracellular vesicles comprise a lipid bilayer membrane comprising CD61. In embodiments, greater than about 60% of the megakaryocyte-derived extracellular vesicles comprise a lipid bilayer membrane comprising CD61. In embodiments, greater than about 70% of the megakaryocyte-derived extracellular vesicles comprise a lipid bilayer membrane comprising CD61. In embodiments, greater than about 80% of the megakaryocyte-derived extracellular vesicles comprise a lipid bilayer membrane comprising CD61. In embodiments, greater than about 90% of the megakaryocyte-derived extracellular vesicles comprise a lipid bilayer membrane comprising CD61. In embodiments, greater than about 95% of the megakaryocyte-derived extracellular vesicles comprise a lipid bilayer membrane comprising CD61. In embodiments, greater than about 99% of the megakaryocyte-derived extracellular vesicles comprise a lipid bilayer membrane comprising CD61.

In embodiments, about 50% or less of the megakaryocyte-derived extracellular vesicles comprise a lipid bilayer membrane comprising CD61. In embodiments, less than about 40% of the megakaryocyte-derived extracellular vesicles comprise a lipid bilayer membrane comprising CD61. In embodiments, about 60% or less of the megakaryocyte-derived extracellular vesicles comprise a lipid bilayer membrane comprising CD61. In embodiments, about 70% or less of the megakaryocyte-derived extracellular vesicles comprise a lipid bilayer membrane comprising CD61. In embodiments, about 80% or less of the megakaryocyte-derived extracellular vesicles comprise a lipid bilayer membrane comprising CD61. In embodiments, less than about 90% of the megakaryocyte-derived extracellular vesicles comprise a lipid bilayer membrane comprising CD61. In embodiments, about 95% or less of the megakaryocyte-derived extracellular vesicles comprise a lipid bilayer membrane comprising CD61. In embodiments, about 99% or less of the megakaryocyte-derived extracellular vesicles comprise a lipid bilayer membrane comprising CD61.

In embodiments, less than about 50% of the megakaryocyte-derived extracellular vesicles comprise a lipid bilayer membrane comprising CD61. In embodiments, less than about 40% of the megakaryocyte-derived extracellular vesicles comprise a lipid bilayer membrane comprising CD61. In embodiments, less than about 30% of the megakaryocyte-derived extracellular vesicles comprise a lipid bilayer membrane comprising CD61. In embodiments, less than about 25% of the megakaryocyte-derived extracellular vesicles comprise a lipid bilayer membrane comprising CD61. In embodiments, less than about 20% of the megakaryocyte-derived extracellular vesicles comprise a lipid bilayer membrane comprising CD61. In embodiments, less than about 15% of the megakaryocyte-derived extracellular vesicles comprise a lipid bilayer membrane comprising CD61. In embodiments, less than about 10% of the megakaryocyte-derived extracellular vesicles comprise a lipid bilayer membrane comprising CD61. In embodiments, less than about 5% of the megakaryocyte-derived extracellular vesicles comprise a lipid bilayer membrane comprising CD61. In embodiments, less than about 1% of the megakaryocyte-derived extracellular vesicles comprise a lipid bilayer membrane comprising CD61.

In embodiments, between about 1% to about 99% of the megakaryocyte-derived extracellular vesicles comprise a lipid bilayer membrane comprising CD61. In embodiments, between about 1% to about 50% of the megakaryocyte-derived extracellular vesicles comprise a lipid bilayer membrane comprising CD61. In embodiments, between about 1% to about 25% of the megakaryocyte-derived extracellular vesicles comprise a lipid bilayer membrane comprising CD61. In embodiments, between about 1% to about 10% of the megakaryocyte-derived extracellular vesicles comprise a lipid bilayer membrane comprising CD61. In embodiments, between about 1% to about 5% of the megakaryocyte-derived extracellular vesicles comprise a lipid bilayer membrane comprising CD61. In embodiments, between about 1% to about 2% of the megakaryocyte-derived extracellular vesicles comprise a lipid bilayer membrane comprising CD61. In embodiments, between about 50% to about 99% of the megakaryocyte-derived extracellular vesicles comprise a lipid bilayer membrane comprising CD61. In embodiments, between about 75% to about 99% of the megakaryocyte-derived extracellular vesicles comprise a lipid bilayer membrane comprising CD61. In embodiments, between about 80% to about 99% of the megakaryocyte-derived extracellular vesicles comprise a lipid bilayer membrane comprising CD61. In embodiments, between about 85% to about 95% of the megakaryocyte-derived extracellular vesicles comprise a lipid bilayer membrane comprising CD61. In embodiments, between about 90% to about 99% of the megakaryocyte-derived extracellular vesicles comprise a lipid bilayer membrane comprising CD61. In embodiments, between about 95% to about 99% of the megakaryocyte-derived extracellular vesicles comprise a lipid bilayer membrane comprising CD61.

In embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD61.

In embodiments, the megakaryocyte-derived extracellular vesicles are characterized by a higher expression and/or presence of CD61 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD61 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD61 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD61 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about an 8-fold or about a 2-fold to about a 4-fold greater amount of CD61 than platelet free plasma (PFP) MkEVs. In embodiments, the megakaryocyte-derived extracellular vesicles have about a 2-fold, about a 3-fold, or about a 4-fold greater amount of CD61 than platelet free plasma (PFP) MkEVs. In embodiments, the megakaryocyte-derived extracellular vesicles have about a 1.1-fold to about a 2-fold lower amount of CD61 than platelet derived extracellular vesicles (PLT EVs). In embodiments, the megakaryocyte-derived extracellular vesicles have about a 1.1-fold or about a 1.2-fold lower amount of CD61 than platelet derived extracellular vesicles (PLT EVs). In embodiments, the megakaryocyte-derived extracellular vesicles have an amount of CD61 that is substantially the same as platelet derived extracellular vesicles (PLT EVs).

In embodiments, greater than about 50% of the megakaryocyte-derived extracellular vesicles comprise a lipid bilayer membrane comprising CD54. In embodiments, greater than about 40% of the megakaryocyte-derived extracellular vesicles comprise a lipid bilayer membrane comprising CD54. In embodiments, greater than about 60% of the megakaryocyte-derived extracellular vesicles comprise a lipid bilayer membrane comprising CD54. In embodiments, greater than about 70% of the megakaryocyte-derived extracellular vesicles comprise a lipid bilayer membrane comprising CD4. In embodiments, greater than about 80% of the megakaryocyte-derived extracellular vesicles comprise a lipid bilayer membrane comprising CD54. In embodiments, greater than about 90% of the megakaryocyte-derived extracellular vesicles comprise a lipid bilayer membrane comprising CD54. In embodiments, greater than about 95% of the megakaryocyte-derived extracellular vesicles comprise a lipid bilayer membrane comprising CD54. In embodiments, greater than about 99% of the megakaryocyte-derived extracellular vesicles comprise a lipid bilayer membrane comprising CD54.

In embodiments, about 50% or less of the megakaryocyte-derived extracellular vesicles comprise a lipid bilayer membrane comprising CD54. In embodiments, about 40% or less of the megakaryocyte-derived extracellular vesicles comprise a lipid bilayer membrane comprising CD54. In embodiments, about 60% or less of the megakaryocyte-derived extracellular vesicles comprise a lipid bilayer membrane comprising CD54. In embodiments, about 70% or less of the megakaryocyte-derived extracellular vesicles comprise a lipid bilayer membrane comprising CD54. In embodiments, about 80% or less of the megakaryocyte-derived extracellular vesicles comprise a lipid bilayer membrane comprising CD54. In embodiments, about 90% or less of the megakaryocyte-derived extracellular vesicles comprise a lipid bilayer membrane comprising CD54. In embodiments, about 95% or less of the megakaryocyte-derived extracellular vesicles comprise a lipid bilayer membrane comprising CD54. In embodiments, about 99% or less of the megakaryocyte-derived extracellular vesicles comprise a lipid bilayer membrane comprising CD54.

In embodiments, less than about 50% of the megakaryocyte-derived extracellular vesicles comprise a lipid bilayer membrane comprising CD54. In embodiments, less than about 40% of the megakaryocyte-derived extracellular vesicles comprise a lipid bilayer membrane comprising CD54. In embodiments, less than about 30% of the megakaryocyte-derived extracellular vesicles comprise a lipid bilayer membrane comprising CD54. In embodiments, less than about 25% of the megakaryocyte-derived extracellular vesicles comprise a lipid bilayer membrane comprising CD54. In embodiments, less than about 20% of the megakaryocyte-derived extracellular vesicles comprise a lipid bilayer membrane comprising CD54. In embodiments, less than about 15% of the megakaryocyte-derived extracellular vesicles comprise a lipid bilayer membrane comprising CD54. In embodiments, less than about 10% of the megakaryocyte-derived extracellular vesicles comprise a lipid bilayer membrane comprising CD54. In embodiments, less than about 5% of the megakaryocyte-derived extracellular vesicles comprise a lipid bilayer membrane comprising CD54. In embodiments, less than about 1% of the megakaryocyte-derived extracellular vesicles comprise a lipid bilayer membrane comprising CD54.

In embodiments, between about 1% to about 99% of the megakaryocyte-derived extracellular vesicles comprise a lipid bilayer membrane comprising CD54. In embodiments, between about 1% to about 50% of the megakaryocyte-derived extracellular vesicles comprise a lipid bilayer membrane comprising CD54. In embodiments, between about 1% to about 25% of the megakaryocyte-derived extracellular vesicles comprise a lipid bilayer membrane comprising CD54. In embodiments, between about 1% to about 10% of the megakaryocyte-derived extracellular vesicles comprise a lipid bilayer membrane comprising CD54. In embodiments, between about 1% to about 5% of the megakaryocyte-derived extracellular vesicles comprise a lipid bilayer membrane comprising CD54. In embodiments, between about 1% to about 2% of the megakaryocyte-derived extracellular vesicles comprise a lipid bilayer membrane comprising CD54. In embodiments, between about 50% to about 99% of the megakaryocyte-derived extracellular vesicles comprise a lipid bilayer membrane comprising CD54. In embodiments, between about 75% to about 99% of the megakaryocyte-derived extracellular vesicles comprise a lipid bilayer membrane comprising CD54. In embodiments, between about 90% to about 99% of the megakaryocyte-derived extracellular vesicles comprise a lipid bilayer membrane comprising CD54. In embodiments, between about 95% to about 99% of the megakaryocyte-derived extracellular vesicles comprise a lipid bilayer membrane comprising CD54.

In embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD54.

In embodiments, the megakaryocyte-derived extracellular vesicles are characterized by a higher expression and/or presence of CD54 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD54 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about a 10-fold or about a 2-fold to about a 4-fold greater amount of CD54 than platelet free plasma (PFP) MkEVs. In embodiments, the megakaryocyte-derived extracellular vesicles have about a 3-fold greater amount of CD54 than platelet free plasma (PFP) MkEVs. In embodiments, the megakaryocyte-derived extracellular vesicles have about a 1.1-fold to about a 4-fold or about a 1.1-fold to about a 2-fold greater amount of CD54 than platelet derived extracellular vesicles (PLT EVs). In embodiments, the megakaryocyte-derived extracellular vesicles have about a 1.5-fold greater amount of CD54 than platelet derived extracellular vesicles (PLT EVs).

In embodiments, the megakaryocyte-derived extracellular vesicles are characterized by a lower expression and/or presence of CD54 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD54 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, greater than about 50% of the megakaryocyte-derived extracellular vesicles comprise a lipid bilayer membrane comprising CD18. In embodiments, greater than about 40% of the megakaryocyte-derived extracellular vesicles comprise a lipid bilayer membrane comprising CD18. In embodiments, greater than about 60% of the megakaryocyte-derived extracellular vesicles comprise a lipid bilayer membrane comprising CD18. In embodiments, greater than about 70% of the megakaryocyte-derived extracellular vesicles comprise a lipid bilayer membrane comprising CD18. In embodiments, greater than about 80% of the megakaryocyte-derived extracellular vesicles comprise a lipid bilayer membrane comprising CD18. In embodiments, greater than about 90% of the megakaryocyte-derived extracellular vesicles comprise a lipid bilayer membrane comprising CD18. In embodiments, greater than about 95% of the megakaryocyte-derived extracellular vesicles comprise a lipid bilayer membrane comprising CD18. In embodiments, greater than about 99% of the megakaryocyte-derived extracellular vesicles comprise a lipid bilayer membrane comprising CD18.

In embodiments, about 50% or less of the megakaryocyte-derived extracellular vesicles comprise a lipid bilayer membrane comprising CD18. In embodiments, about 40% or less of the megakaryocyte-derived extracellular vesicles comprise a lipid bilayer membrane comprising CD18. In embodiments, about 60% or less of the megakaryocyte-derived extracellular vesicles comprise a lipid bilayer membrane comprising CD18. In embodiments, about 70% or less of the megakaryocyte-derived extracellular vesicles comprise a lipid bilayer membrane comprising CD18. In embodiments, about 80% or less of the megakaryocyte-derived extracellular vesicles comprise a lipid bilayer membrane comprising CD18. In embodiments, about 90% or less of the megakaryocyte-derived extracellular vesicles comprise a lipid bilayer membrane comprising CD18. In embodiments, about 95% or less of the megakaryocyte-derived extracellular vesicles comprise a lipid bilayer membrane comprising CD18. In embodiments, about 99% or less of the megakaryocyte-derived extracellular vesicles comprise a lipid bilayer membrane comprising CD18.

In embodiments, less than about 50% of the megakaryocyte-derived extracellular vesicles comprise a lipid bilayer membrane comprising CD18. In embodiments, less than about 40% of the megakaryocyte-derived extracellular vesicles comprise a lipid bilayer membrane comprising CD18. In embodiments, less than about 30% of the megakaryocyte-derived extracellular vesicles comprise a lipid bilayer membrane comprising CD18. In embodiments, less than about 25% of the megakaryocyte-derived extracellular vesicles comprise a lipid bilayer membrane comprising CD18. In embodiments, less than about 20% of the megakaryocyte-derived extracellular vesicles comprise a lipid bilayer membrane comprising CD18. In embodiments, less than about 15% of the megakaryocyte-derived extracellular vesicles comprise a lipid bilayer membrane comprising CD18. In embodiments, less than about 10% of the megakaryocyte-derived extracellular vesicles comprise a lipid bilayer membrane comprising CD18. In embodiments, less than about 5% of the megakaryocyte-derived extracellular vesicles comprise a lipid bilayer membrane comprising CD18. In embodiments, less than about 1% of the megakaryocyte-derived extracellular vesicles comprise a lipid bilayer membrane comprising CD18.

In embodiments, between about 1% to about 99% of the megakaryocyte-derived extracellular vesicles comprise a lipid bilayer membrane comprising CD18. In embodiments, between about 1% to about 50% of the megakaryocyte-derived extracellular vesicles comprise a lipid bilayer membrane comprising CD18. In embodiments, between about 1% to about 25% of the megakaryocyte-derived extracellular vesicles comprise a lipid bilayer membrane comprising CD18. In embodiments, between about 1% to about 10% of the megakaryocyte-derived extracellular vesicles comprise a lipid bilayer membrane comprising CD18. In embodiments, between about 1% to about 5% of the megakaryocyte-derived extracellular vesicles comprise a lipid bilayer membrane comprising CD18. In embodiments, between about 1% to about 2% of the megakaryocyte-derived extracellular vesicles comprise a lipid bilayer membrane comprising CD18. In embodiments, between about 50% to about 99% of the megakaryocyte-derived extracellular vesicles comprise a lipid bilayer membrane comprising CD18. In embodiments, between about 75% to about 99% of the megakaryocyte-derived extracellular vesicles comprise a lipid bilayer membrane comprising CD18. In embodiments, between about 90% to about 99% of the megakaryocyte-derived extracellular vesicles comprise a lipid bilayer membrane comprising CD18. In embodiments, between about 95% to about 99% of the megakaryocyte-derived extracellular vesicles comprise a lipid bilayer membrane comprising CD18.

In embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD18.

In embodiments, the megakaryocyte-derived extracellular vesicles are characterized by a higher expression and/or presence of CD18 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD18 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about a 10-fold, an 8-fold to about a 64-fold, or about a 16-fold to about a 32-fold, or about a 16-fold to about a 24-fold greater amount of CD18 than platelet free plasma (PFP) MkEVs. In embodiments, the megakaryocyte-derived extracellular vesicles have about a 20-fold greater amount of CD18 than platelet free plasma (PFP) MkEVs. In embodiments, the megakaryocyte-derived extracellular vesicles have about a 1.1-fold to about a 4-fold or about a 1.1-fold to about a 2-fold greater amount of CD18 than platelet derived extracellular vesicles (PLT EVs). In embodiments, the megakaryocyte-derived extracellular vesicles have about a 1.5-fold greater amount of CD18 than platelet derived extracellular vesicles (PLT EVs).

In embodiments, the megakaryocyte-derived extracellular vesicles are characterized by a lower expression and/or presence of CD18 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD18 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, greater than about 50% of the megakaryocyte-derived extracellular vesicles comprise a lipid bilayer membrane comprising CD43. In embodiments, greater than about 40% of the megakaryocyte-derived extracellular vesicles comprise a lipid bilayer membrane comprising CD43. In embodiments, greater than about 60% of the megakaryocyte-derived extracellular vesicles comprise a lipid bilayer membrane comprising CD43. In embodiments, greater than about 70% of the megakaryocyte-derived extracellular vesicles comprise a lipid bilayer membrane comprising CD43. In embodiments, greater than about 80% of the megakaryocyte-derived extracellular vesicles comprise a lipid bilayer membrane comprising CD43. In embodiments, greater than about 90% of the megakaryocyte-derived extracellular vesicles comprise a lipid bilayer membrane comprising CD43. In embodiments, greater than about 95% of the megakaryocyte-derived extracellular vesicles comprise a lipid bilayer membrane comprising CD43. In embodiments, greater than about 99% of the megakaryocyte-derived extracellular vesicles comprise a lipid bilayer membrane comprising CD43.

In embodiments, about 50% or less of the megakaryocyte-derived extracellular vesicles comprise a lipid bilayer membrane comprising CD43. In embodiments, about 40% or less of the megakaryocyte-derived extracellular vesicles comprise a lipid bilayer membrane comprising CD43. In embodiments, about 60% or less of the megakaryocyte-derived extracellular vesicles comprise a lipid bilayer membrane comprising CD43. In embodiments, about 70% or less of the megakaryocyte-derived extracellular vesicles comprise a lipid bilayer membrane comprising CD43. In embodiments, about 80% or less of the megakaryocyte-derived extracellular vesicles comprise a lipid bilayer membrane comprising CD43. In embodiments, about 90% or less of the megakaryocyte-derived extracellular vesicles comprise a lipid bilayer membrane comprising CD43. In embodiments, about 95% or less of the megakaryocyte-derived extracellular vesicles comprise a lipid bilayer membrane comprising CD43. In embodiments, about 99% or less of the megakaryocyte-derived extracellular vesicles comprise a lipid bilayer membrane comprising CD43.

In embodiments, less than about 50% of the megakaryocyte-derived extracellular vesicles comprise a lipid bilayer membrane comprising CD43. In embodiments, less than about 40% of the megakaryocyte-derived extracellular vesicles comprise a lipid bilayer membrane comprising CD43. In embodiments, less than about 30% of the megakaryocyte-derived extracellular vesicles comprise a lipid bilayer membrane comprising CD43. In embodiments, less than about 25% of the megakaryocyte-derived extracellular vesicles comprise a lipid bilayer membrane comprising CD43. In embodiments, less than about 20% of the megakaryocyte-derived extracellular vesicles comprise a lipid bilayer membrane comprising CD43. In embodiments, less than about 15% of the megakaryocyte-derived extracellular vesicles comprise a lipid bilayer membrane comprising CD43. In embodiments, less than about 10% of the megakaryocyte-derived extracellular vesicles comprise a lipid bilayer membrane comprising CD43. In embodiments, less than about 5% of the megakaryocyte-derived extracellular vesicles comprise a lipid bilayer membrane comprising CD43. In embodiments, less than about 1% of the megakaryocyte-derived extracellular vesicles comprise a lipid bilayer membrane comprising CD43.

In embodiments, between about 1% to about 99% of the megakaryocyte-derived extracellular vesicles comprise a lipid bilayer membrane comprising CD43. In embodiments, between about 1% to about 50% of the megakaryocyte-derived extracellular vesicles comprise a lipid bilayer membrane comprising CD43. In embodiments, between about 1% to about 25% of the megakaryocyte-derived extracellular vesicles comprise a lipid bilayer membrane comprising CD43. In embodiments, between about 1% to about 10% of the megakaryocyte-derived extracellular vesicles comprise a lipid bilayer membrane comprising CD43. In embodiments, between about 1% to about 5% of the megakaryocyte-derived extracellular vesicles comprise a lipid bilayer membrane comprising CD43. In embodiments, between about 1% to about 2% of the megakaryocyte-derived extracellular vesicles comprise a lipid bilayer membrane comprising CD43. In embodiments, between about 50% to about 99% of the megakaryocyte-derived extracellular vesicles comprise a lipid bilayer membrane comprising CD43. In embodiments, between about 75% to about 99% of the megakaryocyte-derived extracellular vesicles comprise a lipid bilayer membrane comprising CD43. In embodiments, between about 90% to about 99% of the megakaryocyte-derived extracellular vesicles comprise a lipid bilayer membrane comprising CD43. In embodiments, between about 95% to about 99% of the megakaryocyte-derived extracellular vesicles comprise a lipid bilayer membrane comprising CD43.

In embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD43.

In embodiments, the megakaryocyte-derived extracellular vesicles are characterized by a higher expression and/or presence of CD43 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD43 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about an 4-fold to about a 64-fold, or about a 8-fold to about a 32-fold, or about a 8-fold to about a 16-fold greater amount of CD43 than platelet free plasma (PFP) MkEVs. In embodiments, the megakaryocyte-derived extracellular vesicles have about a 10-fold or about a 12-fold greater amount of CD43 than platelet free plasma (PFP) MkEVs. In embodiments, the megakaryocyte-derived extracellular vesicles have about a 1.5-fold to about an 8-fold or about a 2-fold to about a 4-fold greater amount of CD43 than platelet derived extracellular vesicles (PLT EVs). In embodiments, the megakaryocyte-derived extracellular vesicles have about a 3-fold or about a 4-fold greater amount of CD43 than platelet derived extracellular vesicles (PLT EVs).

In embodiments, the megakaryocyte-derived extracellular vesicles are characterized by a lower expression and/or presence of CD43 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD43 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, greater than about 50% of the megakaryocyte-derived extracellular vesicles comprise a lipid bilayer membrane comprising CD11b. In embodiments, greater than about 40% of the megakaryocyte-derived extracellular vesicles comprise a lipid bilayer membrane comprising CD11b. In embodiments, greater than about 60% of the megakaryocyte-derived extracellular vesicles comprise a lipid bilayer membrane comprising CD11b. In embodiments, greater than about 70% of the megakaryocyte-derived extracellular vesicles comprise a lipid bilayer membrane comprising CD11b. In embodiments, greater than about 80% of the megakaryocyte-derived extracellular vesicles comprise a lipid bilayer membrane comprising CD11b. In embodiments, greater than about 90% of the megakaryocyte-derived extracellular vesicles comprise a lipid bilayer membrane comprising CD11b. In embodiments, greater than about 95% of the megakaryocyte-derived extracellular vesicles comprise a lipid bilayer membrane comprising CD11 b. In embodiments, greater than about 99% of the megakaryocyte-derived extracellular vesicles comprise a lipid bilayer membrane comprising CD11b.

In embodiments, about 50% or less of the megakaryocyte-derived extracellular vesicles comprise a lipid bilayer membrane comprising CD11b. In embodiments, about 40% or less of the megakaryocyte-derived extracellular vesicles comprise a lipid bilayer membrane comprising CD11b. In embodiments, about 60% or less of the megakaryocyte-derived extracellular vesicles comprise a lipid bilayer membrane comprising CD11b. In embodiments, about 70% or less of the megakaryocyte-derived extracellular vesicles comprise a lipid bilayer membrane comprising CD11b. In embodiments, about 80% or less of the megakaryocyte-derived extracellular vesicles comprise a lipid bilayer membrane comprising CD11 b. In embodiments, about 90% or less of the megakaryocyte-derived extracellular vesicles comprise a lipid bilayer membrane comprising CD11b. In embodiments, about 95% or less of the megakaryocyte-derived extracellular vesicles comprise a lipid bilayer membrane comprising CD11b. In embodiments, about 99% or less of the megakaryocyte-derived extracellular vesicles comprise a lipid bilayer membrane comprising CD11 b.

In embodiments, less than about 50% of the megakaryocyte-derived extracellular vesicles comprise a lipid bilayer membrane comprising CD11b. In embodiments, less than about 40% of the megakaryocyte-derived extracellular vesicles comprise a lipid bilayer membrane comprising CD11 b. In embodiments, less than about 30% of the megakaryocyte-derived extracellular vesicles comprise a lipid bilayer membrane comprising CD11b. In embodiments, less than about 25% of the megakaryocyte-derived extracellular vesicles comprise a lipid bilayer membrane comprising CD11b. In embodiments, less than about 20% of the megakaryocyte-derived extracellular vesicles comprise a lipid bilayer membrane comprising CD11b. In embodiments, less than about 15% of the megakaryocyte-derived extracellular vesicles comprise a lipid bilayer membrane comprising CD11 b. In embodiments, less than about 10% of the megakaryocyte-derived extracellular vesicles comprise a lipid bilayer membrane comprising CD11b. In embodiments, less than about 5% of the megakaryocyte-derived extracellular vesicles comprise a lipid bilayer membrane comprising CD11b. In embodiments, less than about 1% of the megakaryocyte-derived extracellular vesicles comprise a lipid bilayer membrane comprising CD11b.

In embodiments, between about 1% to about 99% of the megakaryocyte-derived extracellular vesicles comprise a lipid bilayer membrane comprising CD11b. In embodiments, between about 1% to about 50% of the megakaryocyte-derived extracellular vesicles comprise a lipid bilayer membrane comprising CD11b. In embodiments, between about 1% to about 25% of the megakaryocyte-derived extracellular vesicles comprise a lipid bilayer membrane comprising CD11b. In embodiments, between about 1% to about 10% of the megakaryocyte-derived extracellular vesicles comprise a lipid bilayer membrane comprising CD11b. In embodiments, between about 1% to about 5% of the megakaryocyte-derived extracellular vesicles comprise a lipid bilayer membrane comprising CD11b. In embodiments, between about 1% to about 2% of the megakaryocyte-derived extracellular vesicles comprise a lipid bilayer membrane comprising CD11b. In embodiments, between about 50% to about 99% of the megakaryocyte-derived extracellular vesicles comprise a lipid bilayer membrane comprising CD11 b. In embodiments, between about 75% to about 99% of the megakaryocyte-derived extracellular vesicles comprise a lipid bilayer membrane comprising CD11 b. In embodiments, between about 90% to about 99% of the megakaryocyte-derived extracellular vesicles comprise a lipid bilayer membrane comprising CD11b. In embodiments, between about 95% to about 99% of the megakaryocyte-derived extracellular vesicles comprise a lipid bilayer membrane comprising CD11b.

In embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD11 b.

In embodiments, the megakaryocyte-derived extracellular vesicles are characterized by a higher expression and/or presence of CD11 b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD11 b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about an 8-fold, or about a 2-fold to about a 4-fold greater amount of CD11b than platelet free plasma (PFP) MkEVs. In embodiments, the megakaryocyte-derived extracellular vesicles have about a 3-fold greater amount of CD11b than platelet free plasma (PFP) MkEVs. In embodiments, the megakaryocyte-derived extracellular vesicles have about a 1.1-fold to about a 4-fold, or about a 1.1-fold to about a 2-fold greater amount of CD11b than platelet derived extracellular vesicles (PLT EVs). In embodiments, the megakaryocyte-derived extracellular vesicles have about a 1.5-fold greater amount of CD11b than platelet derived extracellular vesicles (PLT EVs).

In embodiments, the megakaryocyte-derived extracellular vesicles are characterized by a higher expression and/or presence of CD11b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD11b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD11 b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD11 b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, greater than about 50% of the megakaryocyte-derived extracellular vesicles comprise a lipid bilayer membrane comprising CD21. In embodiments, greater than about 40% of the megakaryocyte-derived extracellular vesicles comprise a lipid bilayer membrane comprising CD21. In embodiments, greater than about 60% of the megakaryocyte-derived extracellular vesicles comprise a lipid bilayer membrane comprising CD21. In embodiments, greater than about 70% of the megakaryocyte-derived extracellular vesicles comprise a lipid bilayer membrane comprising CD21. In embodiments, greater than about 80% of the megakaryocyte-derived extracellular vesicles comprise a lipid bilayer membrane comprising CD21. In embodiments, greater than about 90% of the megakaryocyte-derived extracellular vesicles comprise a lipid bilayer membrane comprising CD21. In embodiments, greater than about 95% of the megakaryocyte-derived extracellular vesicles comprise a lipid bilayer membrane comprising CD21. In embodiments, greater than about 99% of the megakaryocyte-derived extracellular vesicles comprise a lipid bilayer membrane comprising CD21.

In embodiments, about 50% or less of the megakaryocyte-derived extracellular vesicles comprise a lipid bilayer membrane comprising CD21. In embodiments, about 40% or less of the megakaryocyte-derived extracellular vesicles comprise a lipid bilayer membrane comprising CD21. In embodiments, about 60% or less of the megakaryocyte-derived extracellular vesicles comprise a lipid bilayer membrane comprising CD21. In embodiments, about 70% or less of the megakaryocyte-derived extracellular vesicles comprise a lipid bilayer membrane comprising CD21. In embodiments, about 80% or less of the megakaryocyte-derived extracellular vesicles comprise a lipid bilayer membrane comprising CD21. In embodiments, about 90% or less of the megakaryocyte-derived extracellular vesicles comprise a lipid bilayer membrane comprising CD21. In embodiments, about 95% or less of the megakaryocyte-derived extracellular vesicles comprise a lipid bilayer membrane comprising CD21. In embodiments, about 99% or less of the megakaryocyte-derived extracellular vesicles comprise a lipid bilayer membrane comprising CD21.

In embodiments, less than about 50% of the megakaryocyte-derived extracellular vesicles comprise a lipid bilayer membrane comprising CD21. In embodiments, less than about 40% of the megakaryocyte-derived extracellular vesicles comprise a lipid bilayer membrane comprising CD21. In embodiments, less than about 30% of the megakaryocyte-derived extracellular vesicles comprise a lipid bilayer membrane comprising CD21. In embodiments, less than about 25% of the megakaryocyte-derived extracellular vesicles comprise a lipid bilayer membrane comprising CD21. In embodiments, less than about 20% of the megakaryocyte-derived extracellular vesicles comprise a lipid bilayer membrane comprising CD21. In embodiments, less than about 15% of the megakaryocyte-derived extracellular vesicles comprise a lipid bilayer membrane comprising CD21. In embodiments, less than about 10% of the megakaryocyte-derived extracellular vesicles comprise a lipid bilayer membrane comprising CD21. In embodiments, less than about 5% of the megakaryocyte-derived extracellular vesicles comprise a lipid bilayer membrane comprising CD21. In embodiments, less than about 1% of the megakaryocyte-derived extracellular vesicles comprise a lipid bilayer membrane comprising CD21.

In embodiments, between about 1% to about 99% of the megakaryocyte-derived extracellular vesicles comprise a lipid bilayer membrane comprising CD21. In embodiments, between about 1% to about 50% of the megakaryocyte-derived extracellular vesicles comprise a lipid bilayer membrane comprising CD21. In embodiments, between about 1% to about 25% of the megakaryocyte-derived extracellular vesicles comprise a lipid bilayer membrane comprising CD21. In embodiments, between about 1% to about 10% of the megakaryocyte-derived extracellular vesicles comprise a lipid bilayer membrane comprising CD21. In embodiments, between about 1% to about 5% of the megakaryocyte-derived extracellular vesicles comprise a lipid bilayer membrane comprising CD21. In embodiments, between about 1% to about 2% of the megakaryocyte-derived extracellular vesicles comprise a lipid bilayer membrane comprising CD21. In embodiments, between about 50% to about 99% of the megakaryocyte-derived extracellular vesicles comprise a lipid bilayer membrane comprising CD21. In embodiments, between about 75% to about 99% of the megakaryocyte-derived extracellular vesicles comprise a lipid bilayer membrane comprising CD21. In embodiments, between about 90% to about 99% of the megakaryocyte-derived extracellular vesicles comprise a lipid bilayer membrane comprising CD21. In embodiments, between about 95% to about 99% of the megakaryocyte-derived extracellular vesicles comprise a lipid bilayer membrane comprising CD21.

In embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD21.

In embodiments, the megakaryocyte-derived extracellular vesicles are characterized by a higher expression and/or presence of CD21 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about a 64-fold, about a 4-fold to about a 32-fold, or about an 8-fold to about a 16-fold greater amount of CD21 than platelet free plasma (PFP) MkEVs. In embodiments, the megakaryocyte-derived extracellular vesicles have about a 10-fold or about a 12-fold greater amount of CD21 than platelet free plasma (PFP) MkEVs. In embodiments, the megakaryocyte-derived extracellular vesicles have about a 2-fold to about an 8-fold, or about a 4-fold to about an 8-fold greater amount of CD21 than platelet derived extracellular vesicles (PLT EVs). In embodiments, the megakaryocyte-derived extracellular vesicles have about a 4-fold or about a 5-fold greater amount of CD21 than platelet derived extracellular vesicles (PLT EVs).

In embodiments, the megakaryocyte-derived extracellular vesicles are characterized by a lower expression and/or presence of CD21 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD21 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, greater than about 50% of the megakaryocyte-derived extracellular vesicles comprise a lipid bilayer membrane comprising CD51. In embodiments, greater than about 40% of the megakaryocyte-derived extracellular vesicles comprise a lipid bilayer membrane comprising CD51. In embodiments, greater than about 60% of the megakaryocyte-derived extracellular vesicles comprise a lipid bilayer membrane comprising CD51. In embodiments, greater than about 70% of the megakaryocyte-derived extracellular vesicles comprise a lipid bilayer membrane comprising CD51. In embodiments, greater than about 80% of the megakaryocyte-derived extracellular vesicles comprise a lipid bilayer membrane comprising CD51. In embodiments, greater than about 90% of the megakaryocyte-derived extracellular vesicles comprise a lipid bilayer membrane comprising CD51. In embodiments, greater than about 95% of the megakaryocyte-derived extracellular vesicles comprise a lipid bilayer membrane comprising CD51. In embodiments, greater than about 99% of the megakaryocyte-derived extracellular vesicles comprise a lipid bilayer membrane comprising CD51.

In embodiments, about 50% or less of the megakaryocyte-derived extracellular vesicles comprise a lipid bilayer membrane comprising CD51. In embodiments, about 40% or less of the megakaryocyte-derived extracellular vesicles comprise a lipid bilayer membrane comprising CD51. In embodiments, about 60% or less of the megakaryocyte-derived extracellular vesicles comprise a lipid bilayer membrane comprising CD51. In embodiments, about 70% or less of the megakaryocyte-derived extracellular vesicles comprise a lipid bilayer membrane comprising CD51. In embodiments, about 80% or less of the megakaryocyte-derived extracellular vesicles comprise a lipid bilayer membrane comprising CD51. In embodiments, about 90% or less of the megakaryocyte-derived extracellular vesicles comprise a lipid bilayer membrane comprising CD51. In embodiments, about 95% or less of the megakaryocyte-derived extracellular vesicles comprise a lipid bilayer membrane comprising CD51. In embodiments, about 99% or less of the megakaryocyte-derived extracellular vesicles comprise a lipid bilayer membrane comprising CD51.

In embodiments, less than about 50% of the megakaryocyte-derived extracellular vesicles comprise a lipid bilayer membrane comprising CD51. In embodiments, less than about 40% of the megakaryocyte-derived extracellular vesicles comprise a lipid bilayer membrane comprising CD51. In embodiments, less than about 30% of the megakaryocyte-derived extracellular vesicles comprise a lipid bilayer membrane comprising CD51. In embodiments, less than about 25% of the megakaryocyte-derived extracellular vesicles comprise a lipid bilayer membrane comprising CD51. In embodiments, less than about 20% of the megakaryocyte-derived extracellular vesicles comprise a lipid bilayer membrane comprising CD51. In embodiments, less than about 15% of the megakaryocyte-derived extracellular vesicles comprise a lipid bilayer membrane comprising CD51. In embodiments, less than about 10% of the megakaryocyte-derived extracellular vesicles comprise a lipid bilayer membrane comprising CD51. In embodiments, less than about 5% of the megakaryocyte-derived extracellular vesicles comprise a lipid bilayer membrane comprising CD51. In embodiments, less than about 1% of the megakaryocyte-derived extracellular vesicles comprise a lipid bilayer membrane comprising CD51.

In embodiments, between about 1% to about 99% of the megakaryocyte-derived extracellular vesicles comprise a lipid bilayer membrane comprising CD51. In embodiments, between about 1% to about 50% of the megakaryocyte-derived extracellular vesicles comprise a lipid bilayer membrane comprising CD51. In embodiments, between about 1% to about 25% of the megakaryocyte-derived extracellular vesicles comprise a lipid bilayer membrane comprising CD51. In embodiments, between about 1% to about 10% of the megakaryocyte-derived extracellular vesicles comprise a lipid bilayer membrane comprising CD51. In embodiments, between about 1% to about 5% of the megakaryocyte-derived extracellular vesicles comprise a lipid bilayer membrane comprising CD51. In embodiments, between about 1% to about 2% of the megakaryocyte-derived extracellular vesicles comprise a lipid bilayer membrane comprising CD51. In embodiments, between about 50% to about 99% of the megakaryocyte-derived extracellular vesicles comprise a lipid bilayer membrane comprising CD51. In embodiments, between about 75% to about 99% of the megakaryocyte-derived extracellular vesicles comprise a lipid bilayer membrane comprising CD51. In embodiments, between about 90% to about 99% of the megakaryocyte-derived extracellular vesicles comprise a lipid bilayer membrane comprising CD51. In embodiments, between about 95% to about 99% of the megakaryocyte-derived extracellular vesicles comprise a lipid bilayer membrane comprising CD51.

In embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD51.

In embodiments, the megakaryocyte-derived extracellular vesicles are characterized by a higher expression and/or presence of CD51 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD51 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD51 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD51 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 1.1-fold to about a 4-fold, or about a 1.1-fold to about a 2-fold lower amount of CD51 than platelet free plasma (PFP) MkEVs. In embodiments, the megakaryocyte-derived extracellular vesicles have about a 1.5-fold lower amount of CD51 than platelet free plasma (PFP) MkEVs. In embodiments, the megakaryocyte-derived extracellular vesicles have about a 1.1-fold to about a 4-fold, or about a 1.1-fold to about a 2-fold lower amount of CD51 than platelet derived extracellular vesicles (PLT EVs). In embodiments, the megakaryocyte-derived extracellular vesicles have about a 1.5-fold lower amount of CD51 than platelet derived extracellular vesicles (PLT EVs).

In embodiments, greater than about 50% of the megakaryocyte-derived extracellular vesicles comprise a lipid bilayer membrane comprising CLEC-2. In embodiments, greater than about 40% of the megakaryocyte-derived extracellular vesicles comprise a lipid bilayer membrane comprising CLEC-2. In embodiments, greater than about 60% of the megakaryocyte-derived extracellular vesicles comprise a lipid bilayer membrane comprising CLEC-2. In embodiments, greater than about 70% of the megakaryocyte-derived extracellular vesicles comprise a lipid bilayer membrane comprising CLEC-2. In embodiments, greater than about 80% of the megakaryocyte-derived extracellular vesicles comprise a lipid bilayer membrane comprising CLEC-2. In embodiments, greater than about 90% of the megakaryocyte-derived extracellular vesicles comprise a lipid bilayer membrane comprising CLEC-2. In embodiments, greater than about 95% of the megakaryocyte-derived extracellular vesicles comprise a lipid bilayer membrane comprising CLEC-2. In embodiments, greater than about 99% of the megakaryocyte-derived extracellular vesicles comprise a lipid bilayer membrane comprising CLEC-2.

In embodiments, about 50% or less of the megakaryocyte-derived extracellular vesicles comprise a lipid bilayer membrane comprising CLEC-2. In embodiments, about 40% or less of the megakaryocyte-derived extracellular vesicles comprise a lipid bilayer membrane comprising CLEC-2. In embodiments, about 60% or less of the megakaryocyte-derived extracellular vesicles comprise a lipid bilayer membrane comprising CLEC-2. In embodiments, about 70% or less of the megakaryocyte-derived extracellular vesicles comprise a lipid bilayer membrane comprising CLEC-2. In embodiments, about 80% or less of the megakaryocyte-derived extracellular vesicles comprise a lipid bilayer membrane comprising CLEC-2. In embodiments, about 90% or less of the megakaryocyte-derived extracellular vesicles comprise a lipid bilayer membrane comprising CLEC-2. In embodiments, about 95% or less of the megakaryocyte-derived extracellular vesicles comprise a lipid bilayer membrane comprising CLEC-2. In embodiments, about 99% or less of the megakaryocyte-derived extracellular vesicles comprise a lipid bilayer membrane comprising CLEC-2.

In embodiments, less than about 50% of the megakaryocyte-derived extracellular vesicles comprise a lipid bilayer membrane comprising CLEC-2. In embodiments, less than about 40% of the megakaryocyte-derived extracellular vesicles comprise a lipid bilayer membrane comprising CLEC-2. In embodiments, less than about 30% of the megakaryocyte-derived extracellular vesicles comprise a lipid bilayer membrane comprising CLEC-2. In embodiments, less than about 25% of the megakaryocyte-derived extracellular vesicles comprise a lipid bilayer membrane comprising CLEC-2. In embodiments, less than about 20% of the megakaryocyte-derived extracellular vesicles comprise a lipid bilayer membrane comprising CLEC-2. In embodiments, less than about 15% of the megakaryocyte-derived extracellular vesicles comprise a lipid bilayer membrane comprising CLEC-2. In embodiments, less than about 10% of the megakaryocyte-derived extracellular vesicles comprise a lipid bilayer membrane comprising CLEC-2. In embodiments, less than about 5% of the megakaryocyte-derived extracellular vesicles comprise a lipid bilayer membrane comprising CLEC-2. In embodiments, less than about 1% of the megakaryocyte-derived extracellular vesicles comprise a lipid bilayer membrane comprising CLEC-2.

In embodiments, between about 1% to about 99% of the megakaryocyte-derived extracellular vesicles comprise a lipid bilayer membrane comprising CLEC-2. In embodiments, between about 1% to about 50% of the megakaryocyte-derived extracellular vesicles comprise a lipid bilayer membrane comprising CLEC-2. In embodiments, between about 1% to about 25% of the megakaryocyte-derived extracellular vesicles comprise a lipid bilayer membrane comprising CLEC-2. In embodiments, between about 1% to about 10% of the megakaryocyte-derived extracellular vesicles comprise a lipid bilayer membrane comprising CLEC-2. In embodiments, between about 1% to about 5% of the megakaryocyte-derived extracellular vesicles comprise a lipid bilayer membrane comprising CLEC-2. In embodiments, between about 1% to about 2% of the megakaryocyte-derived extracellular vesicles comprise a lipid bilayer membrane comprising CLEC-2. In embodiments, between about 50% to about 99% of the megakaryocyte-derived extracellular vesicles comprise a lipid bilayer membrane comprising CLEC-2. In embodiments, between about 75% to about 99% of the megakaryocyte-derived extracellular vesicles comprise a lipid bilayer membrane comprising CLEC-2. In embodiments, between about 90% to about 99% of the megakaryocyte-derived extracellular vesicles comprise a lipid bilayer membrane comprising CLEC-2. In embodiments, between about 95% to about 99% of the megakaryocyte-derived extracellular vesicles comprise a lipid bilayer membrane comprising CLEC-2.

In embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CLEC-2.

In embodiments, the megakaryocyte-derived extracellular vesicles are characterized by a higher expression and/or presence of CLEC-2 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CLEC-2 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CLEC-2 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CLEC-2 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about a 16-fold, or about a 4-fold to about an 8-fold lower amount of CLEC-2 than platelet free plasma (PFP) MkEVs. In embodiments, the megakaryocyte-derived extracellular vesicles have about a 4-fold or about a 5-fold lower amount of CLEC-2 than platelet free plasma (PFP) MkEVs. In embodiments, the megakaryocyte-derived extracellular vesicles have about a 4-fold to about a 32-fold, or about an 8-fold to about a 16-fold lower amount of CLEC-2 than platelet derived extracellular vesicles (PLT EVs). In embodiments, the megakaryocyte-derived extracellular vesicles have about a 10-fold or about a 12-fold lower amount of CLEC-2 than platelet derived extracellular vesicles (PLT EVs).

In embodiments, greater than about 50% of the megakaryocyte-derived extracellular vesicles comprise a lipid bilayer membrane comprising LAMP-1 (CD107A). In embodiments, greater than about 40% of the megakaryocyte-derived extracellular vesicles comprise a lipid bilayer membrane comprising LAMP-1 (CD107A). In embodiments, greater than about 60% of the megakaryocyte-derived extracellular vesicles comprise a lipid bilayer membrane comprising LAMP-1 (CD107A). In embodiments, greater than about 70% of the megakaryocyte-derived extracellular vesicles comprise a lipid bilayer membrane comprising LAMP-1 (CD107A). In embodiments, greater than about 80% of the megakaryocyte-derived extracellular vesicles comprise a lipid bilayer membrane comprising LAMP-1 (CD107A). In embodiments, greater than about 90% of the megakaryocyte-derived extracellular vesicles comprise a lipid bilayer membrane comprising LAMP-1 (CD107A). In embodiments, greater than about 95% of the megakaryocyte-derived extracellular vesicles comprise a lipid bilayer membrane comprising LAMP-1 (CD107A). In embodiments, greater than about 99% of the megakaryocyte-derived extracellular vesicles comprise a lipid bilayer membrane comprising LAMP-1 (CD107A).

In embodiments, about 50% or less of the megakaryocyte-derived extracellular vesicles comprise a lipid bilayer membrane comprising LAMP-1 (CD107A). In embodiments, about 40% or less of the megakaryocyte-derived extracellular vesicles comprise a lipid bilayer membrane comprising LAMP-1 (CD107A). In embodiments, about 60% or less of the megakaryocyte-derived extracellular vesicles comprise a lipid bilayer membrane comprising LAMP-1 (CD107A). In embodiments, about 70% or less of the megakaryocyte-derived extracellular vesicles comprise a lipid bilayer membrane comprising LAMP-1 (CD107A). In embodiments, about 80% or less of the megakaryocyte-derived extracellular vesicles comprise a lipid bilayer membrane comprising LAMP-1 (CD107A). In embodiments, about 90% or less of the megakaryocyte-derived extracellular vesicles comprise a lipid bilayer membrane comprising LAMP-1 (CD107A). In embodiments, about 95% or less of the megakaryocyte-derived extracellular vesicles comprise a lipid bilayer membrane comprising LAMP-1 (CD107A). In embodiments, about 99% or less of the megakaryocyte-derived extracellular vesicles comprise a lipid bilayer membrane comprising LAMP-1 (CD107A).

In embodiments, less than about 50% of the megakaryocyte-derived extracellular vesicles comprise a lipid bilayer membrane comprising LAMP-1 (CD107A). In embodiments, less than about 40% of the megakaryocyte-derived extracellular vesicles comprise a lipid bilayer membrane comprising LAMP-1 (CD107A). In embodiments, less than about 30% of the megakaryocyte-derived extracellular vesicles comprise a lipid bilayer membrane comprising LAMP-1 (CD107A). In embodiments, less than about 25% of the megakaryocyte-derived extracellular vesicles comprise a lipid bilayer membrane comprising LAMP-1 (CD107A). In embodiments, less than about 20% of the megakaryocyte-derived extracellular vesicles comprise a lipid bilayer membrane comprising LAMP-1 (CD107A). In embodiments, less than about 15% of the megakaryocyte-derived extracellular vesicles comprise a lipid bilayer membrane comprising LAMP-1 (CD107A). In embodiments, less than about 10% of the megakaryocyte-derived extracellular vesicles comprise a lipid bilayer membrane comprising LAMP-1 (CD107A). In embodiments, less than about 5% of the megakaryocyte-derived extracellular vesicles comprise a lipid bilayer membrane comprising LAMP-1 (CD107A). In embodiments, less than about 1% of the megakaryocyte-derived extracellular vesicles comprise a lipid bilayer membrane comprising LAMP-1 (CD107A).

In embodiments, between about 1% to about 99% of the megakaryocyte-derived extracellular vesicles comprise a lipid bilayer membrane comprising LAMP-1 (CD107A). In embodiments, between about 1% to about 50% of the megakaryocyte-derived extracellular vesicles comprise a lipid bilayer membrane comprising LAMP-1 (CD107A). In embodiments, between about 1% to about 25% of the megakaryocyte-derived extracellular vesicles comprise a lipid bilayer membrane comprising LAMP-1 (CD107A). In embodiments, between about 1% to about 10% of the megakaryocyte-derived extracellular vesicles comprise a lipid bilayer membrane comprising LAMP-1 (CD107A). In embodiments, between about 1% to about 5% of the megakaryocyte-derived extracellular vesicles comprise a lipid bilayer membrane comprising LAMP-1 (CD107A). In embodiments, between about 1% to about 2% of the megakaryocyte-derived extracellular vesicles comprise a lipid bilayer membrane comprising LAMP-1 (CD107A). In embodiments, between about 50% to about 99% of the megakaryocyte-derived extracellular vesicles comprise a lipid bilayer membrane comprising LAMP-1 (CD107A). In embodiments, between about 75% to about 99% of the megakaryocyte-derived extracellular vesicles comprise a lipid bilayer membrane comprising LAMP-1 (CD107A). In embodiments, between about 90% to about 99% of the megakaryocyte-derived extracellular vesicles comprise a lipid bilayer membrane comprising LAMP-1 (CD107A). In embodiments, between about 95% to about 99% of the megakaryocyte-derived extracellular vesicles comprise a lipid bilayer membrane comprising LAMP-1 (CD107A).

In embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising LAMP-1 (CD107A).

In embodiments, the megakaryocyte-derived extracellular vesicles are free of, or substantially free of LAMP-1 (CD107A).

In embodiments, the megakaryocyte-derived extracellular vesicles are characterized by a higher expression and/or presence of LAMP-1 (CD107A) than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of LAMP-1 (CD107A) than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of LAMP-1 (CD107A) than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of LAMP-1 (CD107A) than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 1-fold to about a 2-fold, lower amount of LAMP-1 (CD107A) than platelet free plasma (PFP) MkEVs. In embodiments, the megakaryocyte-derived extracellular vesicles have an amount of LAMP-1 (CD107A) that is substantially the same as platelet free plasma (PFP) MkEVs. In embodiments, the megakaryocyte-derived extracellular vesicles have about a 2-fold to about a 8-fold, or about a 2-fold to about a 4-fold lower amount of LAMP-1 (CD107A) than platelet derived extracellular vesicles (PLT EVs). In embodiments, the megakaryocyte-derived extracellular vesicles have about a 3-fold or about a 4-fold lower amount of LAMP-1 (CD107A) than platelet derived extracellular vesicles (PLT EVs).

In embodiments, greater than about 50% of the megakaryocyte-derived extracellular vesicles comprise a lipid bilayer membrane comprising CD63. In embodiments, greater than about 40% of the megakaryocyte-derived extracellular vesicles comprise a lipid bilayer membrane comprising CD63. In embodiments, greater than about 60% of the megakaryocyte-derived extracellular vesicles comprise a lipid bilayer membrane comprising CD63. In embodiments, greater than about 70% of the megakaryocyte-derived extracellular vesicles comprise a lipid bilayer membrane comprising CD63. In embodiments, greater than about 80% of the megakaryocyte-derived extracellular vesicles comprise a lipid bilayer membrane comprising CD63. In embodiments, greater than about 90% of the megakaryocyte-derived extracellular vesicles comprise a lipid bilayer membrane comprising CD63. In embodiments, greater than about 95% of the megakaryocyte-derived extracellular vesicles comprise a lipid bilayer membrane comprising CD63. In embodiments, greater than about 99% of the megakaryocyte-derived extracellular vesicles comprise a lipid bilayer membrane comprising CD63.

In embodiments, about 50% or less of the megakaryocyte-derived extracellular vesicles comprise a lipid bilayer membrane comprising CD63. In embodiments, about 40% or less of the megakaryocyte-derived extracellular vesicles comprise a lipid bilayer membrane comprising CD63. In embodiments, about 60% or less of the megakaryocyte-derived extracellular vesicles comprise a lipid bilayer membrane comprising CD63. In embodiments, about 70% or less of the megakaryocyte-derived extracellular vesicles comprise a lipid bilayer membrane comprising CD63. In embodiments, about 80% or less of the megakaryocyte-derived extracellular vesicles comprise a lipid bilayer membrane comprising CD63. In embodiments, about 90% or less of the megakaryocyte-derived extracellular vesicles comprise a lipid bilayer membrane comprising CD63. In embodiments, about 95% or less of the megakaryocyte-derived extracellular vesicles comprise a lipid bilayer membrane comprising CD63. In embodiments, about 99% or less of the megakaryocyte-derived extracellular vesicles comprise a lipid bilayer membrane comprising CD63.

In embodiments, less than about 50% of the megakaryocyte-derived extracellular vesicles comprise a lipid bilayer membrane comprising CD63. In embodiments, less than about 40% of the megakaryocyte-derived extracellular vesicles comprise a lipid bilayer membrane comprising CD63. In embodiments, less than about 30% of the megakaryocyte-derived extracellular vesicles comprise a lipid bilayer membrane comprising CD63. In embodiments, less than about 25% of the megakaryocyte-derived extracellular vesicles comprise a lipid bilayer membrane comprising CD63. In embodiments, less than about 20% of the megakaryocyte-derived extracellular vesicles comprise a lipid bilayer membrane comprising CD63. In embodiments, less than about 15% of the megakaryocyte-derived extracellular vesicles comprise a lipid bilayer membrane comprising CD63. In embodiments, less than about 10% of the megakaryocyte-derived extracellular vesicles comprise a lipid bilayer membrane comprising CD63. In embodiments, less than about 5% of the megakaryocyte-derived extracellular vesicles comprise a lipid bilayer membrane comprising CD63. In embodiments, less than about 1% of the megakaryocyte-derived extracellular vesicles comprise a lipid bilayer membrane comprising CD63.

In embodiments, between about 1% to about 99% of the megakaryocyte-derived extracellular vesicles comprise a lipid bilayer membrane comprising CD63. In embodiments, between about 1% to about 50% of the megakaryocyte-derived extracellular vesicles comprise a lipid bilayer membrane comprising CD63. In embodiments, between about 1% to about 25% of the megakaryocyte-derived extracellular vesicles comprise a lipid bilayer membrane comprising CD63. In embodiments, between about 1% to about 10% of the megakaryocyte-derived extracellular vesicles comprise a lipid bilayer membrane comprising CD63. In embodiments, between about 1% to about 5% of the megakaryocyte-derived extracellular vesicles comprise a lipid bilayer membrane comprising CD63. In embodiments, between about 1% to about 2% of the megakaryocyte-derived extracellular vesicles comprise a lipid bilayer membrane comprising CD63. In embodiments, between about 50% to about 99% of the megakaryocyte-derived extracellular vesicles comprise a lipid bilayer membrane comprising CD63. In embodiments, between about 75% to about 99% of the megakaryocyte-derived extracellular vesicles comprise a lipid bilayer membrane comprising CD63. In embodiments, between about 90% to about 99% of the megakaryocyte-derived extracellular vesicles comprise a lipid bilayer membrane comprising CD63. In embodiments, between about 95% to about 99% of the megakaryocyte-derived extracellular vesicles comprise a lipid bilayer membrane comprising CD63.

In embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD63.

In embodiments, between about 1% to about 30% of the megakaryocyte-derived extracellular vesicles comprise a lipid bilayer membrane comprising CD63. In embodiments, between about 5% to about 25% of the megakaryocyte-derived extracellular vesicles comprise a lipid bilayer membrane comprising CD63. In embodiments, between about 10% to about 20% of the megakaryocyte-derived extracellular vesicles comprise a lipid bilayer membrane comprising CD63. In embodiments, between about 13% to about 19% of the megakaryocyte-derived extracellular vesicles comprise a lipid bilayer membrane comprising CD63.

In embodiments, the megakaryocyte-derived extracellular vesicles are characterized by a higher expression and/or presence of CD63 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD63 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD63 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD63 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about an 8-fold, or about a 2-fold to about a 4-fold greater amount of CD63 than platelet free plasma (PFP) MkEVs. In embodiments, the megakaryocyte-derived extracellular vesicles have about a 2-fold or about a 3-fold greater amount of CD63 than platelet free plasma (PFP) MkEVs. In embodiments, the megakaryocyte-derived extracellular vesicles have about a 1.1-fold to about a 2-fold lower amount of CD63 than platelet derived extracellular vesicles (PLT EVs). In embodiments, the megakaryocyte-derived extracellular vesicles have about a 1.1-fold or about a 1.2-fold lower amount of CD63 than platelet derived extracellular vesicles (PLT EVs). In embodiments, the megakaryocyte-derived extracellular vesicles have an amount of CD63 that is substantially the same as platelet derived extracellular vesicles (PLT EVs).

In embodiments, greater than about 50% of the megakaryocyte-derived extracellular vesicles comprise a lipid bilayer membrane comprising CD42b. In embodiments, greater than about 40% of the megakaryocyte-derived extracellular vesicles comprise a lipid bilayer membrane comprising CD42b. In embodiments, greater than about 60% of the megakaryocyte-derived extracellular vesicles comprise a lipid bilayer membrane comprising CD42b. In embodiments, greater than about 70% of the megakaryocyte-derived extracellular vesicles comprise a lipid bilayer membrane comprising CD42b. In embodiments, greater than about 80% of the megakaryocyte-derived extracellular vesicles comprise a lipid bilayer membrane comprising CD42b. In embodiments, greater than about 90% of the megakaryocyte-derived extracellular vesicles comprise a lipid bilayer membrane comprising CD42b. In embodiments, greater than about 95% of the megakaryocyte-derived extracellular vesicles comprise a lipid bilayer membrane comprising CD42b. In embodiments, greater than about 99% of the megakaryocyte-derived extracellular vesicles comprise a lipid bilayer membrane comprising CD42b.

In embodiments, about 50% or less of the megakaryocyte-derived extracellular vesicles comprise a lipid bilayer membrane comprising CD42b. In embodiments, about 40% or less of the megakaryocyte-derived extracellular vesicles comprise a lipid bilayer membrane comprising CD42b. In embodiments, about 60% or less of the megakaryocyte-derived extracellular vesicles comprise a lipid bilayer membrane comprising CD42b. In embodiments, about 70% or less of the megakaryocyte-derived extracellular vesicles comprise a lipid bilayer membrane comprising CD42b. In embodiments, about 80% or less of the megakaryocyte-derived extracellular vesicles comprise a lipid bilayer membrane comprising CD42b. In embodiments, about 90% or less of the megakaryocyte-derived extracellular vesicles comprise a lipid bilayer membrane comprising CD42b. In embodiments, about 95% or less of the megakaryocyte-derived extracellular vesicles comprise a lipid bilayer membrane comprising CD42b. In embodiments, about 99% or less of the megakaryocyte-derived extracellular vesicles comprise a lipid bilayer membrane comprising CD42b.

In embodiments, less than about 50% of the megakaryocyte-derived extracellular vesicles comprise a lipid bilayer membrane comprising CD42b. In embodiments, less than about 40% of the megakaryocyte-derived extracellular vesicles comprise a lipid bilayer membrane comprising CD42b. In embodiments, less than about 30% of the megakaryocyte-derived extracellular vesicles comprise a lipid bilayer membrane comprising CD42b. In embodiments, less than about 25% of the megakaryocyte-derived extracellular vesicles comprise a lipid bilayer membrane comprising CD42b. In embodiments, less than about 20% of the megakaryocyte-derived extracellular vesicles comprise a lipid bilayer membrane comprising CD42b. In embodiments, less than about 15% of the megakaryocyte-derived extracellular vesicles comprise a lipid bilayer membrane comprising CD42b. In embodiments, less than about 10% of the megakaryocyte-derived extracellular vesicles comprise a lipid bilayer membrane comprising CD42b. In embodiments, less than about 5% of the megakaryocyte-derived extracellular vesicles comprise a lipid bilayer membrane comprising CD42b. In embodiments, less than about 1% of the megakaryocyte-derived extracellular vesicles comprise a lipid bilayer membrane comprising CD42b.

In embodiments, between about 1% to about 99% of the megakaryocyte-derived extracellular vesicles comprise a lipid bilayer membrane comprising CD42b. In embodiments, between about 1% to about 50% of the megakaryocyte-derived extracellular vesicles comprise a lipid bilayer membrane comprising CD42b. In embodiments, between about 1% to about 25% of the megakaryocyte-derived extracellular vesicles comprise a lipid bilayer membrane comprising CD42b. In embodiments, between about 1% to about 10% of the megakaryocyte-derived extracellular vesicles comprise a lipid bilayer membrane comprising CD42b. In embodiments, between about 1% to about 5% of the megakaryocyte-derived extracellular vesicles comprise a lipid bilayer membrane comprising CD42b. In embodiments, between about 1% to about 2% of the megakaryocyte-derived extracellular vesicles comprise a lipid bilayer membrane comprising CD42b. In embodiments, between about 50% to about 99% of the megakaryocyte-derived extracellular vesicles comprise a lipid bilayer membrane comprising CD42b. In embodiments, between about 75% to about 99% of the megakaryocyte-derived extracellular vesicles comprise a lipid bilayer membrane comprising CD42b. In embodiments, between about 90% to about 99% of the megakaryocyte-derived extracellular vesicles comprise a lipid bilayer membrane comprising CD42b. In embodiments, between about 95% to about 99% of the megakaryocyte-derived extracellular vesicles comprise a lipid bilayer membrane comprising CD42b.

In embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD42b.

In embodiments, the megakaryocyte-derived extracellular vesicles are characterized by a higher expression and/or presence of CD42b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD42b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD42b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD42b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about an 8-fold to about a 32-fold, or about a 10-fold to about a 20-fold lower amount of CD42b than platelet free plasma (PFP) MkEVs. In embodiments, the megakaryocyte-derived extracellular vesicles have about a 16-fold or about a 20-fold lower amount of CD42b than platelet free plasma (PFP) MkEVs. In embodiments, the megakaryocyte-derived extracellular vesicles have about a 64-fold to about a 128-fold, or about a 50-fold to about a 75-fold lower amount of CD42b than platelet derived extracellular vesicles (PLT EVs). In embodiments, the megakaryocyte-derived extracellular vesicles have about a 64-fold or about a 70-fold lower amount of CD42b than platelet derived extracellular vesicles (PLT EVs).

In embodiments, greater than about 50% of the megakaryocyte-derived extracellular vesicles comprise a lipid bilayer membrane comprising CD9. In embodiments, greater than about 40% of the megakaryocyte-derived extracellular vesicles comprise a lipid bilayer membrane comprising CD9. In embodiments, greater than about 60% of the megakaryocyte-derived extracellular vesicles comprise a lipid bilayer membrane comprising CD9. In embodiments, greater than about 70% of the megakaryocyte-derived extracellular vesicles comprise a lipid bilayer membrane comprising CD9. In embodiments, greater than about 80% of the megakaryocyte-derived extracellular vesicles comprise a lipid bilayer membrane comprising CD9. In embodiments, greater than about 90% of the megakaryocyte-derived extracellular vesicles comprise a lipid bilayer membrane comprising CD9. In embodiments, greater than about 95% of the megakaryocyte-derived extracellular vesicles comprise a lipid bilayer membrane comprising CD9. In embodiments, greater than about 99% of the megakaryocyte-derived extracellular vesicles comprise a lipid bilayer membrane comprising CD9.

In embodiments, about 50% or less of the megakaryocyte-derived extracellular vesicles comprise a lipid bilayer membrane comprising CD9. In embodiments, about 40% or less of the megakaryocyte-derived extracellular vesicles comprise a lipid bilayer membrane comprising CD9. In embodiments, about 60% or less of the megakaryocyte-derived extracellular vesicles comprise a lipid bilayer membrane comprising CD9. In embodiments, about 70% or less of the megakaryocyte-derived extracellular vesicles comprise a lipid bilayer membrane comprising CD9. In embodiments, about 80% or less of the megakaryocyte-derived extracellular vesicles comprise a lipid bilayer membrane comprising CD9. In embodiments, about 90% or less of the megakaryocyte-derived extracellular vesicles comprise a lipid bilayer membrane comprising CD9. In embodiments, about 95% or less of the megakaryocyte-derived extracellular vesicles comprise a lipid bilayer membrane comprising CD9. In embodiments, about 99% or less of the megakaryocyte-derived extracellular vesicles comprise a lipid bilayer membrane comprising CD9.

In embodiments, less than about 50% of the megakaryocyte-derived extracellular vesicles comprise a lipid bilayer membrane comprising CD9. In embodiments, less than about 40% of the megakaryocyte-derived extracellular vesicles comprise a lipid bilayer membrane comprising CD9. In embodiments, less than about 30% of the megakaryocyte-derived extracellular vesicles comprise a lipid bilayer membrane comprising CD9. In embodiments, less than about 25% of the megakaryocyte-derived extracellular vesicles comprise a lipid bilayer membrane comprising CD9. In embodiments, less than about 20% of the megakaryocyte-derived extracellular vesicles comprise a lipid bilayer membrane comprising CD9. In embodiments, less than about 15% of the megakaryocyte-derived extracellular vesicles comprise a lipid bilayer membrane comprising CD9. In embodiments, less than about 10% of the megakaryocyte-derived extracellular vesicles comprise a lipid bilayer membrane comprising CD9. In embodiments, less than about 5% of the megakaryocyte-derived extracellular vesicles comprise a lipid bilayer membrane comprising CD9. In embodiments, less than about 1% of the megakaryocyte-derived extracellular vesicles comprise a lipid bilayer membrane comprising CD9.

In embodiments, between about 1% to about 99% of the megakaryocyte-derived extracellular vesicles comprise a lipid bilayer membrane comprising CD9. In embodiments, between about 1% to about 50% of the megakaryocyte-derived extracellular vesicles comprise a lipid bilayer membrane comprising CD9. In embodiments, between about 1% to about 25% of the megakaryocyte-derived extracellular vesicles comprise a lipid bilayer membrane comprising CD9. In embodiments, between about 1% to about 10% of the megakaryocyte-derived extracellular vesicles comprise a lipid bilayer membrane comprising CD9. In embodiments, between about 1% to about 5% of the megakaryocyte-derived extracellular vesicles comprise a lipid bilayer membrane comprising CD9. In embodiments, between about 1% to about 2% of the megakaryocyte-derived extracellular vesicles comprise a lipid bilayer membrane comprising CD9. In embodiments, between about 20% to about 60% of the megakaryocyte-derived extracellular vesicles comprise a lipid bilayer membrane comprising CD9. In embodiments, between about 35% to about 55% of the megakaryocyte-derived extracellular vesicles comprise a lipid bilayer membrane comprising CD9. In embodiments, between about 50% to about 99% of the megakaryocyte-derived extracellular vesicles comprise a lipid bilayer membrane comprising CD9. In embodiments, between about 75% to about 99% of the megakaryocyte-derived extracellular vesicles comprise a lipid bilayer membrane comprising CD9. In embodiments, between about 90% to about 99% of the megakaryocyte-derived extracellular vesicles comprise a lipid bilayer membrane comprising CD9. In embodiments, between about 95% to about 99% of the megakaryocyte-derived extracellular vesicles comprise a lipid bilayer membrane comprising CD9.

In embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD9.

In embodiments, between about 50% to about 70% of the megakaryocyte-derived extracellular vesicles comprise a lipid bilayer membrane comprising CD9. In embodiments, between about 60% to about 70% of the megakaryocyte-derived extracellular vesicles comprise a lipid bilayer membrane comprising CD9. In embodiments, between about 62% to about 68% of the megakaryocyte-derived extracellular vesicles comprise a lipid bilayer membrane comprising CD9. In embodiments, between about 65% to about 66% of the megakaryocyte-derived extracellular vesicles comprise a lipid bilayer membrane comprising CD9.

In embodiments, between about 50% to about 99% of the megakaryocyte-derived extracellular vesicles comprise a lipid bilayer membrane comprising CD9.

In embodiments, the megakaryocyte-derived extracellular vesicles are characterized by a higher expression and/or presence of CD9 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD9 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD9 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD9 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 1.5-fold to about a 4-fold, or about a 2-fold to about a 4-fold greater amount of CD9 than platelet free plasma (PFP) MkEVs. In embodiments, the megakaryocyte-derived extracellular vesicles have about a 2-fold greater amount of CD9 than platelet free plasma (PFP) MkEVs. In embodiments, the megakaryocyte-derived extracellular vesicles have about a 1.1-fold to about a 2-fold lower amount of CD9 than platelet derived extracellular vesicles (PLT EVs). In embodiments, the megakaryocyte-derived extracellular vesicles have about a 1.1-fold or about a 1.2-fold lower amount of CD9 than platelet derived extracellular vesicles (PLT EVs). In embodiments, the megakaryocyte-derived extracellular vesicles have an amount of CD9 that is substantially the same as platelet derived extracellular vesicles (PLT EVs).

In embodiments, greater than about 50% of the megakaryocyte-derived extracellular vesicles comprise a lipid bilayer membrane comprising CD31. In embodiments, greater than about 40% of the megakaryocyte-derived extracellular vesicles comprise a lipid bilayer membrane comprising CD31. In embodiments, greater than about 60% of the megakaryocyte-derived extracellular vesicles comprise a lipid bilayer membrane comprising CD31. In embodiments, greater than about 70% of the megakaryocyte-derived extracellular vesicles comprise a lipid bilayer membrane comprising CD31. In embodiments, greater than about 80% of the megakaryocyte-derived extracellular vesicles comprise a lipid bilayer membrane comprising CD31. In embodiments, greater than about 90% of the megakaryocyte-derived extracellular vesicles comprise a lipid bilayer membrane comprising CD31. In embodiments, greater than about 95% of the megakaryocyte-derived extracellular vesicles comprise a lipid bilayer membrane comprising CD31. In embodiments, greater than about 99% of the megakaryocyte-derived extracellular vesicles comprise a lipid bilayer membrane comprising CD31.

In embodiments, about 50% or less of the megakaryocyte-derived extracellular vesicles comprise a lipid bilayer membrane comprising CD31. In embodiments, about 40% or less of the megakaryocyte-derived extracellular vesicles comprise a lipid bilayer membrane comprising CD31. In embodiments, about 60% or less of the megakaryocyte-derived extracellular vesicles comprise a lipid bilayer membrane comprising CD31. In embodiments, about 70% or less of the megakaryocyte-derived extracellular vesicles comprise a lipid bilayer membrane comprising CD31. In embodiments, about 80% or less of the megakaryocyte-derived extracellular vesicles comprise a lipid bilayer membrane comprising CD31. In embodiments, about 90% or less of the megakaryocyte-derived extracellular vesicles comprise a lipid bilayer membrane comprising CD31. In embodiments, about 95% or less of the megakaryocyte-derived extracellular vesicles comprise a lipid bilayer membrane comprising CD31. In embodiments, about 99% or less of the megakaryocyte-derived extracellular vesicles comprise a lipid bilayer membrane comprising CD31.

In embodiments, less than about 50% of the megakaryocyte-derived extracellular vesicles comprise a lipid bilayer membrane comprising CD31. In embodiments, less than about 40% of the megakaryocyte-derived extracellular vesicles comprise a lipid bilayer membrane comprising CD31. In embodiments, less than about 30% of the megakaryocyte-derived extracellular vesicles comprise a lipid bilayer membrane comprising CD31. In embodiments, less than about 25% of the megakaryocyte-derived extracellular vesicles comprise a lipid bilayer membrane comprising CD31. In embodiments, less than about 20% of the megakaryocyte-derived extracellular vesicles comprise a lipid bilayer membrane comprising CD31. In embodiments, less than about 15% of the megakaryocyte-derived extracellular vesicles comprise a lipid bilayer membrane comprising CD31. In embodiments, less than about 10% of the megakaryocyte-derived extracellular vesicles comprise a lipid bilayer membrane comprising CD31. In embodiments, less than about 5% of the megakaryocyte-derived extracellular vesicles comprise a lipid bilayer membrane comprising CD31. In embodiments, less than about 1% of the megakaryocyte-derived extracellular vesicles comprise a lipid bilayer membrane comprising CD31.

In embodiments, between about 1% to about 99% of the megakaryocyte-derived extracellular vesicles comprise a lipid bilayer membrane comprising CD31. In embodiments, between about 1% to about 50% of the megakaryocyte-derived extracellular vesicles comprise a lipid bilayer membrane comprising CD31. In embodiments, between about 1% to about 25% of the megakaryocyte-derived extracellular vesicles comprise a lipid bilayer membrane comprising CD31. In embodiments, between about 1% to about 10% of the megakaryocyte-derived extracellular vesicles comprise a lipid bilayer membrane comprising CD31. In embodiments, between about 1% to about 5% of the megakaryocyte-derived extracellular vesicles comprise a lipid bilayer membrane comprising CD31. In embodiments, between about 1% to about 2% of the megakaryocyte-derived extracellular vesicles comprise a lipid bilayer membrane comprising CD31. In embodiments, between about 50% to about 99% of the megakaryocyte-derived extracellular vesicles comprise a lipid bilayer membrane comprising CD31. In embodiments, between about 75% to about 99% of the megakaryocyte-derived extracellular vesicles comprise a lipid bilayer membrane comprising CD31. In embodiments, between about 90% to about 99% of the megakaryocyte-derived extracellular vesicles comprise a lipid bilayer membrane comprising CD31. In embodiments, between about 95% to about 99% of the megakaryocyte-derived extracellular vesicles comprise a lipid bilayer membrane comprising CD31.

In embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD31.

In embodiments, between about 5% to about 50% of the megakaryocyte-derived extracellular vesicles comprise a lipid bilayer membrane comprising CD31. In embodiments, between about 10% to about 40% of the megakaryocyte-derived extracellular vesicles comprise a lipid bilayer membrane comprising CD31. In embodiments, between about 10% to about 35% of the megakaryocyte-derived extracellular vesicles comprise a lipid bilayer membrane comprising CD31. In embodiments, between about 13% to about 31% of the megakaryocyte-derived extracellular vesicles comprise a lipid bilayer membrane comprising CD31.

In embodiments, the megakaryocyte-derived extracellular vesicles are characterized by a higher expression and/or presence of CD31 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD31 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD31 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD31 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 1.1-fold to about a 4-fold, or about a 1.1-fold to about a 2-fold lower amount of CD31 than platelet free plasma (PFP) MkEVs. In embodiments, the megakaryocyte-derived extracellular vesicles have about a 1.5-fold lower amount of CD31 than platelet free plasma (PFP) MkEVs. In embodiments, the megakaryocyte-derived extracellular vesicles have about a 2-fold to about a 4-fold lower amount of CD31 than platelet derived extracellular vesicles (PLT EVs). In embodiments, the megakaryocyte-derived extracellular vesicles have about a 2-fold or about a 3-fold lower amount of CD31 than platelet derived extracellular vesicles (PLT EVs).

In embodiments, greater than about 50% of the megakaryocyte-derived extracellular vesicles comprise a lipid bilayer membrane comprising CD47. In embodiments, greater than about 40% of the megakaryocyte-derived extracellular vesicles comprise a lipid bilayer membrane comprising CD47. In embodiments, greater than about 60% of the megakaryocyte-derived extracellular vesicles comprise a lipid bilayer membrane comprising CD47. In embodiments, greater than about 70% of the megakaryocyte-derived extracellular vesicles comprise a lipid bilayer membrane comprising CD47. In embodiments, greater than about 80% of the megakaryocyte-derived extracellular vesicles comprise a lipid bilayer membrane comprising CD47. In embodiments, greater than about 90% of the megakaryocyte-derived extracellular vesicles comprise a lipid bilayer membrane comprising CD47. In embodiments, greater than about 95% of the megakaryocyte-derived extracellular vesicles comprise a lipid bilayer membrane comprising CD47. In embodiments, greater than about 99% of the megakaryocyte-derived extracellular vesicles comprise a lipid bilayer membrane comprising CD47.

In embodiments, about 50% or less of the megakaryocyte-derived extracellular vesicles comprise a lipid bilayer membrane comprising CD47. In embodiments, about 40% or less of the megakaryocyte-derived extracellular vesicles comprise a lipid bilayer membrane comprising CD47. In embodiments, about 60% or less of the megakaryocyte-derived extracellular vesicles comprise a lipid bilayer membrane comprising CD47. In embodiments, about 70% or less of the megakaryocyte-derived extracellular vesicles comprise a lipid bilayer membrane comprising CD47. In embodiments, about 80% or less of the megakaryocyte-derived extracellular vesicles comprise a lipid bilayer membrane comprising CD47. In embodiments, about 90% or less of the megakaryocyte-derived extracellular vesicles comprise a lipid bilayer membrane comprising CD47. In embodiments, about 95% or less of the megakaryocyte-derived extracellular vesicles comprise a lipid bilayer membrane comprising CD47. In embodiments, about 99% or less of the megakaryocyte-derived extracellular vesicles comprise a lipid bilayer membrane comprising CD47.

In embodiments, less than about 50% of the megakaryocyte-derived extracellular vesicles comprise a lipid bilayer membrane comprising CD47. In embodiments, less than about 40% of the megakaryocyte-derived extracellular vesicles comprise a lipid bilayer membrane comprising CD47. In embodiments, less than about 30% of the megakaryocyte-derived extracellular vesicles comprise a lipid bilayer membrane comprising CD47. In embodiments, less than about 25% of the megakaryocyte-derived extracellular vesicles comprise a lipid bilayer membrane comprising CD47. In embodiments, less than about 20% of the megakaryocyte-derived extracellular vesicles comprise a lipid bilayer membrane comprising CD47. In embodiments, less than about 15% of the megakaryocyte-derived extracellular vesicles comprise a lipid bilayer membrane comprising CD47. In embodiments, less than about 10% of the megakaryocyte-derived extracellular vesicles comprise a lipid bilayer membrane comprising CD47. In embodiments, less than about 5% of the megakaryocyte-derived extracellular vesicles comprise a lipid bilayer membrane comprising CD47. In embodiments, less than about 1% of the megakaryocyte-derived extracellular vesicles comprise a lipid bilayer membrane comprising CD47.

In embodiments, between about 1% to about 99% of the megakaryocyte-derived extracellular vesicles comprise a lipid bilayer membrane comprising CD47. In embodiments, between about 1% to about 50% of the megakaryocyte-derived extracellular vesicles comprise a lipid bilayer membrane comprising CD47. In embodiments, between about 1% to about 25% of the megakaryocyte-derived extracellular vesicles comprise a lipid bilayer membrane comprising CD47. In embodiments, between about 1% to about 10% of the megakaryocyte-derived extracellular vesicles comprise a lipid bilayer membrane comprising CD47. In embodiments, between about 1% to about 5% of the megakaryocyte-derived extracellular vesicles comprise a lipid bilayer membrane comprising CD47. In embodiments, between about 1% to about 2% of the megakaryocyte-derived extracellular vesicles comprise a lipid bilayer membrane comprising CD47. In embodiments, between about 50% to about 99% of the megakaryocyte-derived extracellular vesicles comprise a lipid bilayer membrane comprising CD47. In embodiments, between about 75% to about 99% of the megakaryocyte-derived extracellular vesicles comprise a lipid bilayer membrane comprising CD47. In embodiments, between about 90% to about 99% of the megakaryocyte-derived extracellular vesicles comprise a lipid bilayer membrane comprising CD47. In embodiments, between about 95% to about 99% of the megakaryocyte-derived extracellular vesicles comprise a lipid bilayer membrane comprising CD47.

In embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD47.

In embodiments, between about 1% to about 50% of the megakaryocyte-derived extracellular vesicles comprise a lipid bilayer membrane comprising CD47. In embodiments, between about 10% to about 40% of the megakaryocyte-derived extracellular vesicles comprise a lipid bilayer membrane comprising CD47. In embodiments, between about 20% to about 40% of the megakaryocyte-derived extracellular vesicles comprise a lipid bilayer membrane comprising CD47. In embodiments, between about 25% to about 35% of the megakaryocyte-derived extracellular vesicles comprise a lipid bilayer membrane comprising CD47.

In embodiments, the megakaryocyte-derived extracellular vesicles are characterized by a higher expression and/or presence of CD47 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD47 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD47 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD47 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 128-fold to about a 512-fold, or about a 256-fold to about a 512-fold, or about a 250-fold to about a 300-fold greater amount of CD47 than platelet free plasma (PFP) MkEVs. In embodiments, the megakaryocyte-derived extracellular vesicles have about a 256-fold or about a 300-fold greater amount of CD47 than platelet free plasma (PFP) MkEVs. In embodiments, the megakaryocyte-derived extracellular vesicles have about a 1.1-fold to about a 2-fold lower amount of CD47 than platelet derived extracellular vesicles (PLT EVs). In embodiments, the megakaryocyte-derived extracellular vesicles have about a 1.1-fold or about a 1.5-fold lower amount of CD47 than platelet derived extracellular vesicles (PLT EVs). In embodiments, the megakaryocyte-derived extracellular vesicles have an amount of CD47 that is substantially the same as platelet derived extracellular vesicles (PLT EVs).

In embodiments, greater than about 50% of the megakaryocyte-derived extracellular vesicles comprise a lipid bilayer membrane comprising CD147. In embodiments, greater than about 40% of the megakaryocyte-derived extracellular vesicles comprise a lipid bilayer membrane comprising CD147. In embodiments, greater than about 60% of the megakaryocyte-derived extracellular vesicles comprise a lipid bilayer membrane comprising CD147. In embodiments, greater than about 70% of the megakaryocyte-derived extracellular vesicles comprise a lipid bilayer membrane comprising CD147. In embodiments, greater than about 80% of the megakaryocyte-derived extracellular vesicles comprise a lipid bilayer membrane comprising CD147. In embodiments, greater than about 90% of the megakaryocyte-derived extracellular vesicles comprise a lipid bilayer membrane comprising CD147. In embodiments, greater than about 95% of the megakaryocyte-derived extracellular vesicles comprise a lipid bilayer membrane comprising CD147. In embodiments, greater than about 99% of the megakaryocyte-derived extracellular vesicles comprise a lipid bilayer membrane comprising CD147.

In embodiments, about 50% or less of the megakaryocyte-derived extracellular vesicles comprise a lipid bilayer membrane comprising CD147. In embodiments, about 40% or less of the megakaryocyte-derived extracellular vesicles comprise a lipid bilayer membrane comprising CD147. In embodiments, about 60% or less of the megakaryocyte-derived extracellular vesicles comprise a lipid bilayer membrane comprising CD147. In embodiments, about 70% or less of the megakaryocyte-derived extracellular vesicles comprise a lipid bilayer membrane comprising CD147. In embodiments, about 80% or less of the megakaryocyte-derived extracellular vesicles comprise a lipid bilayer membrane comprising CD147. In embodiments, about 90% or less of the megakaryocyte-derived extracellular vesicles comprise a lipid bilayer membrane comprising CD147. In embodiments, about 95% or less of the megakaryocyte-derived extracellular vesicles comprise a lipid bilayer membrane comprising CD147. In embodiments, about 99% or less of the megakaryocyte-derived extracellular vesicles comprise a lipid bilayer membrane comprising CD147. In embodiments, less than about 50% of the megakaryocyte-derived extracellular vesicles comprise a lipid bilayer membrane comprising CD147. In embodiments, less than about 40% of the megakaryocyte-derived extracellular vesicles comprise a lipid bilayer membrane comprising CD147. In embodiments, less than about 30% of the megakaryocyte-derived extracellular vesicles comprise a lipid bilayer membrane comprising CD147. In embodiments, less than about 25% of the megakaryocyte-derived extracellular vesicles comprise a lipid bilayer membrane comprising CD147. In embodiments, less than about 20% of the megakaryocyte-derived extracellular vesicles comprise a lipid bilayer membrane comprising CD147. In embodiments, less than about 15% of the megakaryocyte-derived extracellular vesicles comprise a lipid bilayer membrane comprising CD147. In embodiments, less than about 10% of the megakaryocyte-derived extracellular vesicles comprise a lipid bilayer membrane comprising CD147. In embodiments, less than about 5% of the megakaryocyte-derived extracellular vesicles comprise a lipid bilayer membrane comprising CD147. In embodiments, less than about 1% of the megakaryocyte-derived extracellular vesicles comprise a lipid bilayer membrane comprising CD147.

In embodiments, between about 1% to about 99% of the megakaryocyte-derived extracellular vesicles comprise a lipid bilayer membrane comprising CD147. In embodiments, between about 1% to about 50% of the megakaryocyte-derived extracellular vesicles comprise a lipid bilayer membrane comprising CD147. In embodiments, between about 1% to about 25% of the megakaryocyte-derived extracellular vesicles comprise a lipid bilayer membrane comprising CD147. In embodiments, between about 1% to about 10% of the megakaryocyte-derived extracellular vesicles comprise a lipid bilayer membrane comprising CD147. In embodiments, between about 1% to about 5% of the megakaryocyte-derived extracellular vesicles comprise a lipid bilayer membrane comprising CD147. In embodiments, between about 1% to about 2% of the megakaryocyte-derived extracellular vesicles comprise a lipid bilayer membrane comprising CD147. In embodiments, between about 50% to about 99% of the megakaryocyte-derived extracellular vesicles comprise a lipid bilayer membrane comprising CD147. In embodiments, between about 75% to about 99% of the megakaryocyte-derived extracellular vesicles comprise a lipid bilayer membrane comprising CD147. In embodiments, between about 90% to about 99% of the megakaryocyte-derived extracellular vesicles comprise a lipid bilayer membrane comprising CD147. In embodiments, between about 95% to about 99% of the megakaryocyte-derived extracellular vesicles comprise a lipid bilayer membrane comprising CD147.

In embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD147.

In embodiments, between about 1% to about 15% of the megakaryocyte-derived extracellular vesicles comprise a lipid bilayer membrane comprising CD147. In embodiments, between about 1% to about 10% of the megakaryocyte-derived extracellular vesicles comprise a lipid bilayer membrane comprising CD147. In embodiments, between about 3% to about 8% of the megakaryocyte-derived extracellular vesicles comprise a lipid bilayer membrane comprising CD147. In embodiments, between about 4% to about 7% of the megakaryocyte-derived extracellular vesicles comprise a lipid bilayer membrane comprising CD147.

In embodiments, the megakaryocyte-derived extracellular vesicles are characterized by a higher expression and/or presence of CD147 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD147 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD147 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD147 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about an 8-fold, or about a 2-fold to about a 4-fold lower amount of CD147 than platelet free plasma (PFP) MkEVs. In embodiments, the megakaryocyte-derived extracellular vesicles have about a 2-fold or about a 3-fold lower amount of CD147 than platelet free plasma (PFP) MkEVs. In embodiments, the megakaryocyte-derived extracellular vesicles have about a 1.1-fold to about a 2-fold lower amount of CD147 than platelet derived extracellular vesicles (PLT EVs). In embodiments, the megakaryocyte-derived extracellular vesicles have about a 1.1-fold or about a 1.2-fold lower amount of CD147 than platelet derived extracellular vesicles (PLT EVs). In embodiments, the megakaryocyte-derived extracellular vesicles have an amount of CD147 that is substantially the same as platelet derived extracellular vesicles (PLT EVs).

In embodiments, greater than about 50% of the megakaryocyte-derived extracellular vesicles comprise a lipid bilayer membrane comprising CD32a. In embodiments, greater than about 40% of the megakaryocyte-derived extracellular vesicles comprise a lipid bilayer membrane comprising CD32a. In embodiments, greater than about 60% of the megakaryocyte-derived extracellular vesicles comprise a lipid bilayer membrane comprising CD32a. In embodiments, greater than about 70% of the megakaryocyte-derived extracellular vesicles comprise a lipid bilayer membrane comprising CD32a. In embodiments, greater than about 80% of the megakaryocyte-derived extracellular vesicles comprise a lipid bilayer membrane comprising CD32a. In embodiments, greater than about 90% of the megakaryocyte-derived extracellular vesicles comprise a lipid bilayer membrane comprising CD32a. In embodiments, greater than about 95% of the megakaryocyte-derived extracellular vesicles comprise a lipid bilayer membrane comprising CD32a. In embodiments, greater than about 99% of the megakaryocyte-derived extracellular vesicles comprise a lipid bilayer membrane comprising CD32a.

In embodiments, about 50% or less of the megakaryocyte-derived extracellular vesicles comprise a lipid bilayer membrane comprising CD32a. In embodiments, about 40% or less of the megakaryocyte-derived extracellular vesicles comprise a lipid bilayer membrane comprising CD32a. In embodiments, about 60% or less of the megakaryocyte-derived extracellular vesicles comprise a lipid bilayer membrane comprising CD32a. In embodiments, about 70% or less of the megakaryocyte-derived extracellular vesicles comprise a lipid bilayer membrane comprising CD32a. In embodiments, about 80% or less of the megakaryocyte-derived extracellular vesicles comprise a lipid bilayer membrane comprising CD32a. In embodiments, about 90% or less of the megakaryocyte-derived extracellular vesicles comprise a lipid bilayer membrane comprising CD32a. In embodiments, about 95% or less of the megakaryocyte-derived extracellular vesicles comprise a lipid bilayer membrane comprising CD32a. In embodiments, about 99% or less of the megakaryocyte-derived extracellular vesicles comprise a lipid bilayer membrane comprising CD32a.

In embodiments, less than about 50% of the megakaryocyte-derived extracellular vesicles comprise a lipid bilayer membrane comprising CD32a. In embodiments, less than about 40% of the megakaryocyte-derived extracellular vesicles comprise a lipid bilayer membrane comprising CD32a. In embodiments, less than about 30% of the megakaryocyte-derived extracellular vesicles comprise a lipid bilayer membrane comprising CD32a. In embodiments, less than about 25% of the megakaryocyte-derived extracellular vesicles comprise a lipid bilayer membrane comprising CD32a. In embodiments, less than about 20% of the megakaryocyte-derived extracellular vesicles comprise a lipid bilayer membrane comprising CD32a. In embodiments, less than about 15% of the megakaryocyte-derived extracellular vesicles comprise a lipid bilayer membrane comprising CD32a. In embodiments, less than about 10% of the megakaryocyte-derived extracellular vesicles comprise a lipid bilayer membrane comprising CD32a. In embodiments, less than about 5% of the megakaryocyte-derived extracellular vesicles comprise a lipid bilayer membrane comprising CD32a. In embodiments, less than about 1% of the megakaryocyte-derived extracellular vesicles comprise a lipid bilayer membrane comprising CD32a.

In embodiments, between about 1% to about 99% of the megakaryocyte-derived extracellular vesicles comprise a lipid bilayer membrane comprising CD32a. In embodiments, between about 1% to about 50% of the megakaryocyte-derived extracellular vesicles comprise a lipid bilayer membrane comprising CD32a. In embodiments, between about 1% to about 25% of the megakaryocyte-derived extracellular vesicles comprise a lipid bilayer membrane comprising CD32a. In embodiments, between about 1% to about 10% of the megakaryocyte-derived extracellular vesicles comprise a lipid bilayer membrane comprising CD32a. In embodiments, between about 1% to about 5% of the megakaryocyte-derived extracellular vesicles comprise a lipid bilayer membrane comprising CD32a. In embodiments, between about 1% to about 2% of the megakaryocyte-derived extracellular vesicles comprise a lipid bilayer membrane comprising CD32a. In embodiments, between about 50% to about 99% of the megakaryocyte-derived extracellular vesicles comprise a lipid bilayer membrane comprising CD32a. In embodiments, between about 75% to about 99% of the megakaryocyte-derived extracellular vesicles comprise a lipid bilayer membrane comprising CD32a. In embodiments, between about 90% to about 99% of the megakaryocyte-derived extracellular vesicles comprise a lipid bilayer membrane comprising CD32a. In embodiments, between about 95% to about 99% of the megakaryocyte-derived extracellular vesicles comprise a lipid bilayer membrane comprising CD32a.

In embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD32a.

In embodiments, the megakaryocyte-derived extracellular vesicles are free of, or substantially free of CD32a.

In embodiments, the megakaryocyte-derived extracellular vesicles are characterized by a higher expression and/or presence of CD32a than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD32a than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD32a than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD32a than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 50-fold to about 100-fold, 128-fold to about a 512-fold, or about a 256-fold to about a 512-fold, or about a 250-fold to about a 300-fold lower amount of CD32a than platelet free plasma (PFP) MkEVs. In embodiments, the megakaryocyte-derived extracellular vesicles have about a 250-fold or about a 256-fold lower amount of CD32a than platelet free plasma (PFP) MkEVs. In embodiments, the megakaryocyte-derived extracellular vesicles have about a 250-fold to about a 400-fold, or a 256-fold to about a 512-fold lower amount of CD32a than platelet derived extracellular vesicles (PLT EVs). In embodiments, the megakaryocyte-derived extracellular vesicles have about a 256-fold or about a 300-fold lower amount of CD32a than platelet derived extracellular vesicles (PLT EVs).

In embodiments, greater than about 50% of the megakaryocyte-derived extracellular vesicles comprise a lipid bilayer membrane comprising GPVI. In embodiments, greater than about 40% of the megakaryocyte-derived extracellular vesicles comprise a lipid bilayer membrane comprising GPVI. In embodiments, greater than about 60% of the megakaryocyte-derived extracellular vesicles comprise a lipid bilayer membrane comprising GPVI. In embodiments, greater than about 70% of the megakaryocyte-derived extracellular vesicles comprise a lipid bilayer membrane comprising GPVI a. In embodiments, greater than about 80% of the megakaryocyte-derived extracellular vesicles comprise a lipid bilayer membrane comprising GPVI. In embodiments, greater than about 90% of the megakaryocyte-derived extracellular vesicles comprise a lipid bilayer membrane comprising GPVI. In embodiments, greater than about 95% of the megakaryocyte-derived extracellular vesicles comprise a lipid bilayer membrane comprising GVPI. In embodiments, greater than about 99% of the megakaryocyte-derived extracellular vesicles comprise a lipid bilayer membrane comprising GVPI.

In embodiments, about 50% or less of the megakaryocyte-derived extracellular vesicles comprise a lipid bilayer membrane comprising GVPI. In embodiments, about 40% or less of the megakaryocyte-derived extracellular vesicles comprise a lipid bilayer membrane comprising GVPI. In embodiments, about 60% or less of the megakaryocyte-derived extracellular vesicles comprise a lipid bilayer membrane comprising GVPI. In embodiments, about 70% or less of the megakaryocyte-derived extracellular vesicles comprise a lipid bilayer membrane comprising GVPI. In embodiments, about 80% or less of the megakaryocyte-derived extracellular vesicles comprise a lipid bilayer membrane comprising GVPI. In embodiments, about 90% or less of the megakaryocyte-derived extracellular vesicles comprise a lipid bilayer membrane comprising GVPI. In embodiments, about 95% or less of the megakaryocyte-derived extracellular vesicles comprise a lipid bilayer membrane comprising GVPI. In embodiments, about 99% or less of the megakaryocyte-derived extracellular vesicles comprise a lipid bilayer membrane comprising GVPI.

In embodiments, less than about 50% of the megakaryocyte-derived extracellular vesicles comprise a lipid bilayer membrane comprising GVPI. In embodiments, less than about 40% of the megakaryocyte-derived extracellular vesicles comprise a lipid bilayer membrane comprising GVPI. In embodiments, less than about 30% of the megakaryocyte-derived extracellular vesicles comprise a lipid bilayer membrane comprising GVPI. In embodiments, less than about 25% of the megakaryocyte-derived extracellular vesicles comprise a lipid bilayer membrane comprising GVPI. In embodiments, less than about 20% of the megakaryocyte-derived extracellular vesicles comprise a lipid bilayer membrane comprising GVPI. In embodiments, less than about 15% of the megakaryocyte-derived extracellular vesicles comprise a lipid bilayer membrane comprising GVPI. In embodiments, less than about 10% of the megakaryocyte-derived extracellular vesicles comprise a lipid bilayer membrane comprising GVPI. In embodiments, less than about 5% of the megakaryocyte-derived extracellular vesicles comprise a lipid bilayer membrane comprising GVPI. In embodiments, less than about 1% of the megakaryocyte-derived extracellular vesicles comprise a lipid bilayer membrane comprising GVPI.

In embodiments, between about 1% to about 99% of the megakaryocyte-derived extracellular vesicles comprise a lipid bilayer membrane comprising GVPI. In embodiments, between about 1% to about 50% of the megakaryocyte-derived extracellular vesicles comprise a lipid bilayer membrane comprising GVPI. In embodiments, between about 1% to about 25% of the megakaryocyte-derived extracellular vesicles comprise a lipid bilayer membrane comprising GVPI. In embodiments, between about 1% to about 10% of the megakaryocyte-derived extracellular vesicles comprise a lipid bilayer membrane comprising GVPI. In embodiments, between about 1% to about 5% of the megakaryocyte-derived extracellular vesicles comprise a lipid bilayer membrane comprising GVPI. In embodiments, between about 1% to about 2% of the megakaryocyte-derived extracellular vesicles comprise a lipid bilayer membrane comprising GVPI. In embodiments, between about 50% to about 99% of the megakaryocyte-derived extracellular vesicles comprise a lipid bilayer membrane comprising GVPI. In embodiments, between about 75% to about 99% of the megakaryocyte-derived extracellular vesicles comprise a lipid bilayer membrane comprising GVPI. In embodiments, between about 90% to about 99% of the megakaryocyte-derived extracellular vesicles comprise a lipid bilayer membrane comprising GVPI. In embodiments, between about 95% to about 99% of the megakaryocyte-derived extracellular vesicles comprise a lipid bilayer membrane comprising GVPI.

In embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising GVPI.

In embodiments, the megakaryocyte-derived extracellular vesicles are characterized by a higher expression and/or presence of GPVI than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of GPVI than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of GPVI than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of GPVI than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about an 8-fold to about a 64-fold, or about a 16-fold to about a 32-fold greater amount of GPVI than platelet free plasma (PFP) MkEVs. In embodiments, the megakaryocyte-derived extracellular vesicles have about a 30-fold or about a 32-fold greater amount of GPVI than platelet free plasma (PFP) MkEVs. In embodiments, the megakaryocyte-derived extracellular vesicles have about a 2-fold to about a 16-fold, or about a 4-fold to about an 8-fold lower amount of GPVI than platelet derived extracellular vesicles (PLT EVs). In embodiments, the megakaryocyte-derived extracellular vesicles have about a 4-fold or about a 5-fold lower amount of GPVI than platelet derived extracellular vesicles (PLT EVs).

In embodiments, the megakaryocyte-derived extracellular vesicles are free of, or substantially free of LAMP-1 (CD107A). In embodiments, the megakaryocyte-derived extracellular vesicles have less LAMP-1 (CD107A) than naturally-occurring megakaryocyte-derived extracellular vesicles and/or vesicles or extracellular vesicles derived from platelets.

In embodiments, less than about 20%, or less than about 15%, or less than about 10%, or less than about 5% of the megakaryocyte-derived extracellular vesicles comprise a lipid bilayer membrane comprising LAMP-1 (CD107A).

In embodiments, the megakaryocyte-derived extracellular vesicles are characterized by having CD62P and being free of, or substantially free of LAMP-1 (CD107A).

In embodiments, the megakaryocyte-derived extracellular vesicles are characterized by a population of megakaryocyte-derived extracellular vesicles wherein less than about 20%, or less than about 15%, or less than about 10%, or less than about 5% of the megakaryocyte-derived extracellular vesicles comprise a lipid bilayer membrane comprising LAMP-1 (CD107A) and greater than about 40%, greater than about 50%, greater than about 60%, greater than about 70%, greater than about 80%, greater than about 90%, greater than about 95%, or greater than about 99% comprises a lipid bilayer membrane comprising CD62P.

In embodiments, less than about 70%, or less than about 60%, or less than about 50%, less than about 40%, less than about 30%, less than about 20%, less than about 15%, less than about 10%, less than about 5%, or less than about 1% of the megakaryocyte-derived extracellular vesicles comprise a lipid bilayer membrane comprising phosphatidylserine (PS).

In embodiments, the megakaryocyte-derived extracellular vesicles are characterized by a lower expression and/or presence of phosphatidylserine (PS) than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of phosphatidylserine (PS) than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by being free of, or substantially free of phosphatidylserine (PS).

In embodiments, the megakaryocyte-derived extracellular vesicles are characterized by a population of megakaryocyte-derived extracellular vesicles wherein less than about 50%, less than about 40%, less than about 30%, less than about 20%, less than about 15%, less than about 10%, less than about 5%, or less than about 1% of the megakaryocyte-derived extracellular vesicles comprise a lipid bilayer membrane comprising phosphatidylserine (PS), and greater than about 40%, greater than about 50%, greater than about 60%, greater than about 70%, greater than about 80%, greater than about 90%, greater than about 95%, or greater than about 99% of the megakaryocyte-derived extracellular vesicles comprise a lipid bilayer membrane comprising CD47.

In embodiments, the megakaryocyte-derived extracellular vesicles are characterized by a population of megakaryocyte-derived extracellular vesicles wherein about 20% to about 40% of the megakaryocyte-derived extracellular vesicles comprise a lipid bilayer membrane comprising and/or test positive for phosphatidylserine (PS), about 80% to about 99%, or about 85% to about 99% of the megakaryocyte-derived extracellular vesicles comprise a lipid bilayer membrane comprising CD61, and about 25% to about 55%, or about 35% to about 55% of the megakaryocyte-derived extracellular vesicles comprise a lipid bilayer membrane comprising CD9.

In embodiments, the megakaryocyte-derived extracellular vesicles are characterized by a higher expression and/or presence or CD41 than naturally-occurring megakaryocyte-derived extracellular vesicles and/or vesicles or extracellular vesicles derived from platelets. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD41 than naturally-occurring megakaryocyte-derived extracellular vesicles and/or vesicles or extracellular vesicles derived from platelets.

In embodiments, the megakaryocyte-derived extracellular vesicles are characterized by a lower expression and/or presence or CD41 than naturally-occurring megakaryocyte-derived extracellular vesicles and/or vesicles or extracellular vesicles derived from platelets. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD41 than naturally-occurring megakaryocyte-derived extracellular vesicles and/or vesicles or extracellular vesicles derived from platelets.

In embodiments, the megakaryocyte-derived extracellular vesicles contain full-length filamin A.

In embodiments, the megakaryocyte-derived extracellular vesicles comprise a lipid bilayer membrane that comprises phosphatidylserine. In embodiments, the megakaryocyte-derived extracellular vesicles are characterized by a population of megakaryocyte-derived extracellular vesicles of which greater than about 40%, greater than about 50%, greater than about 60%, greater than about 70%, greater than about 80%, greater than about 90%, greater than about 95%, or greater than about 99% comprises a lipid bilayer membrane that comprises phosphatidylserine.

In embodiments, the megakaryocyte-derived extracellular vesicles comprise a lipid bilayer membrane positive for Annexin V. For instance, Annexin V, which interacts with phosphatidylserine (PS), can be used as a surrogate for phosphatidylserine expression and/or presence or absence. In embodiments, the megakaryocyte-derived extracellular vesicles are characterized by a population of megakaryocyte-derived extracellular vesicles of which greater than about 40%, greater than about 50%, greater than about 60%, greater than about 70%, greater than about 80%, greater than about 90%, or greater than about 95% are positive for PS.

In embodiments, the megakaryocyte-derived extracellular vesicles are characterized by a population of megakaryocyte-derived extracellular vesicles of which about 20% to about 40% comprises a lipid bilayer membrane that comprises phosphatidylserine and/or are positive for phosphatidylserine.

In embodiments, substantially all of the megakaryocyte-derived extracellular vesicles in the population comprise 2, 3, 4, 5, 6, 7, or 8 of Phosphatidylserine (PS), CD62P, LAMP-1 (CD107a), CD42b, CD9, CD43, CD31, and CD11b. In embodiments, substantially all of the megakaryocyte-derived extracellular vesicles in the population comprise 2, 3, or 4 of PS, CD62P, CD9, and CD11b. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of one or more of Phosphatidylserine (PS), CD62P, LAMP-1 (CD107a), CD42b, CD9, CD43, CD31, and CD11b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles are characterized by not expressing a substantial amount of DRAQ5. In embodiments, the megakaryocyte-derived extracellular vesicles are characterized by being substantially free of DRAQ5.

In embodiments, substantially all of the megakaryocyte-derived extracellular vesicles in the population comprise 2, 3, 4, 5, or 6 of Phosphatidylserine (PS), CD61, CD62P, LAMP-1 (CD107a), CLEC-2, and CD63. In embodiments, substantially all of the megakaryocyte-derived extracellular vesicles in the population comprise 2 or 3 of PS, CD61, and CD63. In embodiments, substantially all of the megakaryocyte-derived extracellular vesicles in the population comprise Phosphatidylserine (PS) and CD61. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of one or more of Phosphatidylserine (PS), CD61, CD62P, LAMP-1 (CD107a), CLEC-2, and CD63 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles are characterized by not expressing a substantial amount of DRAQ5. In embodiments, the megakaryocyte-derived extracellular vesicles are characterized by being substantially free of DRAQ5.

In embodiments, substantially all of the megakaryocyte-derived extracellular vesicles in the population comprise 2, 3, 4, 5, 6, 7, or 8 of Phosphatidylserine (PS), CD62P, CLEC-2, CD9, CD31, CD147, CD32a, and GPVI. In embodiments, substantially all of the megakaryocyte-derived extracellular vesicles in the population comprise 2, 3, or 4 of Phosphatidylserine (PS), CD9, CD31, and CD147. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of one or more of Phosphatidylserine (PS), CD62P, CLEC-2, CD9, CD31, CD147, CD32a, and GPVI than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles are characterized by not expressing a substantial amount of DRAQ5. In embodiments, the megakaryocyte-derived extracellular vesicles are characterized by being substantially free of DRAQ5.

In embodiments, substantially all of the megakaryocyte-derived extracellular vesicles in the population comprise 2, 3, 4, 5, of 6 of Phosphatidylserine (PS), CD62P, LAMP-1 (CD107a), CLEC-2, CD9, and CD31. In embodiments, substantially all of the megakaryocyte-derived extracellular vesicles in the population comprise 2 or 3 of Phosphatidylserine (PS), CD62P, and CD9. In embodiments, substantially all of the megakaryocyte-derived extracellular vesicles in the population comprise PS and CD9. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of one or more of Phosphatidylserine (PS), CD62P, LAMP-1 (CD107a), CLEC-2, CD9, and CD31 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles are characterized by not expressing a substantial amount of DRAQ5. In embodiments, the megakaryocyte-derived extracellular vesicles are characterized by being substantially free of DRAQ5.

In embodiments, the megakaryocyte-derived extracellular vesicles and/or plurality of megakaryocyte-derived extracellular vesicles and/or population of megakaryocyte-derived extracellular vesicles comprise a lipid bilayer membrane, wherein less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD54, and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD18 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD43 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD11 b and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD62P and/or greater than about 40%, or greater than about 50%, or greater than about 60%, or greater than about 70%, or greater than about 80%, or greater than about 90%, greater than about 95%, or greater than about 99% of the megakaryocyte-derived extracellular vesicles comprise a lipid bilayer membrane comprising CD41 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD21 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD51 and/or greater than about 40%, or greater than about 50%, or greater than about 60%, or greater than about 70%, or greater than about 80%, or greater than about 90%, greater than about 95%, or greater than about 99% of the megakaryocyte-derived extracellular vesicles comprise a lipid bilayer membrane comprising CD61 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD147 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD31 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD47 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD32a and/or greater than about 40%, or greater than about 50%, or greater than about 60%, or greater than about 70%, or greater than about 80%, or greater than about 90%, greater than about 95%, or greater than about 99% of the megakaryocyte-derived extracellular vesicles comprise a lipid bilayer membrane comprising CD9 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CLEC-2 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising LAMP-1 (CD107a) and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD24b and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising GVPI and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD63, and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising phosphatidylserine (PS). In embodiments, greater than about 40%, greater than about 50%, or greater than about 60%, or greater than about 70%, or greater than about 80%, or greater than about 90%, greater than about 95%, or greater than about 99% of the megakaryocyte-derived extracellular vesicles and/or plurality of megakaryocyte-derived extracellular vesicles and/or population of megakaryocyte-derived extracellular vesicles comprise a lipid bilayer membrane comprising CD41.

Size Profile or Fingerprint

In various embodiments, the megakaryocyte-derived extracellular vesicles of the disclosure are characterized by a unique size (e.g. vesicle diameter) profile or fingerprint that distinguishes them from, for instance, naturally-occurring megakaryocyte-derived extracellular vesicles and/or vesicles or extracellular vesicles derived from platelets. In various embodiments, the present megakaryocyte-derived extracellular vesicles are characterized by a such a size profile or fingerprint, which favors larger particles, e.g. as compared to naturally-occurring megakaryocyte-derived extracellular vesicles and/or vesicles or extracellular vesicles derived from platelets, that are desirable for, e.g., their higher carrying capacity.

In various embodiments, the present megakaryocyte-derived extracellular vesicles are characterized by a bias for particles of about 30 nm to about 100 nm.

In various embodiments, the present megakaryocyte-derived extracellular vesicles are characterized by a bias for particles of about 30 nm to about 400 nm.

In various embodiments, the present megakaryocyte-derived extracellular vesicles are characterized by a bias for particles of about 100 nm to about 200 nm.

In various embodiments, the present megakaryocyte-derived extracellular vesicles are characterized by a bias for particles of about 100 nm to about 300 nm.

In various embodiments, the present megakaryocyte-derived extracellular vesicles are characterized by a bias for particles of about 100 nm to about 500 nm.

In various embodiments, the present megakaryocyte-derived extracellular vesicles are characterized by a bias for particles of about 100 nm to about 600 nm.

In various embodiments, the present megakaryocyte-derived extracellular vesicles are characterized by a bias for particles of about 200 nm in diameter, on average.

In various embodiments, the present megakaryocyte-derived extracellular vesicles are characterized by a bias for particles of about 250 nm in diameter, on average.

In embodiments, the megakaryocyte-derived extracellular vesicles are substantially of a diameter of less than about 100 nm. In embodiments, the megakaryocyte-derived extracellular vesicles are substantially of a diameter in the range between about 30 nm to about 300 nm. In embodiments, the megakaryocyte-derived extracellular vesicles are substantially of a diameter in the range between about 30 nm to about 400 nm. In embodiments, the megakaryocyte-derived extracellular vesicles are substantially of a diameter in the range between about 100 nm to about 300 nm. In embodiments, the megakaryocyte-derived extracellular vesicles are substantially of a diameter in the range between about 200 nm to about 300 nm. In embodiments, the megakaryocyte-derived extracellular vesicles are substantially of a diameter in the range between about 300 nm to about 400 nm. In embodiments, the megakaryocyte-derived extracellular vesicles are substantially of a diameter in the range between about 400 nm to about 500 nm. In embodiments, the megakaryocyte-derived extracellular vesicles are substantially of a diameter in the range between about 500 nm to about 600 nm. In embodiments, the megakaryocyte-derived extracellular vesicles are substantially of a diameter in the range between about 600 nm to about 700 nm. In embodiments, the megakaryocyte-derived extracellular vesicles are substantially of a diameter in the range between about 700 nm to about 800 nm. In embodiments, the megakaryocyte-derived extracellular vesicles are substantially of a diameter in the range between about 800 nm to about 900 nm. In embodiments, the megakaryocyte-derived extracellular vesicles are substantially of a diameter in the range between about 900 nm to about 1000 nm. In embodiments, the megakaryocyte-derived extracellular vesicles are substantially of a diameter in the range between about 500 nm to about 1000 nm. In embodiments, the megakaryocyte-derived extracellular vesicles are substantially of a diameter in the range between about 600 nm to about 1000 nm. In embodiments, the megakaryocyte-derived extracellular vesicles are substantially of a diameter in the range between about 100 nm to about 500 nm. In embodiments, the megakaryocyte-derived extracellular vesicles are substantially of a diameter in the range between about 100 nm to about 600 nm. In embodiments, the megakaryocyte-derived extracellular vesicles are substantially of a diameter in the range between about 150 nm to about 500 nm. In embodiments, the megakaryocyte-derived extracellular vesicles are substantially of a diameter in the range between about 100 nm to about 200 nm. In embodiments, the megakaryocyte-derived extracellular vesicles are substantially of a diameter in the range between about 100 nm to about 200 nm. In embodiments, the megakaryocyte-derived extracellular vesicles are substantially of a diameter in the range between about 200 nm to about 600 nm. In embodiments, the megakaryocyte-derived extracellular vesicles are substantially of a diameter in the range between about 30 nm to 100 nm, or between about 30 nm to 400 nm, or between about 100 nm to about 200 nm, or between about 100 nm to about 500 nm, or between about 200 nm to about 350 nm, or between about 400 nm to about 600 nm.

In embodiments, about 90% or more, or about 95% or more, or about 97% or more, or about 99% or more of the megakaryocyte-derived extracellular vesicles are of a diameter of between about 30 to 100 nm.

In embodiments, about 90% or more, or about 95% or more, or about 97% or more, or about 99% or more of the megakaryocyte-derived extracellular vesicles are of a diameter of between about 30 to 400 nm.

In embodiments, about 90% or more, or about 95% or more, or about 97% or more, or about 99% or more of the megakaryocyte-derived extracellular vesicles are of a diameter of between about 100 nm to about 200 nm.

In embodiments, about 90% or more, or about 95% or more, or about 97% or more, or about 99% or more of the megakaryocyte-derived extracellular vesicles are of a diameter of between about 100 nm to about 300 nm.

In embodiments, about 90% or more, or about 95% or more, or about 97% or more, or about 99% or more of the megakaryocyte-derived extracellular vesicles are of a diameter of between about 200 nm to about 350 nm.

In embodiments, about 90% or more, or about 95% or more, or about 97% or more, or about 99% or more of the megakaryocyte-derived extracellular vesicles are of a diameter of between about 100 nm to about 600 nm.

In embodiments, about 90% or more, or about 95% or more, or about 97% or more, or about 99% or more of the megakaryocyte-derived extracellular vesicles are of a diameter of between about 400 nm to about 600 nm.

In embodiments, about 90% or more, or about 95% or more, or about 97% or more, or about 99% or more of the megakaryocyte-derived extracellular vesicles are of a diameter of between about 200 nm to about 600 nm.

In embodiments, about 90% or more, or about 95% or more, or about 97% or more, or about 99% or more of the megakaryocyte-derived extracellular vesicles are of a diameter of between about 30 to about 100 nm and/or about 30 to about 400 nm and/or about 100 nm to about 200 nm and/or about 100 nm to about 300 nm and/or between about 200 nm to about 350 nm and/or between about 400 nm to about 600 nm.

In embodiments, the megakaryocyte-derived extracellular vesicles of the disclosure comprise various subpopulations of vesicles of different diameter. For example, in embodiments, megakaryocyte-derived extracellular vesicles of the disclosure comprise one or more of (e.g. one, or two, or three, or four of): a subpopulation of about 50 nm in diameter, a subpopulation of about 150 nm in diameter, a subpopulation of about 200 nm in diameter, a subpopulation of about 250 nm in diameter, a subpopulation of about 300 nm in diameter, a subpopulation of about 400 nm in diameter, a subpopulation of about 500 nm in diameter and a subpopulation of about 600 nm in diameter. In embodiments, megakaryocyte-derived extracellular vesicles of the disclosure comprise one or more of (e.g. one, or two, or three, or four of): a subpopulation of about 45 nm in diameter, a subpopulation of about 135 nm in diameter, a subpopulation of about 285 nm in diameter, and a subpopulation of about 525 nm in diameter.

In embodiments, about 90% or more, or about 95% or more, or about 97% or more, or about 99% or more of the megakaryocyte-derived extracellular vesicles are of about 50 nm in diameter and/or about 150 nm in diameter and/or about 300 nm in diameter and/or about 500 nm in diameter.

In embodiments, the population of megakaryocyte-derived extracellular vesicles exhibits the following characteristics:

a) about 80% or more, about 85% or more, about 90% or more, about 95% or more, about 97% or more, or about 99% or more of the megakaryocyte-derived extracellular vesicles in the population are substantially free of nuclei;
b) about 90% or more, or about 95% or more, or about 97% or more, or about 99% or more of the megakaryocyte-derived extracellular vesicles are of a diameter of between about 100 nm to about 600 nm;
c) about 40% or more, about 50% or more, about 60% or more, about 70% or more, about 80% or more, or about 90% or more of the megakaryocyte-derived extracellular vesicles in the population comprise CD41; and
d) the population comprises about $1\times10^7$ or more, about $1.5\times10^7$ or more, about $5\times10^7$ or more, about $1\times10^8$ or more, about $1.5\times10^8$ or more, about $5\times10^8$ or more, about $1\times10^9$ or more, about $5\times10^9$ or more, about $1\times10^{10}$ or more, or about $1\times10^{10}$ or more megakaryocyte-derived extracellular vesicles.

In embodiments, the population of megakaryocyte-derived extracellular vesicles exhibits the following characteristics:

a) about 80% or more, about 85% or more, about 90% or more, about 95% or more, about 97% or more, or about 99% or more of the megakaryocyte-derived extracellular vesicles in the population are substantially free of nuclei;
b) about 90% or more, or about 95% or more, or about 97% or more, or about 99% or more of the megakaryocyte-derived extracellular vesicles are of a diameter of between about 100 nm to about 600 nm;
c) about 40% or more, about 50% or more, about 60% or more, about 70% or more, about 80% or more, or about 90% or more of the megakaryocyte-derived extracellular vesicles in the population comprise CD61; and
d) the population comprises about $1\times10^7$ or more, about $1.5\times10^7$ or more, about $5\times10^7$ or more, about $1\times10^8$ or more, about $1.5\times10^8$ or more, about $5\times10^8$ or more, about $1\times10^9$ or more, about $5\times10^9$ or more, about $1\times10^{10}$ or more, or about $1\times10^{10}$ or more megakaryocyte-derived extracellular vesicles.

Any method for determining the amount of nuclei in the population of megakaryocyte-derived extracellular vesicles is contemplated by the present disclosure. Non-limiting examples of methods include staining the megakaryocyte-derived extracellular vesicles with a nuclear stain such as DRAQ5, wherein a lack of staining indicates that the megakaryocyte-derived extracellular vesicles are substantially free of nuclei.

Sources and Characterization of Megakaryocyte-Derived Extracellular Vesicles

Megakaryocytes are large, polyploid cells derived from hematopoietic stem and progenitor cells, contained within the $CD34^+$-cell compartment. In embodiments, the megakaryocyte is characterized by the expression and/or presence of one or more of CD41, CD62P, GPVI, CLEC-2, CD42b and CD61. In embodiments, the megakaryocyte is one or more of CD42b+, CD61+, and DNA+. One morphological characteristic of mature megakaryocytes is the development of a large, multi-lobed nucleus. Mature megakaryocytes can stop proliferating, but continue to increase their DNA content through endomitosis, with a parallel increase in cell size.

In embodiments, in addition to extracellular vesicles, megakaryocytes can shed pre- and proplatelets and platelet-like particles. These shed moieties can mature into platelets. In embodiments, the pre- and proplatelets and platelet-like particles are all different products, which can be differentiated by size, morphology, biomarker expression and/or presence, and function.

Megakaryocytes are derived from pluripotent hematopoietic stem cell (HSC) precursors. HSCs are produced primarily by the liver, kidney, spleen, and bone marrow and are capable of producing a variety of blood cells depending on the signals they receive.

Thrombopoietin (TPO) is a primary signal for inducing an HSC to differentiate into a megakaryocyte. Other molecular signals for inducing megakaryocyte differentiation include granulocyte-macrophage colony-stimulating factor (GM-CSF), Interleukin-3 (IL-3), IL-6, IL-11, SCF, fms-like tyrosine kinase 3 ligand (FLT3L), interleukin 9 (IL-9), and the like. Production details are also described elsewhere herein.

In embodiments, the substantially purified megakaryocyte-derived extracellular vesicles are derived from a human pluripotent stem cell.

In embodiments, the human pluripotent stem cell is a primary CD34+ hematopoietic stem cell. In embodiments, the primary CD34+ hematopoietic stem cell is sourced from peripheral blood or cord blood. In embodiments, the peripheral blood is granulocyte colony-stimulating factor-mobilized adult peripheral blood (mPB). In embodiments, the human pluripotent stem cell is an HSC produced by the liver, kidney, spleen, or bone marrow. In embodiments, the HSC is produced by the liver. In embodiments, the HSC is produced by the kidney. In embodiments, the HSC is produced by the spleen. In embodiments, the HSC is produced by the bone marrow. In embodiments, the HSC is induced to differentiate into a megakaryocyte by receiving a molecular signal selected from one or more of TPO, GM-CSF, IL-3, IL-6, IL-11, SCF, FIt3L, IL-9, and the like. In embodiments, the molecular signal is TPO. In embodiments, the molecular signal is GM-CSF. In embodiments, the molecular signal is IL-3. In embodiments, the molecular signal is IL-6. In embodiments, the molecular signal is IL-11. In embodiments, the molecular signal is IL-6. In embodiments, the molecular signal is SCF. In embodiments, the molecular signal is IL-6.SCF. In embodiments, the molecular signal is FIt3L. In embodiments, the molecular signal is IL-6. In embodiments, the molecular signal is IL-9.

In embodiments, the molecular signal is a chemokine.

In embodiments, the molecular signal promotes cell fate decision toward megakaryopoiesis.

In embodiments, the molecular signal is devoid of erythropoietin (EPO).

In embodiments, the human pluripotent stem cell is an embryonic stem cell (ESC). ESCs have the capacity to form cells from all three germ layers of the body, regardless of the method by which the ESCs are derived. ESCs are functionally stem cells that can have one or more of the following characteristics: (a) be capable of inducing teratomas when transplanted in immunodeficient mice; (b) be capable of differentiating to cell types of all three germ layers (i.e. ectodermal, mesodermal, and endodermal cell types); and (c) express one or more markers of embryonic stem cells (e.g., Oct 4, alkaline phosphatase. SSEA-3 surface antigen, SSEA-4 surface antigen, SSEA-5 surface antigen, Nanog, TRA-I-60, TRA-1-81, SOX2, REX1, and the like).

In embodiments, the human pluripotent stem cell is an induced pluripotent stem cell (iPCs). Mature differentiated cells can be reprogrammed and dedifferentiated into embryonic-like cells, with embryonic stem cell-like properties. iPSCs can be generated using fetal, postnatal, newborn, juvenile, or adult somatic cells. Fibroblast cells can be reversed into pluripotency via, for example, retroviral transduction of certain transcription factors, resulting in iPSs. In embodiments, iPSs are generated from various tissues, including fibroblasts, keratinocytes, melanocyte blood cells, bone marrow cells, adipose cells, and tissue-resident progenitor cells. In embodiments, iPSCs are generated via one or more reprogramming or Yamanaka factors, e.g. Oct3/4, Sox2, Klf4, and c-Myc. In certain embodiments, at least two, three, or four reprogramming factors are expressed in a somatic cell to reprogram the somatic cell.

Once a pluripotent cell has completed differentiation and become a mature megakaryocyte, it begins the process of producing platelets, which do not contain a nucleus and may be about 1-3 um in diameter. Megakaryocytes also produce extracellular vesicles.

In embodiments, the present megakaryocytes are induced to favor production of megakaryocyte-derived extracellular vesicles over platelets. That is, in embodiments, the present megakaryocytes produce substantially more megakaryocyte-derived extracellular vesicles than platelets. In embodiments, the megakaryocyte-derived extracellular vesicles of the disclosure are substantially free of platelets. In embodiments, the megakaryocyte-derived extracellular vesicles of the disclosure contain less than about 10%, or less than about 7%, or less than about 5%, or less than about 3%, or less than about 2%, or less than about 1% platelets.

In embodiments, the megakaryocyte-derived extracellular vesicles of the disclosure are substantially free of extracellular vesicles derived from platelets. In embodiments, the megakaryocyte-derived extracellular vesicles of the disclosure contain less than about 10%, or less than about 7%, or less than about 5%, or less than about 3%, or less than about 2%, or less than about 1% of extracellular vesicles derived from platelets.

In embodiments, the megakaryocyte-derived extracellular vesicles of the disclosure are substantially free of organelles. Non-limiting examples of contaminating organelles include, but are not limited to, mitochondria, and nuclei. In embodiments, the megakaryocyte-derived extracellular vesicles of the disclosure are substantially free of mitochondria. In embodiments, the preparation comprising the megakaryocyte-derived extracellular vesicles of the disclosure is substantially free of exosomes. In embodiments, megakaryocyte-derived extracellular vesicles of the disclosure comprise organelles.

In embodiments, the megakaryocyte-derived extracellular vesicles of the disclosure are substantially free of nuclei. In embodiments, about 80% to about 100%, about 85% to about 100%, about 90% to about 100%, or about 95% to about 100% of the megakaryocyte-derived extracellular vesicles in the population are substantially free of nuclei. In embodiments, greater than about 80%, greater than about 85%, greater than about 90%, greater than about 95%, greater than about 99%, or about 100% of the megakaryocyte-derived extracellular vesicles in the population are substantially free of nuclei.

Targeting

Megakaryocyte-derived extracellular vesicles can home to a range of target cells. When megakaryocyte-derived extracellular vesicles bind to a target cell, they can release their cargo via various mechanisms of megakaryocyte-derived extracellular vesicle internalization by the target cell.

In embodiments, the megakaryocyte-derived extracellular vesicles are suitable for homing to bone marrow in vivo. In embodiments, the megakaryocyte-derived extracellular vesicles are suitable for homing to bone marrow in vitro. In embodiments, the megakaryocyte-derived extracellular vesicles home in vivo to bone marrow with about a 2-fold, or about a 3-fold, or about a 4-fold, or about a 5-fold, or about a 6-fold, or about a 7-fold, or about a 8-fold, or about a 9-fold, or about a 10-fold greater specificity than to another cell type, or to another organ, or to all other cell types combined.

In embodiments, the megakaryocyte-derived extracellular vesicles home in vivo to one or more myelopoeitic cells in bone marrow. In embodiments, the one or more myelopoeitic cells are selected from myeloblasts, promyelocytes, neutrophilic myelocytes, eosinophilic myelocytes, neutrophilic metamyelocytes, eosinophilic metamyelocytes, neutrophilic band cells, eosinophilic band cells, segmented neutrophils, segmented eosinophils, segmented basophils, and mast cells. In embodiments, the megakaryocyte-derived extracellular vesicles home in vivo to one or more erythropoietic cells in bone marrow. In embodiments, the one or more erythropoietic cells are selected from pronormoblasts, basophilic normoblasts, polychromatic normoblasts, and orthochromatic normoblasts. In embodiments, the megakaryocyte-derived extracellular vesicles home in vivo to one or more of plasma cells, reticular cells, lymphocytes, monocytes, and megakaryocytes.

In embodiments, the megakaryocyte-derived extracellular vesicles home in vivo to one or more hematopoietic cells in bone marrow. In embodiments, the megakaryocyte-derived extracellular vesicles home in vivo to one or more hematopoietic cells in bone marrow, e.g. thrombopoietic cells.

In embodiments, the megakaryocyte-derived extracellular vesicles home in vivo to one or more hematopoietic stem cells in bone marrow.

In embodiments, the megakaryocyte-derived extracellular vesicles are suitable for homing to an HSC in vivo. In embodiments, the megakaryocyte-derived extracellular vesicles are suitable for homing to an HSC in vitro. In embodiments, the megakaryocyte-derived extracellular vesicles home in vivo to an HSC with about a 2-fold greater specificity than to another cell type, or than to another organ, or than to all other cell types combined. In embodiments, the megakaryocyte-derived extracellular vesicles home in vivo to an HSC with about a 3-fold greater specificity than to another cell type, or than to another organ, or than to all other cell types combined. In embodiments, the megakaryocyte-derived extracellular vesicles home in vivo to an HSC with about a 4-fold greater specificity than to another cell type, or to another organ, or to all other cell types combined. In embodiments, the megakaryocyte-derived extracellular vesicles home in vivo to an HSC with about a 5-fold greater specificity than to another cell type, or to another organ, or to all other cell types combined. In embodiments, the megakaryocyte-derived extracellular vesicles home in vivo to an HSC with about a 6-fold greater specificity than to another cell type, or to another organ, or to all other cell types combined. In embodiments, the megakaryocyte-derived extracellular vesicles home in vivo to an HSC with about a 7-fold greater specificity than to another cell type, or to another organ, or to all other cell types combined. In embodiments, the megakaryocyte-derived extracellular vesicles home in vivo to an HSC with about a 8-fold greater specificity than to another cell type, or to another organ, or to all other cell types combined. In embodiments, the megakaryocyte-derived extracellular vesicles home in vivo to an HSC with about a 9-fold greater specificity than to another cell type, or to another organ, or to all other cell types combined. In embodiments, the megakaryocyte-derived extracellular vesicles home in vivo to an HSC with about a 10-fold greater specificity than to another cell type, or to another organ, or to all other cell types combined.

In embodiments, the megakaryocyte-derived extracellular vesicles are suitable for homing to a lymphatic cell in vivo. In embodiments, the megakaryocyte-derived extracellular vesicles are suitable for homing to a lymphatic cell in vitro. In embodiments, the megakaryocyte-derived extracellular vesicles home in vivo to a lymphatic cell with about a 2-fold greater specificity than to another cell type, or to another organ, or to all other cell types combined. In embodiments, the megakaryocyte-derived extracellular vesicles home in vivo to a lymphatic cell with about a 3-fold greater specificity than to another cell type, or to another organ, or to all other cell types combined. In embodiments, the megakaryocyte-derived extracellular vesicles home in vivo to a lymphatic cell with about a 4-fold greater specificity than to another cell type, or to another organ, or to all other cell types combined. In embodiments, the megakaryocyte-derived extracellular vesicles home in vivo to a lymphatic cell with about a 5-fold greater specificity than to another cell type, or to another organ, or to all other cell types combined. In embodiments, the megakaryocyte-derived extracellular vesicles home in vivo to a lymphatic cell with about a 6-fold greater specificity than to another cell type, or to another organ, or to all other cell types combined. In embodiments, the megakaryocyte-derived extracellular vesicles home in vivo to a lymphatic cell with about a 7-fold greater specificity than to another cell type, or to another organ, or to all other cell types combined. In embodiments, the megakaryocyte-derived extracellular vesicles home in vivo to a lymphatic cell with about a 8-fold greater specificity than to another cell type, or to another organ, or to all other cell types combined. In embodiments, the megakaryocyte-derived extracellular vesicles home in vivo to a lymphatic cell with about a 9-fold greater specificity than to another cell type, or to another organ, or to all other cell types combined. In embodiments, the megakaryocyte-derived extracellular vesicles home in vivo to a lymphatic cell with about a 10-fold greater specificity than to another cell type, or to another organ, or to all other cell types combined.

In embodiments, the megakaryocyte-derived extracellular vesicles are suitable for homing to a regulatory T cell in vivo. In embodiments, the megakaryocyte-derived extracellular vesicles are suitable for homing to a regulatory T cell in vitro. In embodiments, the megakaryocyte-derived extracellular vesicles home in vivo to a regulatory T cell with about a 2-fold greater specificity than to another cell type, or to another organ, or to all other cell types combined. In embodiments, the megakaryocyte-derived extracellular vesicles home in vivo to a regulatory T cell with about a 3-fold greater specificity than to another cell type, or to another organ, or to all other cell types combined. In embodiments, the megakaryocyte-derived extracellular vesicles home in vivo to a regulatory T cell with about a 4-fold greater specificity than to another cell type, or to another organ, or to all other cell types combined. In embodiments, the megakaryocyte-derived extracellular vesicles home in vivo to a regulatory T cell with about a 5-fold greater specificity than to another cell type, or to another organ, or to all other cell types combined. In embodiments, the megakaryocyte-derived extracellular vesicles home in vivo to a regulatory T cell with about a 6-fold greater specificity than to another cell type, or to another organ, or to all other cell types combined. In embodiments, the megakaryocyte-derived extracellular vesicles home in vivo to a regulatory T cell with about a 7-fold greater specificity than to another cell type, or to another organ, or to all other cell types combined. In embodiments, the megakaryocyte-derived extracellular vesicles home in vivo to a regulatory T cell with about a 8-fold greater specificity than to another cell type, or to another organ, or to all other cell types combined. In embodiments, the megakaryocyte-derived extracellular vesicles home in vivo to a regulatory T cell with about a 9-fold greater specificity than to another cell type, or to another organ, or to all other cell types combined. In embodiments, the megakaryocyte-derived extracellular vesicles home in vivo to a regulatory T cell with about a 10-fold greater specificity than to another cell type, or to another organ, or to all other cell types combined.

In one aspect, the disclosure provides methods of treating Fanconi Anemia (FA) that comprise methods for transferring a deliverable therapeutic agent.

In some embodiments, the present methods for transferring a deliverable therapeutic agent comprise: (a) obtaining an megakaryocyte-derived extracellular vesicle; (b) incubating the megakaryocyte-derived extracellular vesicle with a therapeutic agent to allow the therapeutic agent to populate the lumen of the megakaryocyte-derived extracellular vesicle and yield a deliverable therapeutic agent; and (c) administering the deliverable therapeutic agent to a patient or contacting the deliverable therapeutic agent with a biological cell in vitro and administering the contacted biological cell to a patient.

In some embodiments, the present methods for transferring a deliverable therapeutic agent comprise: (a) obtaining an megakaryocyte-derived extracellular vesicle; (b) incubating the megakaryocyte-derived extracellular vesicle with a therapeutic agent to allow the therapeutic agent to populate the lumen of the megakaryocyte-derived extracellular vesicle and yield a deliverable therapeutic agent; and (c) administering the deliverable therapeutic agent to a patient or contacting the deliverable therapeutic agent with a biological cell in vitro and administering the contacted biological cell to a patient.

In some embodiments, the present methods for transferring a deliverable therapeutic agent, comprise: (a) obtaining an megakaryocyte-derived extracellular vesicle; (b) incubating the megakaryocyte-derived extracellular vesicle with a therapeutic agent to allow the therapeutic agent to associate with the surface of the megakaryocyte-derived extracellular vesicle and yield a deliverable therapeutic agent; and (c) administering the deliverable therapeutic agent to a patient or contacting the deliverable therapeutic agent with a biological cell in vitro and administering the contacted biological cell to a patient.

In one aspect, the disclosure provides ex vivo methods for transferring a deliverable therapeutic agent. In some embodiments, the method comprises: (a) obtaining an megakaryocyte-derived extracellular vesicle; (b) incubating the megakaryocyte-derived extracellular vesicle with a therapeutic agent capable of treating Fanconi Anemia (FA) to allow the therapeutic agent to populate the lumen of the megakaryocyte-derived extracellular vesicle and yield a deliverable therapeutic agent; and (c) administering the deliverable therapeutic agent to a patient or contacting the deliverable therapeutic agent with a biological cell in vitro and administering the contacted biological cell to a patient.

In one aspect, the disclosure provides in vivo methods for transferring a deliverable therapeutic agent. In some embodiments, the method comprises: (a) obtaining an megakaryocyte-derived extracellular vesicle; (b) incubating the megakaryocyte-derived extracellular vesicle with a therapeutic agent capable of treating Fanconi Anemia (FA) to allow the therapeutic agent to associate with the surface of the megakaryocyte-derived extracellular vesicle and yield a deliverable therapeutic agent; (c) obtaining a biological cell from a patient; and (d) contacting the deliverable therapeutic agent with the biological cell in vitro and administering the contacted biological cell to the patient.

In some embodiments, the present methods for transferring a deliverable therapeutic agent comprise: (a) obtaining an megakaryocyte-derived extracellular vesicle; (b) incubating the megakaryocyte-derived extracellular vesicle with a therapeutic agent capable of treating Fanconi Anemia (FA) to allow the therapeutic agent to associate with the surface of the megakaryocyte-derived extracellular vesicle and yield a deliverable therapeutic agent; and (c) administering the deliverable therapeutic agent to a patient or contacting the deliverable therapeutic agent with a biological cell in vitro and administering the contacted biological cell to a patient.

In one aspect, the disclosure provides ex vivo methods for transferring a deliverable therapeutic agent useful for treating a myeloproliferative disease or disorder. In some embodiments, the method comprises: (a) obtaining an megakaryocyte-derived extracellular vesicle; (b) incubating the megakaryocyte-derived extracellular vesicle with a therapeutic agent capable of treating a myeloproliferative disease or disorder to allow the therapeutic agent to populate the lumen of the megakaryocyte-derived extracellular vesicle and yield a deliverable therapeutic agent; (c) obtaining a biological cell from a patient; and (d) contacting the deliverable therapeutic agent with the biological cell in vitro and administering the contacted biological cell to the patient.

In one aspect, the disclosure provides in vivo methods for transferring a deliverable therapeutic agent. In some embodiments, the method comprises: (a) obtaining an megakaryocyte-derived extracellular vesicle; (b) incubating the megakaryocyte-derived extracellular vesicle with a therapeutic agent capable of treating a myeloproliferative disease or disorder to allow the therapeutic agent to associate with the surface of the megakaryocyte-derived extracellular vesicle and yield a deliverable therapeutic agent; (c) obtaining a biological cell from a patient; and (d) contacting the deliverable therapeutic agent with the biological cell in vitro and administering the contacted biological cell to the patient.

In embodiments, the contacting of a deliverable therapeutic agent capable of treating Fanconi Anemia (FA) with the biological cell comprises co-culturing the deliverable therapeutic agent with the biological cell to provide a transfer of the cargo from the deliverable therapeutic agent to the biological cell.

In embodiments, the megakaryocyte-derived extracellular vesicles bind to a cell surface receptor on a cell of the patient. In embodiments, the megakaryocyte-derived extracellular vesicles bind to a cell surface receptor on the contacted biological cell of step (c). In embodiments, the biological cell is one or more of a cancer cell, a tumor cell, a cell infected by a virus, an epithelial cell, an endothelial cell, a nerve cell, a muscle cell, a connective tissue cell, a healthy cell, a diseased cell, a differentiated cell, and a pluripotent cell.

In embodiments, the megakaryocyte-derived extracellular vesicles fuse with the extracellular membrane of a cell of the patient. In embodiments, the megakaryocyte-derived extracellular vesicles fuse with the extracellular membrane of the biological cells of step (c). In embodiments, the biological cell is one or more of a cancer cell, a tumor cell, a cell infected by a virus, an epithelial cell, an endothelial cell, a nerve cell, a muscle cell, a connective tissue cell, a healthy cell, a diseased cell, a differentiated cell, and a pluripotent cell.

In embodiments, the megakaryocyte-derived extracellular vesicles are endocytosed by a cell of the patient. In embodiments, the megakaryocyte-derived extracellular vesicles are endocytosed by the biological cells of step (c). In embodiments, the biological cell is one or more of a cancer cell, a tumor cell, a cell infected by a virus, an epithelial cell, an endothelial cell, a nerve cell, a muscle cell, a connective tissue cell, a healthy cell, a diseased cell, a differentiated cell, and a pluripotent cell.

Methods of Producing Megakaryocyte-Derived Extracellular Vesicles

In embodiments, a cell culture process is adapted to produce allogeneic megakaryocyte-derived extracellular vesicles from primary human peripheral blood CD34+ HSCs. In embodiments, the megakaryocyte-derived extracellular vesicles are produced by a method comprising obtaining primary human peripheral blood CD34+ HSCs sourced from a commercial supplier and transitioning from a stem cell maintenance medium to an HSC expansion medium. In embodiments, the megakaryocyte-derived extracellular vesicles are produced by a method comprising obtaining primary human cord blood CD34+ HSCs. In embodiments, the megakaryocyte-derived extracellular vesicles are produced by a method comprising obtaining primary human bone marrow CD34+ HSCs. In embodiments, the method further involves placing HSC cultures in a megakaryocyte differentiation medium and collecting megakaryocyte-derived extracellular vesicles from culture supernatant. Accordingly, in embodiments, the present megakaryocyte-derived extracellular vesicles are produced from starting CD34+ HSCs.

In embodiments, the megakaryocyte differentiation is confirmed by biomarker expression and/or presence of one or more of CD41, CD61, CD42b, megakaryocyte-specific cytoskeletal proteins 131-tubulin, alpha granule components (e.g. platelet factor 4 and von Willebrand Factor), secretory granules, and ultrastructural characteristics (e.g. invaginated membrane system, dense tubular system, multivesicular bodies).

In embodiments, the megakaryocytes yield between about 10 to about 3000, about 50 to about 2600, about 80 to about 500, about 500 to about 2600, or about 500 to about 1500 megakaryocyte-derived extracellular vesicles/cell.

In embodiments, nanoparticle analysis, electron microscopy, flow cytometry, and/or western blots are used to confirm biomarker expression and/or presence and composition of megakaryocyte-derived extracellular vesicles.

In embodiments, the megakaryocyte-derived extracellular vesicles are isolated from megakaryocytes, which are generated in the absence of added erythropoietin. In embodiments, the megakaryocyte-derived extracellular vesicles are isolated from megakaryocytes which are generated in the presence of added thrombopoietin.

In embodiments, the megakaryocyte-derived extracellular vesicles are substantially free of nucleic acids. In embodiments, the megakaryocyte-derived extracellular vesicles are substantially free of autologous nucleic acids. In embodiments, the megakaryocyte-derived extracellular vesicles are substantially free of RNA. In embodiments, the megakaryocyte-derived extracellular vesicles comprise nucleic acids. In embodiments, the megakaryocyte-derived extracellular vesicles comprise autologous nucleic acids. In embodiments, the megakaryocyte-derived extracellular vesicles comprise autologous RNA. Non-limiting examples of RNA include rRNA, siRNA, microRNA, regulating RNA, and/or non-coding and coding RNA. In embodiments, the megakaryocyte-derived extracellular vesicles are substantially free of RNA from the cell from which the vesicles are derived. In non-limiting examples, the megakaryocyte-derived extracellular vesicles do not contain RNA due to the method of preparing the vesicles and/or due to the use of RNase to remove native RNAs.

In embodiments, the megakaryocyte-derived extracellular vesicles are substantially free of autologous DNA. In embodiments, the megakaryocyte-derived extracellular vesicles are substantially free of DNA from the cell from which the vesicles are derived. In non-limiting examples, the megakaryocyte-derived extracellular vesicles do not contain DNA due to the method of preparing the vesicles and/or due to the use of DNase to remove native DNAs. In embodiments, the megakaryocyte-derived extracellular vesicles are substantially free of one or more of: (a) megakaryocytes, (b) megakaryocyte-derived platelets, and (c) extracellular vesicles derived from platelets.

In embodiments, frozen granulocyte colony-stimulating factor (G-CSF) mobilized human peripheral blood CD34+ cells are obtained and cultured to megakaryocytes before subsequently enriching CD41+ cells (megakaryocytes) prior to culturing, and then measuring the CD41 expression and/or presence and concentration of megakaryocyte-derived extracellular vesicles in the cell culture by flow cytometer or nanoparticle analysis. In embodiments, the megakaryocyte-derived extracellular vesicles are generated by a series of centrifugations, e.g. at escalating speeds/force. In embodiments, the megakaryocyte-derived extracellular vesicles are generated by: (a) removing cells from culture medium at, e.g., about 150×g centrifugation for, e.g., about 10 min; (b) removing platelet-like particles (PLPs) and cell debris by centrifugation at, e.g., about 1000×g for, e.g., about 10 min; and (c) enriching the megakaryocyte-derived extracellular vesicles from the supernatant by ultracentrifugation at, e.g., about 25,000 rpm (38000×g) for, e.g., about 1 hour at, e.g., about 4° C.

In embodiments, a multi-phase culture process with differing pH and p02 or $pCO_2$ and different cytokine cocktails is used to greatly increase megakaryocyte production.

In embodiments, the megakaryocytes are generated by: (a) culturing CD34+ HSCs with a molecular signal/factor/cytokine cocktail that promotes megakaryocyte progenitor production; and (b) shifting cells to different conditions to expand mature megakaryocytes from progenitors. In embodiments, commercial media is used. In embodiments, serum-free media is used. In embodiments, pH is shifted to increase megakaryocyte production. In embodiments, percent $CO_2$ is shifted to increase megakaryocyte production. In embodiments, the identity of the molecular signals/factors/cytokines is altered to increase megakaryocyte production. In embodiments, the molecular signal/factor/cytokine cocktail contains one or more of TPO, GM-CSF, IL-3, IL-6, IL-11, SCF, FIt3L, IL-9, and the like.

In embodiments, the present production methods further involve the step of characterizing the resultant megakaryocyte-derived extracellular vesicles for one or more of CD54, CD18, CD43, CD11b, CD62P, CD41, CD61, CD21, CD51, CLEC-2, LAMP-1 (CD107a), CD63, CD42b, CD9, CD31, CD47, CD147, CD32a, and GPVI. e.g., without limitation by nanoparticle analysis, electron microscopy, flow cytometry, and/or western blot analysis. In embodiments, the present production methods further involve the step of characterizing the resultant megakaryocyte-derived extracellular vesicles for phosphatidylserine, e.g., without limitation by testing for Annexin V, e.g., without limitation by nanoparticle analysis, electron microscopy, flow cytometry, and/or western blot analysis.

In embodiments, the megakaryocyte-derived extracellular vesicles are generated from mature megakaryocytes. In embodiments, the megakaryocyte-derived extracellular vesicles are generated from immature megakaryocytes.

In embodiments, methods to generate megakaryocyte-derived extracellular vesicles are standardized to enable large-scale production.

In embodiments, the present methods to generate megakaryocyte-derived extracellular vesicles inter-batch/donor variability is of less than about 20%, or less than about 15%, or less than about 10%, or less than about 5%. In embodiments, methods to generate megakaryocyte-derived extracellular vesicles are developed such that inter-batch/donor variability is less than 12.5%. In embodiments, methods to generate megakaryocyte-derived extracellular vesicles are developed such that inter-batch/donor variability is less than 10%. In embodiments, methods to generate megakaryocyte-derived extracellular vesicles are developed such that inter-batch/donor variability is less than 7.5%. In embodiments, methods to generate megakaryocyte-derived extracellular vesicles are developed such that inter-batch/donor variability is less than 5%. In embodiments, methods to generate megakaryocyte-derived extracellular vesicles are developed such that inter-batch/donor variability is less than 2.5%.

In embodiments, the population comprises about 1×$10^7$ or more, about 1.5×$10^7$ or more, about 5×$10^7$ or more, 1×$10^8$ or more, about 1.5×$10^8$ or more, about 5×$10^8$ or more, about 1×$10^9$ or more, about 5×$10^9$ or more, about 1×$10^{10}$ or more, or about 1×$10^{10}$ or more megakaryocyte-derived extracellular vesicles.

In embodiments, the population comprises between about 2×$10^{10}$ to about 1×$10^{11}$, about 4×$10^{10}$ to about 9×$10^{11}$, or about 5×$10^{10}$ to about 8.5×$10^{11}$ megakaryocyte-derived extracellular vesicles.

In embodiments, the megakaryocyte-derived extracellular vesicles are isolated as a population. In embodiments, the population of megakaryocyte-derived extracellular vesicles is substantially homogenous.

In embodiments, substantially all of the megakaryocyte-derived extracellular vesicles in the population comprise CD54. In embodiments, about 0% to about 5%, about 0% to about 10%, about 15% to about 90%, about 30% to about 80%, or about 50% to about 70% of the megakaryocyte-derived extracellular vesicles in the population comprise CD54. In embodiments, greater than about 20%, greater than about 30%, greater than about 40%, greater than about 50%, greater than about 60%, greater than about 70%, greater than about 80%, greater than about 90%, or greater than about 95%, or greater than about 99% of the megakaryocyte-derived extracellular vesicles in the population comprise CD54. In embodiments, less than about 30%, less than about 25%, less than about 20%, less than about 15%, less than about 10%, less than about 5%, or less than about 1% of the megakaryocyte-derived extracellular vesicles in the population comprise CD54. In embodiments, all of the megakaryocyte-derived extracellular vesicles in the population are free of, or substantially free of CD54.

In embodiments, substantially all of the megakaryocyte-derived extracellular vesicles in the population comprise CD18. In embodiments, about 0% to about 5%, about 0% to about 10%, about 15% to about 90%, about 30% to about 80%, or about 50% to about 70% of the megakaryocyte-derived extracellular vesicles in the population comprise CD18. In embodiments, greater than about 20%, greater than about 30%, greater than about 40%, greater than about 50%, greater than about 60%, greater than about 70%, greater than about 80%, greater than about 90%, or greater than about 95%, or greater than about 99% of the megakaryocyte-derived extracellular vesicles in the population comprise CD18. In embodiments, less than about 30%, less than about 25%, less than about 20%, less than about 15%, less than about 10%, less than about 5%, or less than about 1% of the megakaryocyte-derived extracellular vesicles in the population comprise CD18. In embodiments, all of the megakaryocyte-derived extracellular vesicles in the population are free of, or substantially free of CD18.

In embodiments, substantially all of the megakaryocyte-derived extracellular vesicles in the population comprise CD43. In embodiments, about 1% to about 30%, about 1% to about 25%, about 1% to about 20%, or about 1% to about 15%, about 0% to about 5% or about 0% to about 10% of the megakaryocyte-derived extracellular vesicles in the population comprise CD43. In embodiments, less than about 30%, less than about 25%, less than about 20%, less than about 15%, less than about 10%, less than about 5%, or less than about 1% of the megakaryocyte-derived extracellular vesicles in the population comprise CD43. In embodiments, all of the megakaryocyte-derived extracellular vesicles in the population are free of, or substantially free of CD43.

In embodiments, substantially all of the megakaryocyte-derived extracellular vesicles in the population comprise CD11b. In embodiments, about 0% to about 5%, about 0% to about 10%, about 1% to about 50%, about 5% to about 40%, or about 10% to about 35% of the megakaryocyte-derived extracellular vesicles in the population comprise CD11b. In embodiments, less than about 50%, less than about 45%, less than about 40%, less than about 35%, less than about 30%, less than about 25%, less than about 20%, less than about 15%, less than about 10%, or less than about 5% of the megakaryocyte-derived extracellular vesicles in the population comprise CD11 b. In embodiments, all of the megakaryocyte-derived extracellular vesicles in the population are free of, or substantially free of CD11b.

In embodiments, substantially all of the megakaryocyte-derived extracellular vesicles in the population comprise CD62P. In embodiments, about 0% to about 40%, about 0% to about 30%, about 0% to about 20%, about 0% to about 10%, or about 0% to about 5%, of the megakaryocyte-derived extracellular vesicles in the population comprise CD62P. In embodiments, less than about 40%, less than about 30%, less than about 20%, less than about 10% of the megakaryocyte-derived extracellular vesicles in the population comprise CD62P. In embodiments, all of the megakaryocyte-derived extracellular vesicles in the population are free of, or substantially free of CD62P.

In embodiments, substantially all of the megakaryocyte-derived extracellular vesicles in the population comprise CD41. In embodiments, about 15% to about 90%, about 30% to about 80%, or about 50% to about 70% of the megakaryocyte-derived extracellular vesicles in the population comprise CD41. In embodiments, greater than about 20%, greater than about 30%, greater than about 40%, greater than about 50%, greater than about 60%, greater than about 70%, greater than about 80%, greater than about 90%, or greater than about 95%, or greater than about 99% of the megakaryocyte-derived extracellular vesicles in the population comprise CD41.

In embodiments, substantially all of the megakaryocyte-derived extracellular vesicles in the population comprise CD61. In embodiments, about 40% to about 100%, about 60% to about 100%, or about 85% to about 10% of the megakaryocyte-derived extracellular vesicles in the population comprise CD61. In embodiments, greater than about 40%, greater than about 50%, greater than about 60%, greater than about 70%, greater than about 80%, greater than about 85%, greater than about 90%, or greater than about 95%, or greater than about 99% of the megakaryocyte-derived extracellular vesicles in the population comprise CD61.

In embodiments, substantially all of the megakaryocyte-derived extracellular vesicles in the population comprise CD21. In embodiments, about 0% to about 10%, about 0% to about 5%, about 15% to about 90%, about 30% to about 80%, or about 50% to about 70% of the megakaryocyte-derived extracellular vesicles in the population comprise CD21. In embodiments, greater than about 20%, greater than about 30%, greater than about 40%, greater than about 50%, greater than about 60%, greater than about 70%, greater than about 80%, greater than about 90%, or greater than about 95%, or greater than about 99% of the megakaryocyte-derived extracellular vesicles in the population comprise CD21. In embodiments, less than about 50%, less than about 45%, less than about 40%, less than about 35%, less than about 30%, less than about 25%, less than about 20%, less than about 15%, less than about 10%, or less than about 5% of the megakaryocyte-derived extracellular vesicles in the population comprise CD21. In embodiments, all of the megakaryocyte-derived extracellular vesicles in the population are free of, or substantially free of CD21.

In embodiments, substantially all of the megakaryocyte-derived extracellular vesicles in the population comprise CD51. In embodiments, about 0% to about 10%, about 0% to about 5%, about 15% to about 90%, about 30% to about 80%, or about 50% to about 70% of the megakaryocyte-derived extracellular vesicles in the population comprise CD51. In embodiments, greater than about 20%, greater than about 30%, greater than about 40%, greater than about 50%, greater than about 60%, greater than about 70%, greater than about 80%, greater than about 90%, or greater than about 95%, or greater than about 99% of the megakaryocyte-derived extracellular vesicles in the population comprise CD51. In embodiments, less than about 50%, less than about 45%, less than about 40%, less than about 35%, less than about 30%, less than about 25%, less than about 20%, less than about 15%, less than about 10%, or less than about 5% of the megakaryocyte-derived extracellular vesicles in the population comprise CD51. In embodiments, all of the megakaryocyte-derived extracellular vesicles in the population are free of, or substantially free of CD51.

In embodiments, substantially all of the megakaryocyte-derived extracellular vesicles in the population comprise CLEC-2. In embodiments, about 0% to about 10%, about 0% to about 5%, or about 0% to about 12% of the megakaryocyte-derived extracellular vesicles in the population comprise CLEC-2. In embodiments, less than about 10%, less than about 5%, or less than about 2% of the megakaryocyte-derived extracellular vesicles in the population comprise CLEC-2. In embodiments, all of the megakaryocyte-derived extracellular vesicles in the population are free of, or substantially free of CLEC-2.

In embodiments, substantially all of the megakaryocyte-derived extracellular vesicles in the population comprise LAMP-1 (CD107a). In embodiments, about 0% to about 20%, about 1% to about 15%, about 2% to about 10%, about 0% to about 5%, or about 0% to about 5% of the megakaryocyte-derived extracellular vesicles in the population comprise LAMP-1 (CD107a). In embodiments, less than about 20%, less than about 15%, less than about 10%, or less than about 5% of the megakaryocyte-derived extracellular vesicles in the population comprise LAMP-1 (CD107a). In embodiments, all of the megakaryocyte-derived extracellular vesicles in the population are free of, or substantially free of LAMP-1 (CD107a).

In embodiments, less than about 20%, less than about 15%, less than about 10%, or less than about 5% of a population of CD41+ megakaryocyte-derived extracellular vesicles comprise LAMP-1 (CD107a).

In embodiments, the megakaryocyte-derived extracellular vesicles in the population are substantially free of DRAQ5. In embodiments, about 0% to about 20%, about 0% to about 15%, about 0% to about 10%, or about 0% to about 5% of the megakaryocyte-derived extracellular vesicles in the population comprise DRAQ5. In embodiments, less than about 20%, less than about 15%, less than about 10%, or less than about 5% of the megakaryocyte-derived extracellular vesicles in the population comprise DRAQ5.

In embodiments, substantially all of the megakaryocyte-derived extracellular vesicles in the population comprise CD63. In embodiments, about 1% to about 20%, about 1% to about 15%, or about 1% to about 10% of the megakaryocyte-derived extracellular vesicles in the population comprise CD63. In embodiments, less than about 20%, less than about 15%, less than about 10%, less than about 5%, or less than about 1% of the megakaryocyte-derived extracellular vesicles in the population comprise CD63. In embodiments, all of the megakaryocyte-derived extracellular vesicles in the population are free of, or substantially free of CD63.

In embodiments, substantially all of the megakaryocyte-derived extracellular vesicles in the population comprise CD42b. In embodiments, about 0% to about 20%, about 0% to about 15%, about 0% to about 10%, or about 0% to about 5% of the megakaryocyte-derived extracellular vesicles in the population comprise CD42b. In embodiments, less than about 20%, less than about 15%, less than about 10%, less than about 5%, or less than about 1% of the megakaryocyte-derived extracellular vesicles in the population comprise CD42b. In embodiments, all of the megakaryocyte-derived extracellular vesicles in the population are free of, or substantially free of CD42b.

In embodiments, substantially all of the megakaryocyte-derived extracellular vesicles in the population comprise CD9. In embodiments, about 40% to about 100%, about 50% to about 80%, or about 60% to about 70% of the megakaryocyte-derived extracellular vesicles in the population comprise CD9. In embodiments, greater than about 30%, greater than about 40%, greater than about 50%, greater than about 60%, greater than about 70%, greater than about 80%, greater than about 90%, or greater than about 95%, or greater than about 99% of the megakaryocyte-derived extracellular vesicles in the population comprise CD9.

In embodiments, substantially all of the megakaryocyte-derived extracellular vesicles in the population comprise CD31. In embodiments, about 1% to about 30%, about 1% to about 25%, about 1% to about 20%, or about 1% to about 15% of the megakaryocyte-derived extracellular vesicles in the population comprise CD31. In embodiments, less than about 30%, less than about 25%, less than about 20%, less than about 15%, less than about 10%, less than about 5%, or less than about 1% of the megakaryocyte-derived extracellular vesicles in the population comprise CD31. In embodiments, all of the megakaryocyte-derived extracellular vesicles in the population are free of, or substantially free of CD31.

In embodiments, substantially all of the megakaryocyte-derived extracellular vesicles in the population comprise CD47. In embodiments, about 1% to about 40%, about 1% to about 35%, about 1% to about 20%, about 20% to about 30%, about 30% to about 40%, or about 1% to about 15% of the megakaryocyte-derived extracellular vesicles in the population comprise CD47. In embodiments, less than about 40%, less than about 30%, less than about 25%, less than about 20%, less than about 15%, less than about 10%, less than about 5%, or less than about 1% of the megakaryocyte-derived extracellular vesicles in the population comprise CD47. In embodiments, all of the megakaryocyte-derived extracellular vesicles in the population are free of, or substantially free of CD47.

In embodiments, substantially all of the megakaryocyte-derived extracellular vesicles in the population comprise CD147. In embodiments, about 1% to about 30%, about 1% to about 25%, about 1% to about 20%, about 20% to about 30%, or about 1% to about 15% of the megakaryocyte-derived extracellular vesicles in the population comprise CD147. In embodiments, less than about 30%, less than about 25%, less than about 20%, less than about 15%, less than about 10%, less than about 5%, or less than about 1% of the megakaryocyte-derived extracellular vesicles in the population comprise CD147. In embodiments, all of the megakaryocyte-derived extracellular vesicles in the population are free of, or substantially free of CD147.

In embodiments, substantially all of the megakaryocyte-derived extracellular vesicles in the population comprise CD32a. In embodiments, about 0% to about 20%, about 1% to about 15%, or about 1% to about 10% of the megakaryocyte-derived extracellular vesicles in the population comprise CD32a. In embodiments, less than about 20%, less than about 15%, less than about 10%, less than about 5%, or less than about 1% of the megakaryocyte-derived extracellular vesicles in the population comprise CD32a. In embodiments, all of the megakaryocyte-derived extracellular vesicles in the population are free of, or substantially free of CD32a.

In embodiments, substantially all of the megakaryocyte-derived extracellular vesicles in the population comprise GVPI. In embodiments, about 0% to about 5%, about 0% to about 10%, about 0% to about 30%, about 0% to about 15%, or about 0% to about 10% of the megakaryocyte-derived extracellular vesicles in the population comprise GVPI. In embodiments, less than about 30%, less than about 25%, less than about 20%, less than about 15%, less than about 10%, less than about 5%, or less than about 1% of the megakaryocyte-derived extracellular vesicles in the population comprise GVPI. In embodiments, all of the megakaryocyte-derived extracellular vesicles in the population are free of, or substantially free of GVPI.

In embodiments, substantially all of the megakaryocyte-derived extracellular vesicles in the population comprise phosphatidylserine. In embodiments, about 15% to about 90%, about 30% to about 80%, or about 50% to about 70% of the megakaryocyte-derived extracellular vesicles in the population comprise phosphatidylserine. In embodiments, greater than about 20%, greater than about 30%, greater than about 40%, greater than about 50%, greater than about 60%, greater than about 70%, greater than about 80%, greater than about 90%, or greater than about 95%, or greater than about 99% of the megakaryocyte-derived extracellular vesicles in the population comprise phosphatidylserine. In embodiments, less than about 30%, less than about 25%, less than about 20%, less than about 15%, less than about 10%, less than about 5%, or less than about 1% of the megakaryocyte-derived extracellular vesicles in the population comprise GVPI. In embodiments, all of the megakaryocyte-derived extracellular vesicles in the population are free of, or substantially free of phosphatidylserine.

In embodiments, the megakaryocyte-derived extracellular vesicles are generated by: (a) obtaining a human pluripotent stem cell being a primary CD34+ HSC sourced from peripheral blood or cord blood; (b) differentiating the human pluripotent stem cell to a megakaryocyte in the absence of added EPO and in the presence of added TPO; and (c) isolating the megakaryocyte-derived extracellular vesicles from the megakaryocytes.

In embodiments, the method is an in vivo method. In embodiments, the method is an ex vivo method.

In embodiments, the CD34+ HSC sourced from peripheral blood are multipotent stem cells derived from volunteers whose stem cells are mobilized into the bloodstream by administration of a mobilization agent such as granulocyte colony stimulating factor (G-CSF) and granulocyte-macrophage colony stimulating factor (GM-CSF).

In embodiments, the cord blood comprises multipotent stem cells derived from blood that remains in the placenta and the attached umbilical cord after childbirth.

In embodiments, the megakaryocyte-derived extracellular vesicles are autologous with the patient. In embodiments, human pluripotent stem cells are extracted from the patient and used to generate megakaryocytes, from which megakaryocyte-derived extracellular vesicles comprising a cargo of choice are generated and then administered to the patient. In embodiments, differentiated cells are extracted from the patient and used to generate iPSCs, which in turn are used to generate megakaryocytes, from which megakaryocyte-derived extracellular vesicles comprising a cargo of choice are generated and then administered to the patient.

In embodiments, the megakaryocyte-derived extracellular vesicles are allogeneic with the patient. In embodiments, human pluripotent stem cells are extracted from a human subject who is not the patient and used to generate megakaryocytes, from which megakaryocyte-derived extracellular vesicles comprising a cargo of choice are generated and then administered to the patient. In embodiments, differentiated cells are extracted from a human subject who is not the patient and used to generate iPSCs, which in turn are used to generate megakaryocytes, from which megakaryocyte-derived extracellular vesicles comprising a cargo of choice are generated and then administered to the patient.

In embodiments, the megakaryocyte-derived extracellular vesicles are heterologous with the patient. In embodiments, pluripotent stem cells are extracted from a non-human subject and used to generate megakaryocytes, from which megakaryocyte-derived extracellular vesicles comprising a cargo of choice are generated and then administered to the patient. In embodiments, differentiated cells are extracted from a non-human subject and used to generate iPSCs, which in turn are used to generate megakaryocytes, from which megakaryocyte-derived extracellular vesicles comprising a cargo of choice are generated and then administered to the patient.

In embodiments, the incubating comprises one or more of sonication, saponin permeabilization, mechanical vibration, hypotonic dialysis, extrusion through porous membranes, cholesterol conjugation, application of electric current and combinations thereof. In embodiments, the incubating comprises one or more of electroporating, transforming, transfecting, and microinjecting.

In embodiments, the method further comprises (d) contacting the megakaryocyte-derived extracellular vesicles with radiation. In embodiments, the radiation is gamma radiation. In embodiments, the gamma radiation is at an amount greater than 12 kGy, 25 kGy, or 50 kGy. In embodiments, the gamma radiation is at an amount between about 12 kGy and 15 kGy. In embodiments, the gamma radiation is at an amount between about 15 kGy and 20 kGy. In embodiments, the gamma radiation is at an amount between about 20 kGy and 25 kGy. In embodiments, the gamma radiation is at an amount between about 25 kGy and 30 kGy. In embodiments, the gamma radiation is at an amount between about 30 kGy and 35 kGy. In embodiments, the gamma radiation is at an amount between about 35 kGy and 40 kGy. In embodiments, the gamma radiation is at an amount between about 40 kGy and 45 kGy. In embodiments, the gamma radiation is at an amount between about 45 kGy and 50 kGy. In embodiments, the gamma radiation is at an amount between about 50 kGy and 55 kGy. In embodiments, the gamma radiation is at an amount between about 55 kGy and 60 kGy.

In embodiments, the method is substantially serum free. In embodiments, the method is greater than 60% serum free. In embodiments, the method is greater than 70% serum free. In embodiments, the method is greater than 80% serum free. In embodiments, the method is greater than 90% serum free.

In various embodiments, the megakaryocyte-derived extracellular vesicles of the disclosure are substantially purified megakaryocyte-derived extracellular vesicles. In embodiments, substantially purified is synonymous with biologically pure. In embodiments, the substantially purified megakaryocyte-derived extracellular vesicles are largely free to varying degrees from components which normally accompany it as found in its native state. “Isolate” denotes a degree of separation from original source or surroundings. In embodiments, the substantially purified megakaryocyte-derived extracellular vesicles are sufficiently free of other materials such that any impurities do not materially affect the biological properties of the megakaryocyte-derived extracellular vesicles or cause other adverse consequences. In embodiments, the substantially purified megakaryocyte-derived extracellular vesicles are sufficiently free of cellular material, viral material, or culture medium that may be needed for production. Purity and homogeneity are typically determined using biochemical techniques known in the art. In embodiments, the megakaryocyte-derived extracellular vesicles are purified using size exclusion filtration. In embodiments, the filter has a pore size of about 650 nm. In embodiments, the megakaryocyte-derived extracellular vesicles are purified using size exclusion filtration. In embodiments, the filter has a pore size ranging from about 50 nm to about 600 nm. In embodiments, the filter has a pore size of at least 50 nm. In embodiments, the filter has a pore size of about 600 nm.

Cargo of Megakaryocyte-Derived Extracellular Vesicles

Megakaryocyte-derived extracellular vesicles may contain diverse cargo such as mRNAs, microRNAs, and cytokines. Megakaryocyte-derived extracellular vesicles are able to transfer their cargo to alter the function of target cells. They exert their influence on the target cells through surface receptor signaling, plasma membrane fusion, and internalization. By loading megakaryocytes or megakaryocyte-derived extracellular vesicles with biologic or therapeutic cargo, megakaryocyte-derived extracellular vesicles can be further used as delivery vehicles to achieve a targeted therapeutic effect. Until now, small RNAs (siRNA and miRNA), small linear DNA, and plasmid DNA have all been successfully loaded into megakaryocyte-derived extracellular vesicles for a variety of delivery applications. Megakaryocyte-derived extracellular vesicles targeting is defined by their complement of surface proteins and can be further engineered to express or remove specific biomarkers of interest to refine biodistribution and cell-cell recognition. For instance, the present megakaryocyte-derived extracellular vesicles, with their unique biomarker profiles, are particularly suited for delivery of payloads, e.g. therapies.

In embodiments, the megakaryocyte-derived extracellular vesicles are suitable for loading with cargo into the lumen. In embodiments, the cargo is selected from one or more of a RNA, DNA, protein, carbohydrate, lipid, biomolecule, and small molecule. In embodiments, the cargo is a biologically produced component. In embodiments, the cargo is a synthetically produced component. In embodiments, the cargo is pre-loaded into megakaryocyte-derived extracellular vesicles. In embodiments, a biological component is overexpressed in megakaryocytes so that generated megakaryocyte-derived extracellular vesicles comprise the biological component. In embodiments, the cargo is post-loaded into megakaryocyte-derived extracellular vesicles. In embodiments, purified megakaryocyte-derived extracellular vesicles are mixed with cargo to generate cargo-loaded megakaryocyte-derived extracellular vesicles. In embodiments, the cargo is hydrophobic. In embodiments, the cargo is hydrophilic. In embodiments, the cargo is integrated into the lipid bilayer of the megakaryocyte-derived extracellular vesicles. In embodiments, the cargo is located in the lumen of the megakaryocyte-derived extracellular vesicles.

In embodiments, in addition to or as an alternative to the cargo located in the lumen of the megakaryocyte-derived extracellular vesicles, the cargo is associated with the megakaryocyte-derived extracellular vesicles. In embodiments, the cargo is associated with the surface and/or the exterior of the megakaryocyte-derived extracellular vesicles. Non-limiting examples of cargo associated with the megakaryocyte-derived extracellular vesicles includes cargo that is covalently conjugated to the surface of the vesicle or cargo that is associated with the surface via electrostatic interactions. As would be understood by one of ordinary skill in the art, cargo associated with the megakaryocyte-derived extracellular vesicles can still be transported even when not loaded into the lumen of the vesicle.

In embodiments, the cargo is loaded into the megakaryocyte-derived extracellular vesicle using an active loading strategy, which is physically-induced and/or chemically-induced. In embodiments, the active loading strategy is physically-induced. In embodiments, the physically-induced active loading strategy comprises the mechanical or physical disruption of the megakaryocyte-derived extracellular vesicle lipid bilayer through external forces, such as electroporation, sonication, freeze-thaw cycling, and extrusion. In embodiments, the electroporation involves the use of an electric field to induce spontaneous pore formation in the megakaryocyte-derived extracellular vesicle lipid bilayer, wherein the presence of the electric field disrupts the lipid bilayer, while removal of the field enables closure of pores and reformation of the lipid layer after the cargo has been taken up by the megakaryocyte-derived extracellular vesicle. In embodiments, the sonication involves ultrasound energy applied through a sonicator probe that decreases the rigidity of the megakaryocyte-derived extracellular vesicle lipid bilayer, enabling cargo diffusion. In embodiments, the freeze-thaw cycling uses thermal energy to facilitate megakaryocyte-derived extracellular vesicle cargo loading. In embodiments, extrusion is performed following established protocols for formation of synthetic liposomes, wherein megakaryocyte-derived extracellular vesicles are mixed with free cargo and passed through membranes containing nanoscale pores, wherein the sheer force disrupts the lipid bilayer, allowing exogenous cargo to enter megakaryocyte-derived extracellular vesicles.

In embodiments, the active loading strategy is chemically-induced. In embodiments, the chemically-induced active loading strategy comprises the use of chemical agents, such as saponin or transfection reagents, to bypass the megakaryocyte-derived extracellular vesicle lipid bilayer. In embodiments, the chemical agent is a detergent, such as saponin. In embodiments, the saponin is used to selectively remove cholesterol from the megakaryocyte-derived extracellular vesicle lipid bilayer, opening pores in the lipid bilayer. In embodiments, the chemical agent is a transfection agent. In embodiments, the transfection agent is used to deliver nucleic acids into the megakaryocyte-derived extracellular vesicle by exploiting cationic substances that promote interactions with the lipid bilayer and subsequent internalization. In embodiments, the transfection agent is lipofectamine and/or a lipid-based agent.

In embodiments, the loading ratio of a nucleic acid (i.e. copies of nucleic acid per vesicle) into megakaryocyte-derived extracellular vesicles of the disclosure ranges from about 1 to about 1000, about 1 to about 500, about 1 to about 100, about 10 to about 1000, about 100 to about 1000, about 500 to about 1000, about 100 to about 500,000, about 1000 to about 300,000, about 100,000 to about 300,000, about 1000, to about 10,000, or about 1000 to about 5000. In embodiments, the nucleic acid is DNA. In embodiments, the nucleic acid is plasmid DNA.

In embodiments, the loading efficiency for loading cargo, such as a nucleic acid, into megakaryocyte-derived extracellular vesicles of the disclosure ranges from about 1% to about 99%, about 10% to about 90%, about 30% to about 70%, about 40% to about 60%, about 40% to about 50%, or about 50% to about 60%. In embodiments, the cargo is a nucleic acid. In embodiments, the nucleic acid is DNA. In embodiments, the nucleic acid is plasmid DNA. In embodiments, loading efficiency is calculated using the following equation:

$$\text{Loading efficiency (\%)} = \text{cargo} + MV\#/\text{Total } MV\#$$

In embodiments, the surface of megakaryocyte-derived extracellular vesicles is modified to impact biodistribution and targeting capabilities of megakaryocyte-derived extracellular vesicles. In embodiments, surface ligands are added to megakaryocyte-derived extracellular vesicles through genetic engineering. In embodiments, the megakaryocyte-derived extracellular vesicles are generated that express fusion proteins in their lipid bilayers. In embodiments, the endogenous proteins in megakaryocyte-derived extracellular vesicle lipid bilayers are fused with targeting ligands through cell engineering.

In embodiments, the cargo is one or more therapeutic agents. In embodiments, the therapeutic agent is a nucleic acid therapeutic agent. In embodiments, the nucleic acid therapeutic agent encodes a functional protein.

In embodiments, the nucleic acid therapeutic agent is selected from one or more non-autologous and/or recombinant nucleic acid constructs selected from mRNA, tRNA, rRNA, siRNA, microRNA, regulating RNA, non-coding and coding RNA, linear DNA, DNA fragments, or DNA plasmids. In embodiments, the nucleic acid therapeutic agent is selected from one or more of mRNA, miRNA, siRNA, and snoRNA.

In embodiments, the one or more non-autologous and/or recombinant nucleic acid constructs are incorporated into a vector. In embodiments, the vector is an expression vector comprising an expression control sequence operatively linked to a nucleotide sequence. In embodiments, the vector is a plasmid, a phagemid, a phage derivative, a cosmid, or a viral vector. In embodiments, the viral vector comprises an adenovirus vector, an adeno-associated virus vector, a poxvirus vector, a retrovirus vector, a lentivirus vector, a sendai virus vector, herpes simplex virus vector, a cytomegalovirus vector, or chimeric viral vectors.

In embodiments, the therapeutic agent comprises a FA-related gene or a fragment thereof comprising FANCA, FANCB, FANCC, FANCD1 (BRCA2), FANCD2, FANCE, FANCF, FANCG, FANCI, FANCJ (BRIP1), FANCL, FANCM, FANCN (PALB2), FANCO (RAD51C), FANCP (SLX4), FANCQ (ERCC4), FANCR (Rad51), FANGS (BRCA1), FANCT (UBE2T), FANCU (XRCC2), FANCV (REV7) and FANCW (RFWD3) or a fragment thereof.

In embodiments, the therapeutic agent increases or restores the FA-related gene expression and/or levels and/or function of one or more FA-related proteins.

In embodiments, the FA-related proteins comprise FANCA, FANCB, FANCC, FANCD1 (BRCA2), FANCD2, FANCE, FANCF, FANCG, FANCI, FANCJ (BRIP1), FANCL, FANCM, FANCN (PALB2), FANCO (RAD51C), FANCP (SLX4), FANCQ (ERCC4), FANCR (Rad51), FANGS (BRCA1), FANCT (UBE2T), FANCU (XRCC2), FANCV (REV7) and FANCW (RFWD3).

In embodiments, the therapeutic agent is a small molecule therapeutic agent, or a biologic therapeutic agent. In embodiments, the biologic therapeutic agent is used for gene therapy. In embodiments, the biologic therapeutic agent encodes a functional protein or a recombinant protein. In embodiments, the functional protein or the recombinant protein comprises a wild-type protein, a fusion protein, a cytokine, an antigen, and a peptide, an antibody or an antibody fragment. In embodiments, the therapeutic agent is a nucleic acid therapeutic agent. In embodiments, the nucleic acid therapeutic agent expresses a wild-type functional FA gene, and/or comprises a nucleic acid encoding a functional FA-related gene, or a protein product thereof, or a nucleic acid encoding a gene-editing protein capable of creating a functional FA-related gene, or a protein product thereof, or a ribonucleoprotein gene-editing complex capable of creating a functional FA-related gene or a protein product thereof.

In embodiments, the therapeutic agent is any nucleic acid delivery system known in the art useful for vaccination. In one embodiment, the nucleic acid delivery system is a vaccine vector, a DNA plasmid, or an mRNA vaccine. In embodiments, the therapeutic agent is a vaccine and/or an immunogenic antigen. In embodiments, the nucleic acid therapeutic agent encodes a wild type gene (i.e., FA-related gene), which is defective in the patient. In embodiments, the nucleic acid therapeutic agent is mRNA, and optionally: is in vitro transcribed or synthetic and/or comprises one or more non-canonical nucleotides, optionally selected from pseudouridine and 5-methoxyuridine.

In embodiments, the one or more non-canonical nucleotides are selected from 2-thiouridine, 5-azauridine, pseudouridine, 4-thiouridine, 5-methyluridine, 5-methylpseudouridine, 5-aminouridine, 5-aminopseudouridine, 5-hydroxyuridine, 5-hydroxypseudouridine, 5-methoxyuridine, 5-methoxypseudouridine, 5-ethoxyuridine, 5-ethoxypseudouridine, 5-hydroxymethyluridine, 5-hydroxymethylpseudouridine, 5-carboxyuridine, 5-carboxypseudouridine, 5-formyluridine, 5-formylpseudouridine, 5-methyl-5-azauridine, 5-amino-5-azauridine, 5-hydroxy-5-azauridine, 5-methylpseudouridine, 5-aminopseudouridine, 5-hydroxypseudouridine, 4-thio-5-azauridine, 4-thiopseudouridine, 4-thio-5-methyluridine, 4-thio-5-aminouridine, 4-thio-5-hydroxyuridine, 4-thio-5-methyl-5-azauridine, 4-thio-5-amino-5-azauridine, 4-thio-5-hydroxy-5-azauridine, 4-thio-5-methylpseudouridine, 4-thio-5-aminopseudouridine, 4-thio-5-hydroxypseudouridine, 2-thiocytidine, 5-azacytidine, pseudoisocytidine, N4-methylcytidine, N4-aminocytidine, N4-hydroxycytidine, 5-methylcytidine, 5-aminocytidine, 5-hydroxycytidine, 5-methoxycytidine, 5-ethoxycytidine, 5-hydroxymethylcytidine, 5-carboxycytidine, 5-formylcytydine, 5-methyl-5-azacytidine, 5-amino-5-azacytidine, 5-hydroxy-5-azacytidine, 5-methylpseudoisocytidine, 5-aminopseudoisocytidine, 5-hydroxypseudoisocytidine, N4-methyl-5-azacytidine, N4-methylpseudoisocytidine, 2-thio-5-azacytidine, 2-thiopseudoisocytidine, 2-thio-N4-methylcytidine, 2-thio-N4-aminocytidine, 2-thio-N4-hydroxycytidine, 2-thio-5-methylcytidine, 2-thio-5-aminocytidine, 2-thio-5-hydroxycytidine, 2-thio-5-methyl-5-azacytidine, 2-thio-5-amino-5-azacytidine, 2-thio-5-hydroxy-5-azacytidine, 2-thio-5-methylpseudoisocytidine, 2-thio-5-aminopseudoisocytidine, 2-thio-5-hydroxypseudoisocytidine, 2-thio-N4-methyl-5-azacytidine, 2-thio-N4-methylpseudoisocytidine, N4-methyl-5-methylcytidine, N4-methyl-5-aminocytidine, N4-methyl-5-hydroxycytidine, N4-methyl-5-methyl-5-azacytidine, N4-methyl-5-amino-5-azacytidine, N4-methyl-5-hydroxy-5-azacytidine, N4-methyl-5-methylpseudoisocytidine, N4-methyl-5-aminopseudoisocytidine, N4-methyl-5-hydroxypseudoisocytidine, N4-amino-5-azacytidine, N4-aminopseudoisocytidine, N4-amino-5-methylcytidine, N4-amino-5-aminocytidine, N4-amino-5-hydroxycytidine, N4-amino-5-methyl-5-azacytidine, N4-amino-5-amino-5-azacytidine, N4-amino-5-hydroxy-5-azacytidine, N4-amino-5-methylpseudoisocytidine, N4-amino-5-aminopseudoisocytidine, N4-amino-5-hydroxypseudoisocytidine, N4-hydroxy-5-azacytidine, N4-hydroxypseudoisocytidine, N4-hydroxy-5-methylcytidine, N4-hydroxy-5-aminocytidine, N4-hydroxy-5-hydroxycytidine, N4-hydroxy-5-methyl-5-azacytidine, N4-hydroxy-5-amino-5-azacytidine, N4-hydroxy-5-hydroxy-5-azacytidine, N4-hydroxy-5-methylpseudoisocytidine, N4-hydroxy-5-aminopseudoisocytidine, N4-hydroxy-5-hydroxypseudoisocytidine, 2-thio-N4-methyl-5-methylcytidine, 2-thio-N4-methyl-5-aminocytidine, 2-thio-N4-methyl-5-hydroxycytidine, 2-thio-N4-methyl-5-methyl-5-azacytidine, 2-thio-N4-methyl-5-amino-5-azacytidine, 2-thio-N4-methyl-5-hydroxy-5-azacytidine, 2-thio-N4-methyl-5-methylpseudoisocytidine, 2-thio-N4-methyl-5-aminopseudoisocytidine, 2-thio-N4-methyl-5-hydroxypseudoisocytidine, 2-thio-N4-amino-5-azacytidine, 2-thio-N4-aminopseudoisocytidine, 2-thio-N4-amino-5-methylcytidine, 2-thio-N4-amino-5-aminocytidine, 2-thio-N4-amino-5-hydroxycytidine, 2-thio-N4-amino-5-methyl-5-azacytidine, 2-thio-N4-amino-5-amino-5-azacytidine, 2-thio-N4-amino-5-hydroxy-5-azacytidine, 2-thio-N4-amino-5-methylpseudoisocytidine, 2-thio-N4-amino-5-aminopseudoisocytidine, 2-thio-N4-amino-5-hydroxypseudoisocytidine, 2-thio-N4-hydroxy-5-azacytidine, 2-thio-N4-hydroxypseudoisocytidine, 2-thio-N4-hydroxy-5-methylcytidine, N4-hydroxy-5-aminocytidine, 2-thio-N4-hydroxy-5-hydroxycytidine, 2-thio-N4-hydroxy-5-methyl-5-azacytidine, 2-thio-N4-hydroxy-5-amino-5-azacytidine, 2-thio-N4-hydroxy-5-hydroxy-5-azacytidine, 2-thio-N4-hydroxy-5-methylpseudoisocytidine, 2-thio-N4-hydroxy-5-aminopseudoisocytidine, 2-thio-N4-hydroxy-5-hydroxypseudoisocytidine, N6-methyladenosine, N6-aminoadenosine, N6-hydroxyadenosine, 7-deazaadenosine, 8-azaadenosine, N6-methyl-7-deazaadenosine, N6-methyl-8-azaadenosine, 7-deaza-8-azaadenosine, N6-methyl-7-deaza-8-azaadenosine, N6-amino-7-deazaadenosine, N6-amino-8-azaadenosine, N6-amino-7-deaza-8-azaadenosine, N6-hydroxyadenosine, N6-hydroxy-7-deazaadenosine, N6-hydroxy-8-azaadenosine, N6-hydroxy-7-deaza-8-azaadenosine, 6-thioguanosine, 7-deazaguanosine, 8-azaguanosine, 6-thio-7-deazaguanosine, 6-thio-8-azaguanosine, 7-deaza-8-azaguanosine, and 6-thio-7-deaza-8-azaguanosine.

In embodiments, the present methods comprise gene-editing and/or gene correction. In embodiments, the present methods encompass synthetic RNA-based gene-editing and/or gene correction, e.g. with RNA comprising non-canonical nucleotides, e.g. RNA encoding one or more of a nuclease, a transcription activator-like effector nuclease (TALEN), a zinc-finger nuclease, a meganuclease, a nickase, a clustered regularly interspaced short palindromic repeat (CRISPR)-associated protein a DNA-repair protein, a DNA-modification protein, a base-modification protein, a DNA methyltransferase, a protein that causes DNA demethylation, an enzyme for which DNA is a substrate or a natural or engineered variant, family-member, orthologue, fragment or fusion construct thereof. In embodiments, the efficiency of the gene-editing and/or gene correction is high, for example, higher than DNA-based gene editing and/or gene correction. In embodiments, the present methods of gene-editing and/or gene correction are efficient enough for in vivo application. In embodiments, the present methods of gene-editing and/or gene correction are efficient enough to not require cellular selection (e.g. selection of cells that have been edited). In embodiments, the efficiency of gene-editing of the present methods is about 1%, or about 2%, or about 3%, or about 4%, or about 5%, or about 6%, or about 7%, or about 8%, or about 9%, or about 10%, or about 20%, or about 30%, or about 40%, or about 50%, or about 60%, or about 70%, or about 80%, or about 90%, or about 100%. In embodiments, the efficiency of gene-correction of the present methods is about 1%, or about 2%, or about 3%, or about 4%, or about 5%, or about 6%, or about 7%, or about 8%, or about 9%, or about 10%, or about 20%, or about 30%, or about 40%, or about 50%, or about 60%, or about 70%, or about 80%, or about 90%, or about 100% In embodiments, the present methods comprise high-efficiency gene-editing proteins comprising engineered nuclease cleavage or DNA-modification domains. In embodiments, the methods comprise high-fidelity gene-editing proteins comprising engineered nuclease cleavage or DNA-modification domains. In embodiments, the high-efficiency gene-editing proteins comprising engineered DNA-binding domains. In embodiments, the high-fidelity gene-editing proteins comprising engineered DNA-binding domains. In embodiments, the methods comprise gene-editing proteins comprising engineered repeat sequences. In embodiments, the methods comprise gene-editing proteins comprising one or more CRISPR associated family members. In embodiments, the methods comprise altering the DNA sequence of a cell by transfecting the cell with or inducing the cell to express a gene-editing protein. In embodiments, the methods comprise altering the DNA sequence of a cell that is present in an in vitro culture. In embodiments, the methods comprise altering the DNA sequence of a cell that is present in vivo.

In embodiments, the methods comprise one or more steroids and/or one or more antioxidants in the transfection medium can increase in vivo transfection efficiency, in vivo reprogramming efficiency, and in vivo gene-editing efficiency. In embodiments, the methods comprise contacting a cell or patient with a glucocorticoid, such as hydrocortisone, prednisone, prednisolone, methylprednisolone, dexamethasone or betamethasone. In embodiments, the methods comprise inducing a cell to express a protein of interest by contacting a cell with a medium containing a steroid and contacting the cell with one or more nucleic acid molecules. In embodiments, the nucleic acid molecule comprises synthetic RNA. In embodiments, the steroid is hydrocortisone. In embodiments, the hydrocortisone is present in the medium at a concentration of between about 0.1 uM and about 10 uM, or about 1 uM. In embodiments, the methods comprise inducing a cell in vivo to express a protein of interest by contacting the cell with a medium containing an antioxidant and contacting the cell with one or more nucleic acid molecules. In embodiments, the antioxidant is ascorbic acid or ascorbic-acid-2-phosphate. In embodiments, the ascorbic acid or ascorbic-acid-2-phosphate is present in the medium at a concentration of between about 0.5 mg/L and about 500 mg/L, including about 50 mg/L. In embodiments, the methods comprise reprogramming and/or gene-editing a cell in vivo by contacting the cell with a medium containing a steroid and/or an antioxidant and contacting the cell with one or more nucleic acid molecules, wherein the one or more nucleic acid molecules encodes one or more reprogramming and/or gene-editing proteins. In embodiments, the cell is present in an organism, and the steroid and/or antioxidant are delivered to the organism.

In embodiments, the nucleic acid therapeutic agent encodes a gene-editing protein and/or associated elements for gene-editing functionality. In embodiments, the gene-editing protein is selected from a zinc finger (ZF), transcription activator-like effector (TALE), meganuclease, and clustered regularly interspaced short palindromic repeat (CRISPR)-associated protein. In embodiments, the CRISPR-associated protein is selected from Cas9, CasX, CasY, Cpf1, and gRNA complexes thereof. In embodiments, the CRISPR-associated protein is selected from Cas9, xCas9, Cas12a (Cpf1), Cas13a, Cas14, CasX, CasY, a Class 1 Cas protein, a Class 2 Cas protein, MAD7, and gRNA complexes thereof.

In embodiments, the therapeutic agent is a biologic therapeutic agent. In embodiments, the biologic therapeutic agent is a protein. In embodiments, the biologic therapeutic agent is an interferon, a monoclonal antibody, and/or an interleukin. In embodiments, the biologic therapeutic agent is used to effect immunotherapy selected from one or more of specific active immunotherapy, nonspecific active immunotherapy, passive immunotherapy, and cytotoxic therapy.

In embodiments, the biologic therapeutic agent is a recombinant protein.

In embodiments, the biologic therapeutic agent is a virus.

In embodiments, the biologic therapeutic agent is one of an antibody or an antibody fragment, fusion protein, gene-editing protein, cytokine, antigen, and peptide.

In embodiments, the therapeutic agent is a small molecule therapeutic agent. In embodiments, the small molecule therapeutic agent is one or more of a drug, inhibitor, or cofactor. In embodiments, the drug for use in cancer therapy. In embodiments, the inhibitor is one or more of a kinase inhibitor, proteasome inhibitor, and inhibitor targeting apoptosis.

In embodiments, the therapeutic agent is a vaccine and/or an immunogenic antigen.

Pharmaceutical Compositions

In one aspect, the disclosure provides compositions useful for treating Fanconi Anemia (FA), wherein the composition comprises megakaryocyte-derived extracellular vesicles of the disclosure. In another aspect, the disclosure provides a composition useful for treating Fanconi Anemia (FA) comprising a plurality of substantially purified megakaryocyte-derived extracellular vesicles comprising a lipid bilayer membrane surrounding a lumen, wherein: the megakaryocyte-derived extracellular vesicle lumen comprises cargo and/or cargo is associated with the surface of the megakaryocyte-derived extracellular vesicles; and the lipid bilayer membrane comprises one or more proteins associated with or embedded within. In embodiments, the cargo comprises one or more agents useful for the treatment of Fanconi Anemia (FA). In embodiments, the agent is one or more therapeutic agents, including therapeutic agents useful for the treatment of Fanconi Anemia (FA).

Therapeutic treatments comprise the use of one or more routes of administration and of one or more formulations that are designed to achieve a therapeutic effect at an effective dose, while minimizing toxicity to the patient to which treatment is administered.

In embodiments, the effective dose is an amount that substantially avoids cell toxicity in vivo. In various embodiments, the effective dose is an amount that substantially avoids an immune reaction in a human patient. For example, the immune reaction may be an immune response mediated by the innate immune system. Immune response can be monitored using markers known in the art (e.g. cytokines, interferons, TLRs). In embodiments, the effective dose obviates the need for treatment of the human patient with immune suppressants agents used to moderate the residual toxicity.

Upon formulation, solutions may be administered in a manner compatible with the dosage formulation and in such amount as is therapeutically effective, as described herein. The formulations may easily be administered in a variety of dosage forms such as injectable solutions and the like. For parenteral administration in an aqueous solution, for example, the solution generally is suitably buffered and the liquid diluent first rendered isotonic with, for example, sufficient saline or glucose. Such aqueous solutions may be used, for example, for intravenous, intramuscular, subcutaneous and intraperitoneal administration. Preferably, sterile aqueous media are employed as is known to those of skill in the art.

Pharmaceutical preparations may additionally comprise delivery reagents (a.k.a. "transfection reagents", a.k.a. "vehicles", a.k.a. "delivery vehicles") and/or excipients. Pharmaceutically acceptable delivery reagents, excipients, and methods of preparation and use thereof, including methods for preparing and administering pharmaceutical preparations to patients are well known in the art, and are set forth in numerous publications, including, for example, in US Patent Appl. Pub. No. US 2008/0213377, the entirety of which is incorporated herein by reference. In aspects, the present disclosure relates to a pharmaceutical composition comprising a composition disclosed herein and a pharmaceutically acceptable excipient or carrier.

For example, the pharmaceutical compositions can be in the form of pharmaceutically acceptable salts. Such salts include those listed in, for example, *J. Pharma. Sci.* 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety. Non-limiting examples of pharmaceutically acceptable salts include: sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, tartarate salts, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like.

The present pharmaceutical compositions can comprise excipients, including liquids such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In embodiments, the pharmaceutically acceptable excipients are sterile when administered to a patient. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents.

In embodiments, the pharmaceutical composition is formulated for one or more of topical, intrathecal, intra-lesional, intra-coronary, intravenous (IV), intra-articular, intramuscular, intra-nasal, and intra-endobronchial administration and administration via intrapancreatic endovascular injection, intra-nucleus pulposus, lumbar puncture, intra-myocardium, transendocardium, intra-fistula tract, intermedullary space, intra-nasal, and intradural space injection.

In embodiments, the pharmaceutical composition is formulated for infusion. In embodiments, the pharmaceutical composition is formulated for infusion, wherein the pharmaceutical composition is delivered to the bloodstream of a patient through a needle in a vein of the patient through a peripheral line, a central line, a tunneled line, an implantable port, and/or a catheter. In embodiments, the patient may also receive supportive medications or treatments, such as hydration, by infusion. In embodiments, the pharmaceutical composition is formulated for intravenous infusion. In embodiments, the infusion is continuous infusion, secondary intravenous therapy (IV), and/or IV push. In embodiments, the infusion of the pharmaceutical composition may be administered through the use of equipment selected from one or more of an infusion pump, hypodermic needle, drip chamber, peripheral cannula, and pressure bag.

In embodiments, the pharmaceutical composition is introduced into or onto the skin, for instance. intraepidermally, intradermally or subcutaneously, in the form of a cosmeceutical (see, e.g., Epstein, H., Clin. Dermatol. 27(5):453-460 (2009)). In embodiments, the pharmaceutical composition is in the form of a cream, lotion, ointment, gel, spray, solution and the like. In embodiments, the pharmaceutical composition further includes a penetration enhancer such as, but not limited to, surfactants, fatty acids, bile salts, chelating agents, non-chelating non-surfactants, and the like. In embodiments, the pharmaceutical composition may also include a fragrance, a colorant, a sunscreen, an antibacterial and/or a moisturizer.

In order that the disclosure disclosed herein may be more efficiently understood, examples are provided below. It should be understood that these examples are for illustrative purposes only and are not to be construed as limiting the disclosure in any manner.

EXAMPLES

Example 1: Megakaryocyte-Derived Extracellular Vesicle Generation

A cell culture process was adapted to produce allogeneic megakaryocyte-derived extracellular vesicles from primary human peripheral blood CD34+ hematopoietic stem cells (HSCs) (FIG. 1A).

Primary human CD34+ HSCs sourced from a commercial supplier were thawed and transitioned from a stem cell maintenance medium to an HSC expansion medium. During this period, HSCs expanded significantly. These cultures were then placed in a megakaryocyte differentiation medium, and megakaryocyte-derived extracellular vesicles were collected from culture supernatant. Biomarker expression of CD41, CD61, CD42b, megakaryocyte-specific cytoskeletal proteins β1-tubulin, alpha granule components (platelet factor 4 and von Willebrand Factor), secretory granules, and ultrastructural characteristics (invaginated membrane system, dense tubular system, multivesicular bodies) confirmed megakaryocyte differentiation. Megakaryocytes yielded between 500-1500 megakaryocyte-derived extracellular vesicles/cell, which were between 30-600 nm in diameter, 100-300 nm, DNA−, CD41+. Megakaryocyte-derived extracellular vesicles were further isolated/concentrated by tangential flow filtration and packaged at targeted concentrations of $1.5\times10^8$ megakaryocyte-derived extracellular vesicles/mL. Megakaryocyte-derived extracellular vesicles exhibited robust expression of megakaryocytes and platelet-specific biomarkers, RNA, and cytosolic proteins.

Nanoparticle analysis, flow cytometry, and cryo transmission electron microscopy confirmed biomarker expression and composition.

Figure 1B:
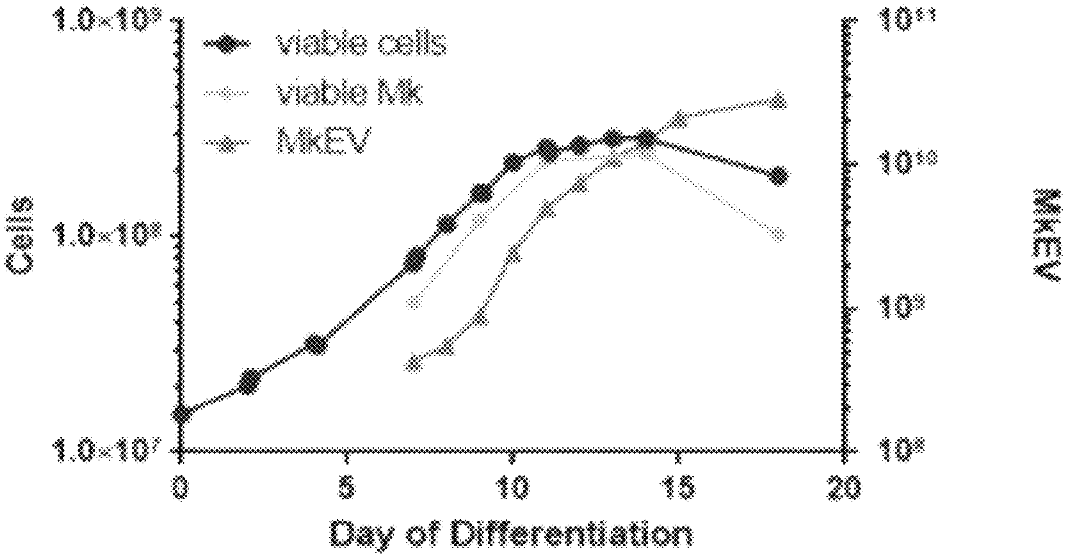
FIG. 1B is a graph of experimental data showing that the yield of megakaryocyte-derived extracellular vesicles increases over time during in vitro megakaryocyte (Mk) differentiation. For reference, at the last point, the order top to bottom is MkEV, viable cells, and viable MK.
Figure 1C:
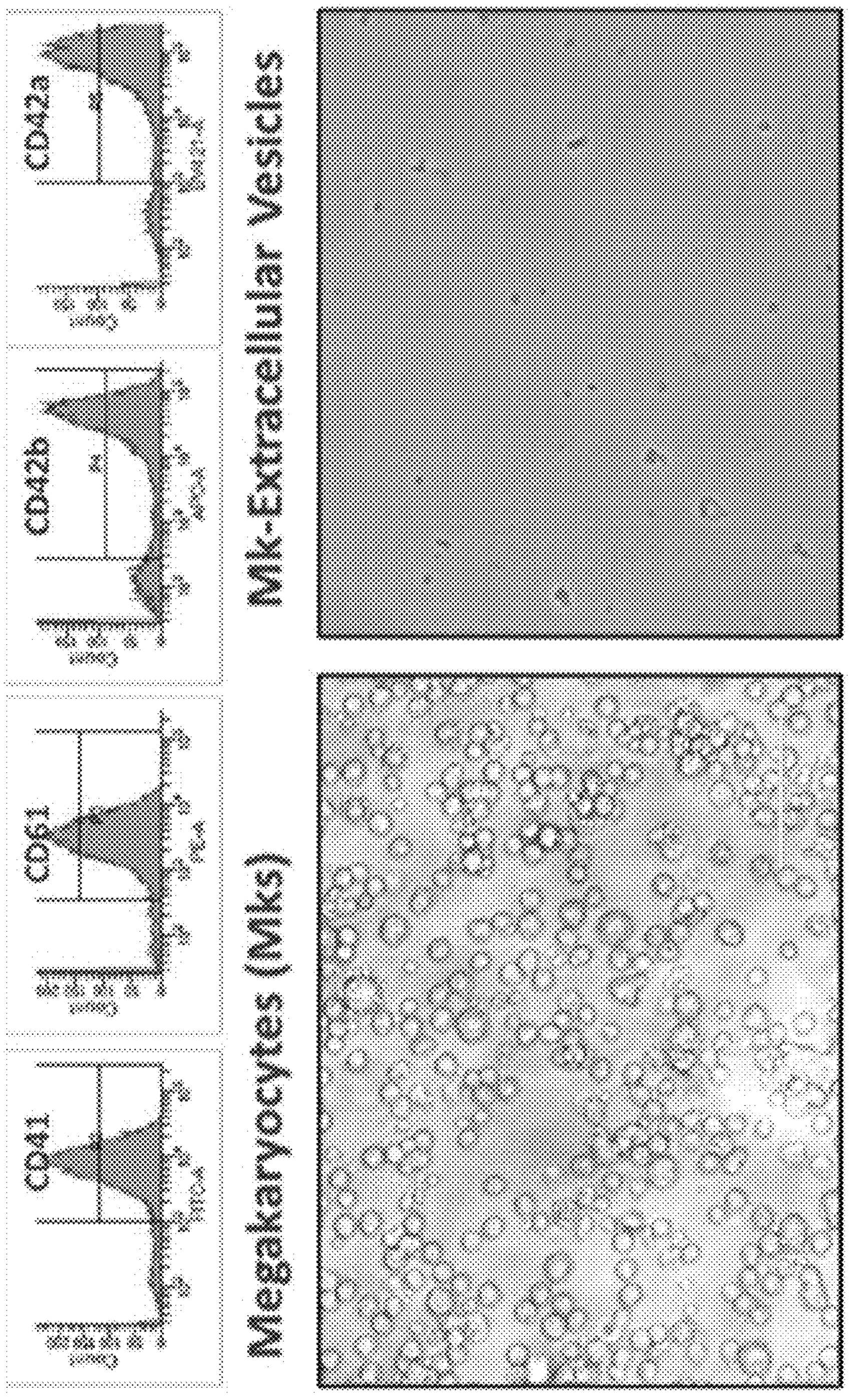
FIG. 1C is experimental data showing the phenotype of MkEVs in culture. Top panel: Representative histograms of cellular surface marker expression. Bottom panel: Representative microscopy images of megakaryocytes (left), and harvested MkEVs (right).

The yield of MkEVs was found to increase over time during in vitro megakaryocyte (Mk) differentiation (FIG. 1B). The phenotype of MkEVs in culture was assessed (FIG. 1C), and representative histograms of cellular surface marker expression and microscopy images of megakaryocytes and harvested MkEVs were produced.

Figure 2A:
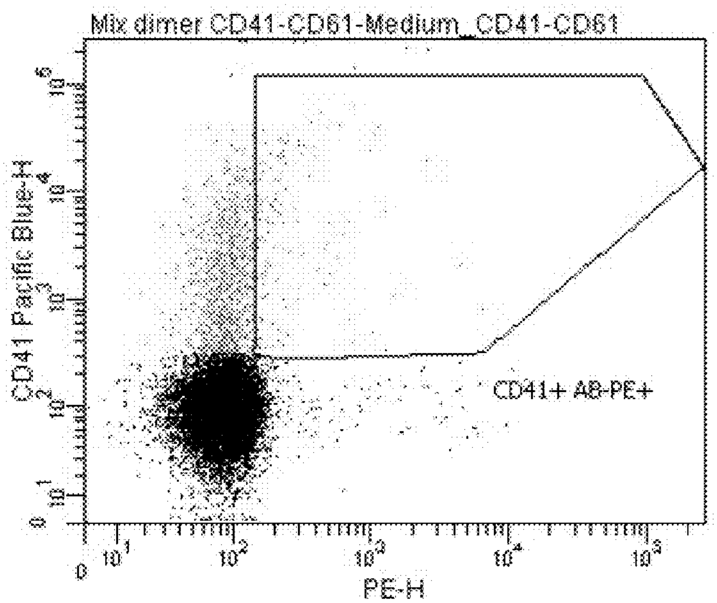
FIGS. 2A-2F demonstrate experimental data showing MkEV biomarker expression. Surface marker expression of MkEVs of the disclosure were compared to platelet-free plasma (PFP) MkEVs and platelet-derived EVs (PLT EVs).
Figure 2B:
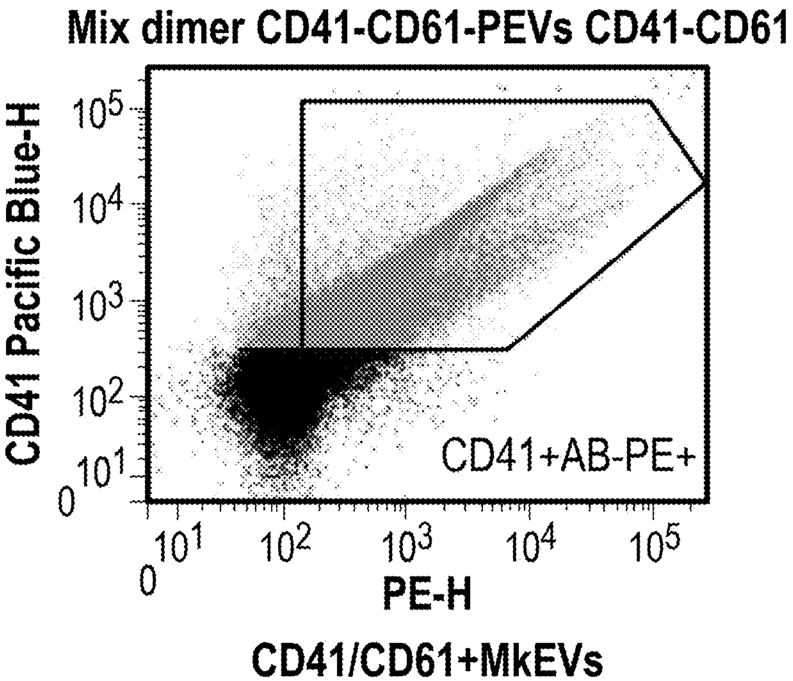
Figure 2C:
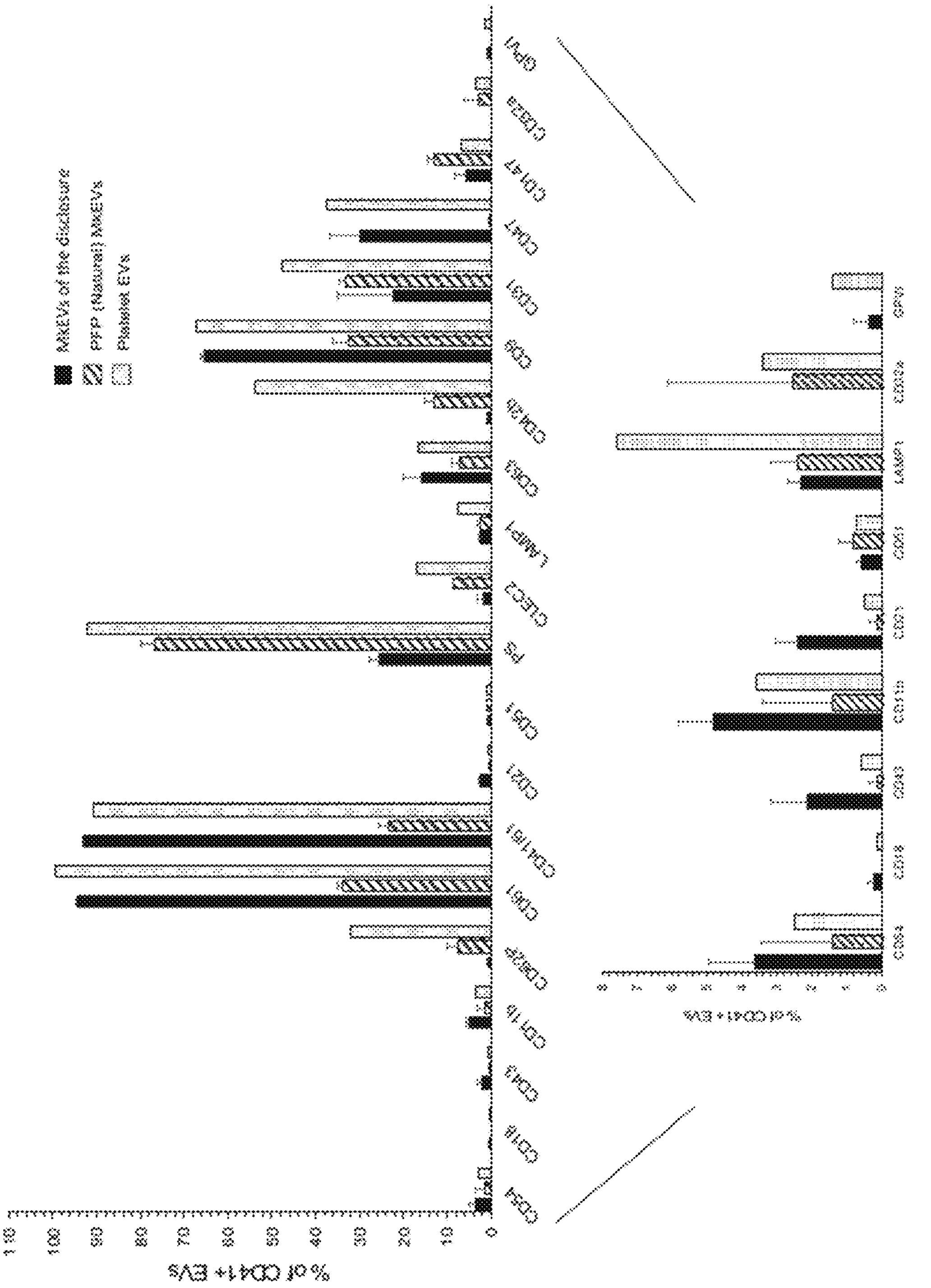
Figure 2D:
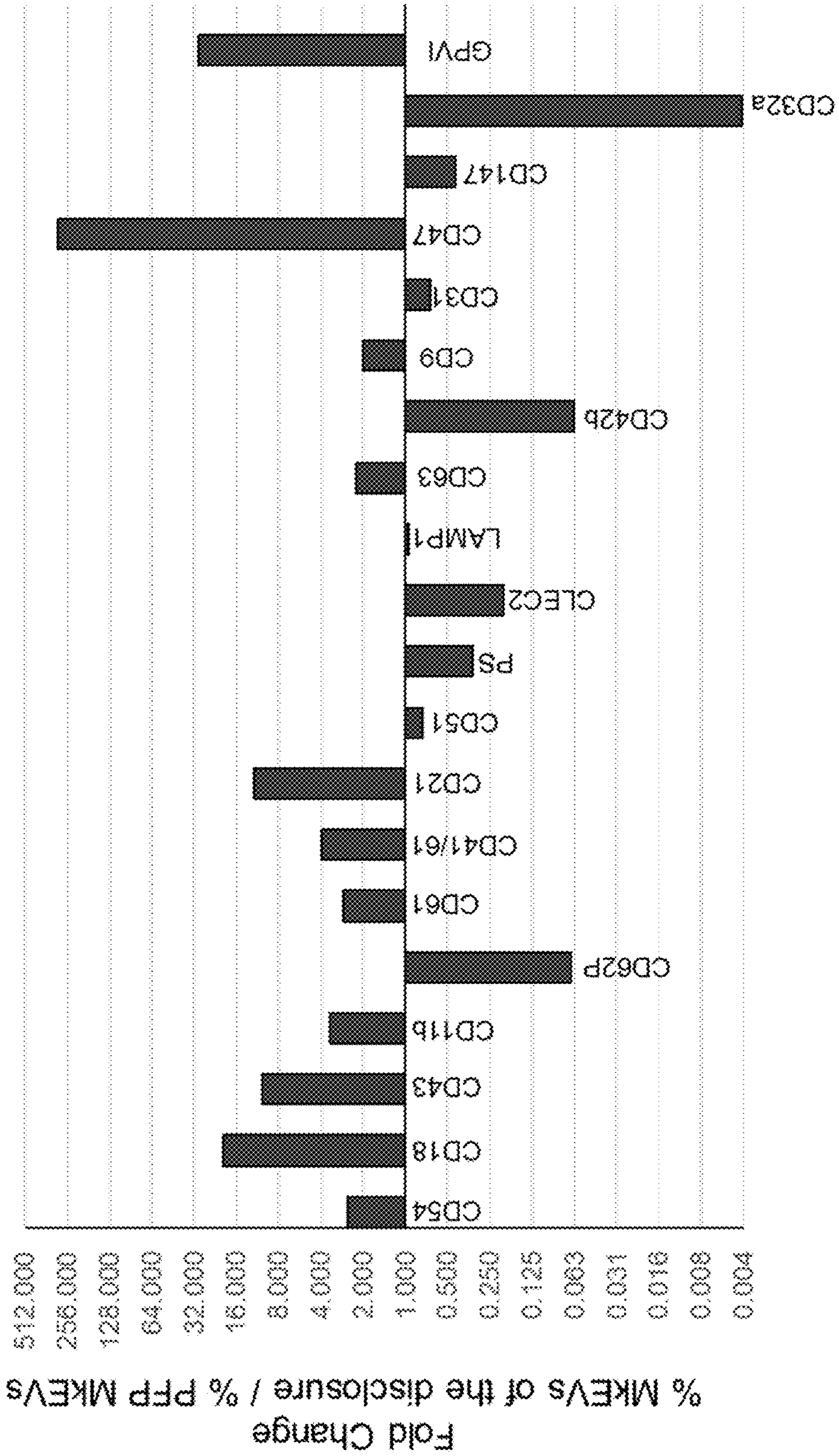
Figure 2E:
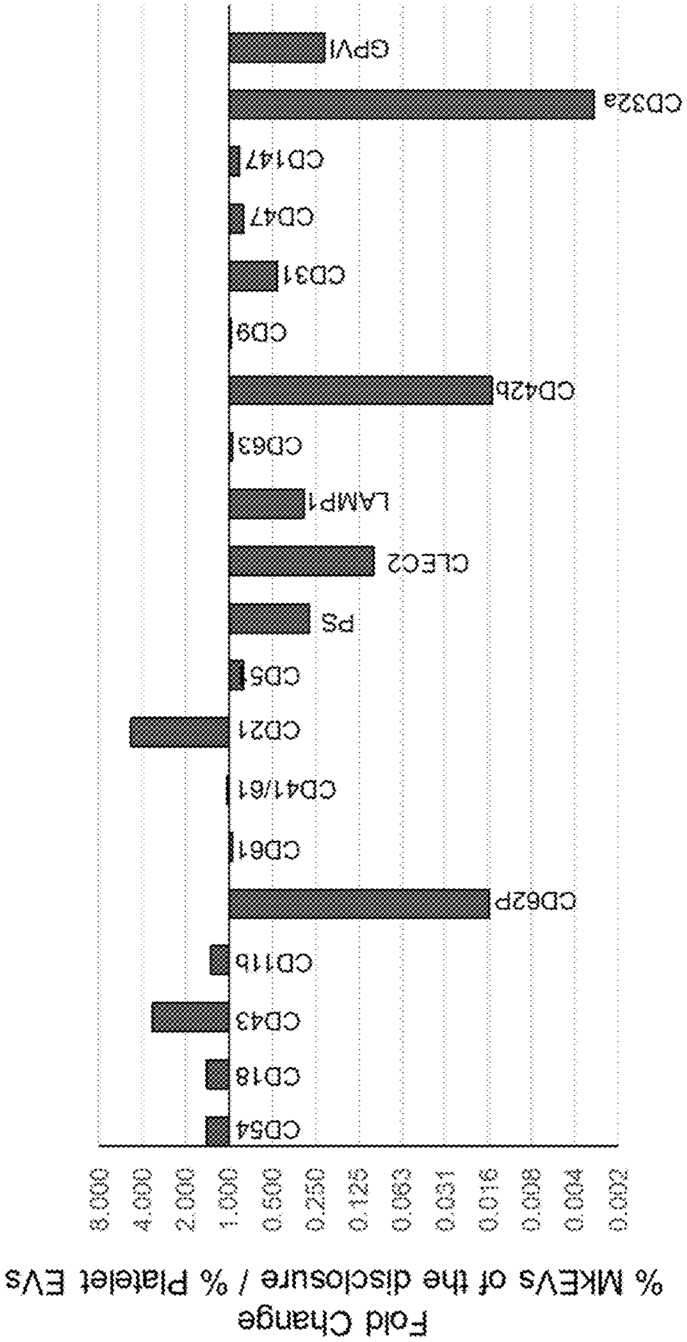
Figure 2F:
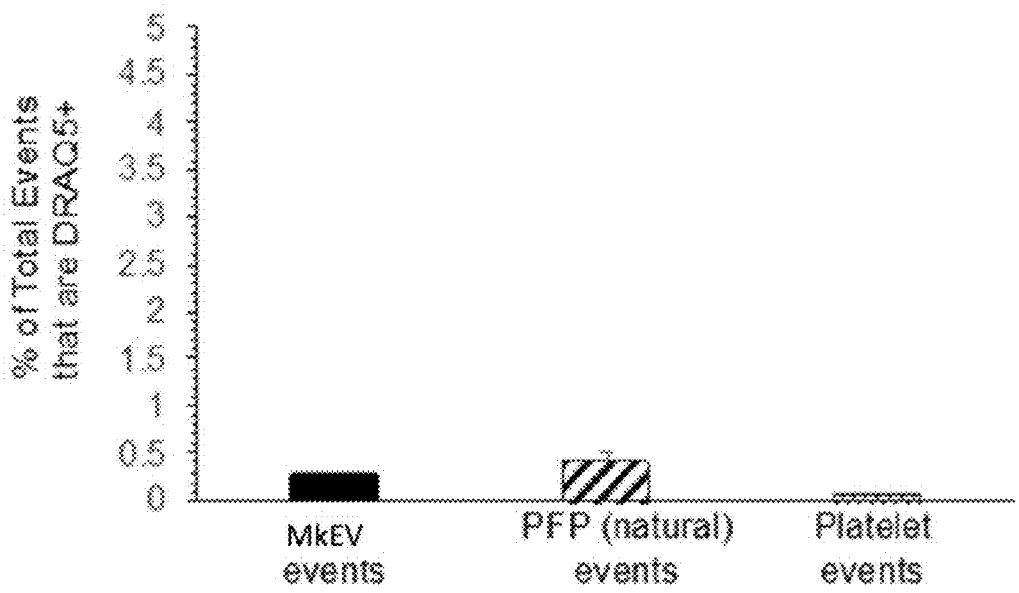

MkEV biomarker expression was examined. Surface marker expression of MkEVs of the disclosure were compared to platelet-free plasma (PFP) MkEVs and platelet-derived EVs (PLT EVs) (FIGS. 2A-2E). Representative graphs demonstrating the flow cytometry gating strategy (FIGS. 2A-2B), the marker profile of CD41+ MKEVs of the disclosure, CD41+ PFP MkEVs, and CD41+ PLT EVs (FIG. 2C) and the fold change in marker expression between MkEVs of the disclosure and PFP MkEVs (FIG. 2D) and MkEVs of the disclosure and PLT EVs (FIG. 2E) are shown. The data shows that MkEVs of the disclosure exhibit different expression of surface markers compared to PFP MkEVs and PLT EVs and establish a marker profile of the present MkEVs relative to PFP MkEVs and PLT EVs. The minimal presence of DRAQ5 positive events show the lack of cellular contamination (FIG. 2F).

Figure 3A:
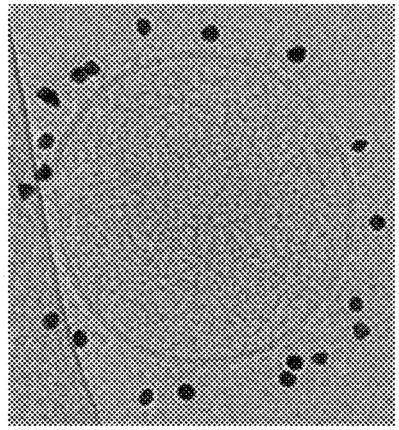
FIGS. 3A-3B are electron microscopic images demonstrating MkEV characterization, including size and morphology.
Figure 3B:
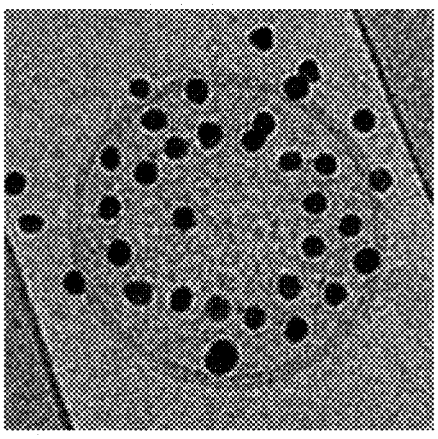
Figure 3C:
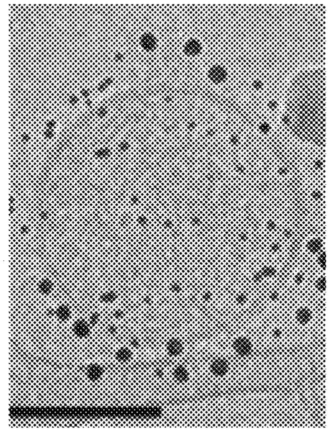
FIG. 3C is an image of MkEVs isolated from PFP plasma with co-staining of CD41 (large dots) and PS (small dots).

The size and morphology of MkEVs of the disclosure were characterized. Cryo-EM images of MkEVs of the disclosure with immunogold labeling of CD41 (FIG. 3A) and phosphatidylserine (FIG. 3B) were prepared. Measuring of MkEVs in cryo-EM images showed a range of MkEV sizes between 100-300 nm, averaging ~250 nm in diameter. FIG. 3C is an image of MkEVs isolated from PFP plasma with co-staining of CD41 (large dots) and PS (small dots) (see Brisson et al., Platelets 28:263-271 (2017), which is incorporated by reference herein in its entirety). Regarding organelle content, preliminary analysis has shown no evidence of mitochondria in MkEVs, as assessed by (1) electron microscopy, and (2) mitochondrial respiration analysis (Agilent Seahorse). Genomic analysis is conducted by sequencing of coding RNAs and non-coding miRNAs. Proteomic analysis is conducted using mass spectrometry, and proteomic data validates flow and EM surface markers.

Figure 4A:
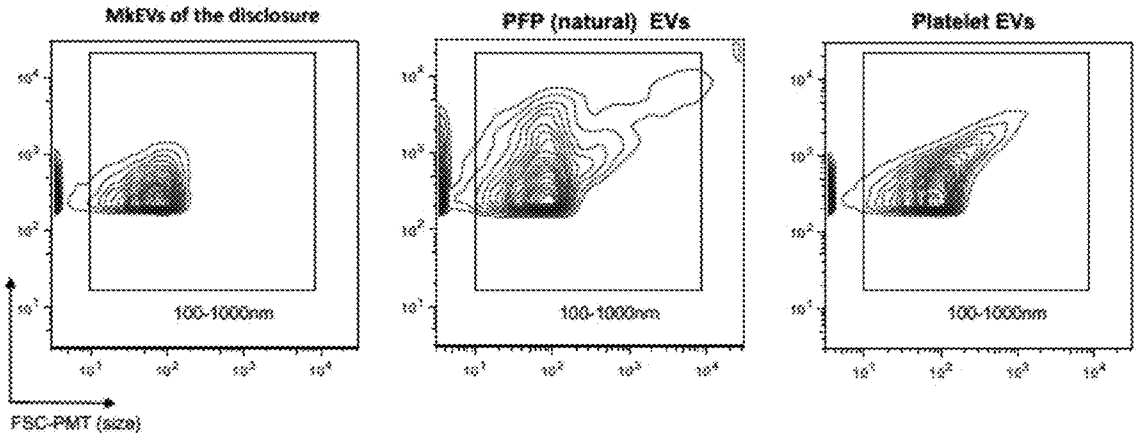
FIG. 4A shows the size distribution (nm) of CD41+ MkEVs of the disclosure compared to CD41+ PFP MkEVs and platelet EVs. Flow cytometric analysis with fluorescent CD41+ antibody labeling was used.
Figure 4B:
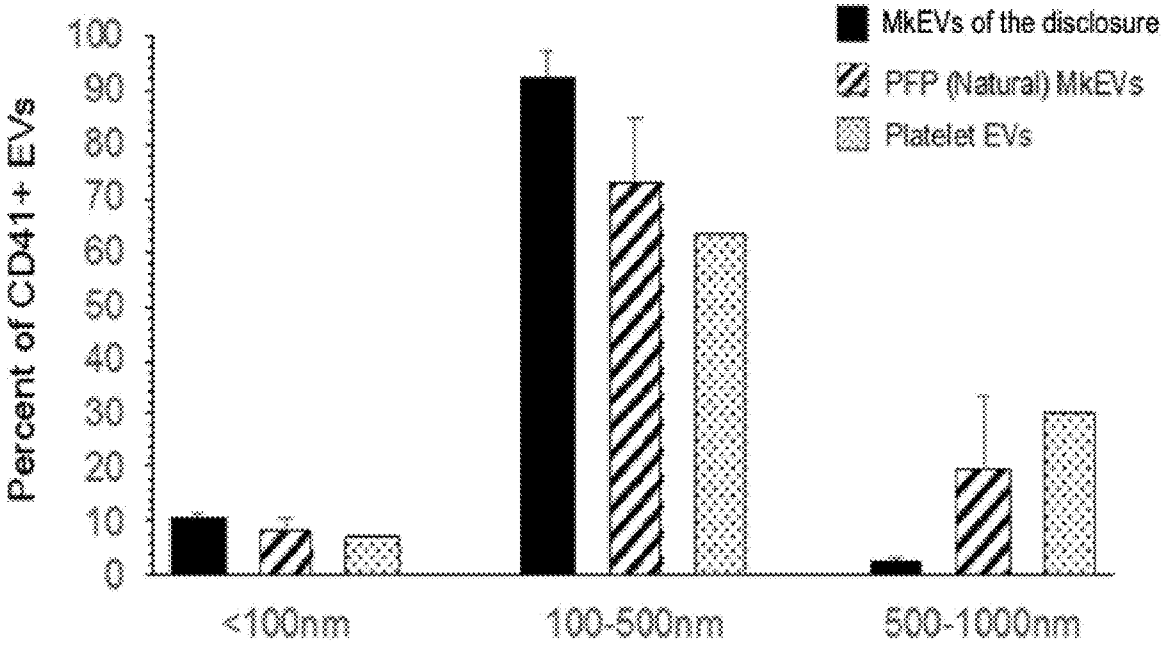
FIG. 4B is a graph showing the size distribution of the CD41+ MkEVs of the disclosure compared to CD41+ PFP (Natural MkEVs and platelet CD41+ EVs.
Figure 4C:
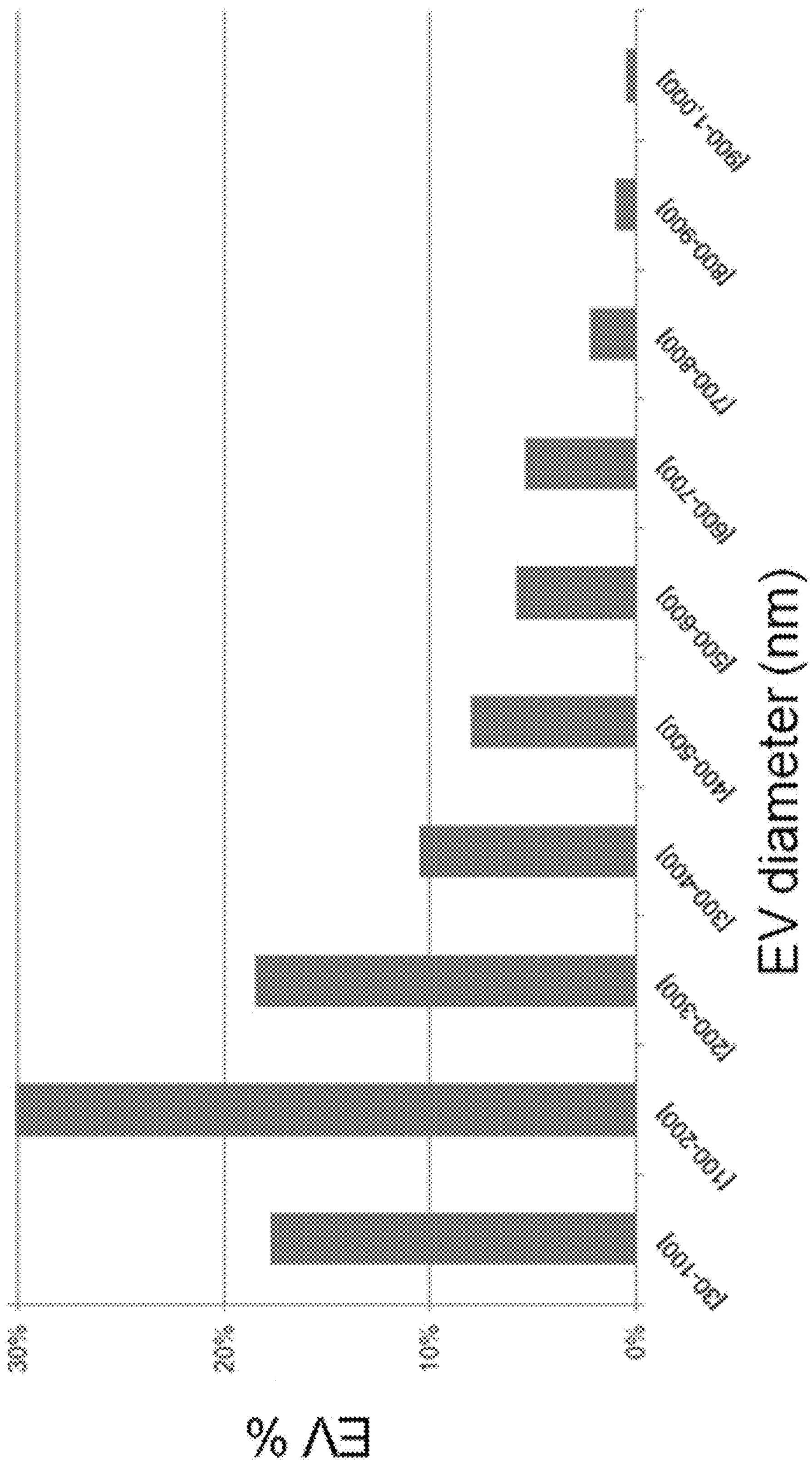
FIG. 4C is a graph showing the percent size distribution of the EVs (nm).
Figure 4D:
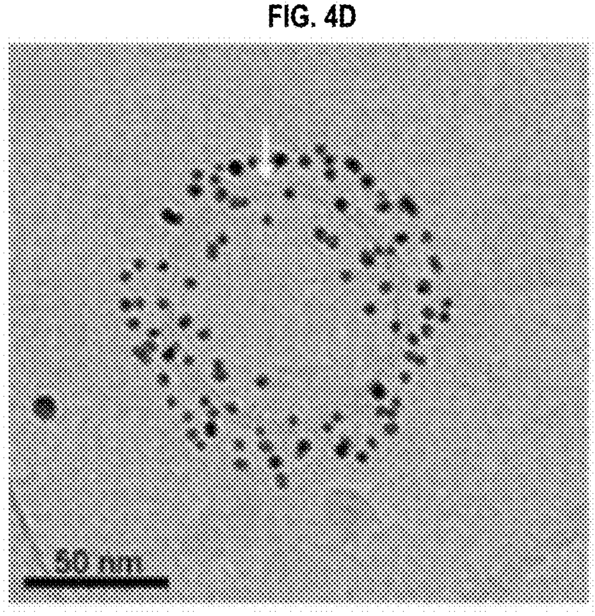
FIGS. 4D-4E are cryo-EM images of PFP MkEVs.
Figure 4E:
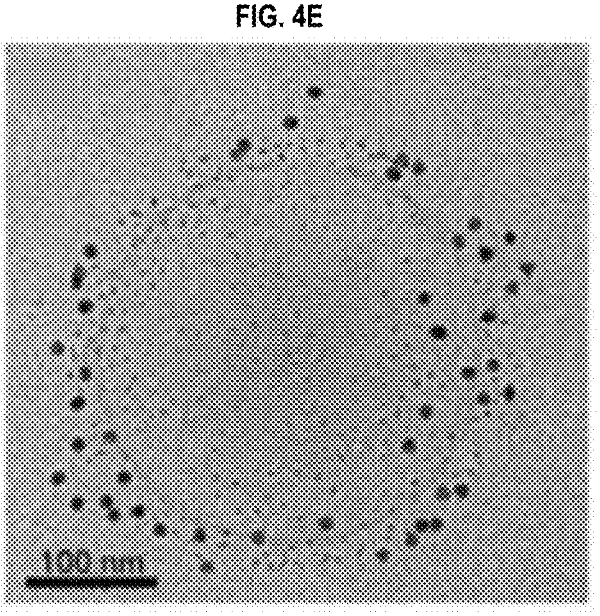
Figure 4F:
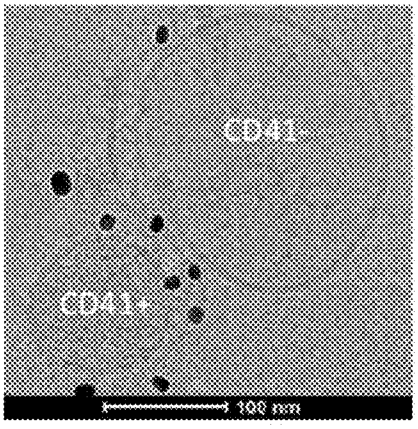
FIGS. 4F-4K are cryo-EM images of MkEVs of the disclosure. Cd41+ Immunogold labeling was used and visible as black dots.
Figure 4G:
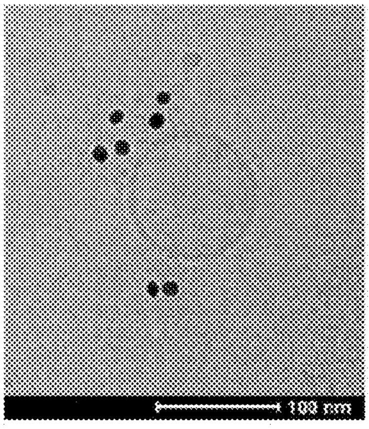
Figure 4H:
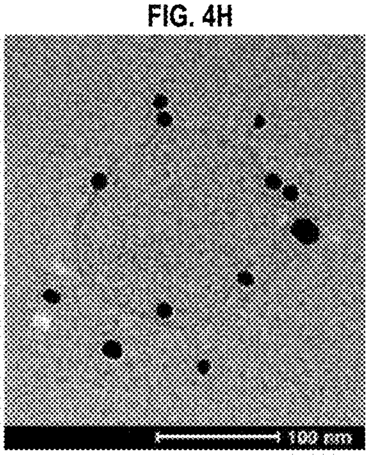
Figure 4I:
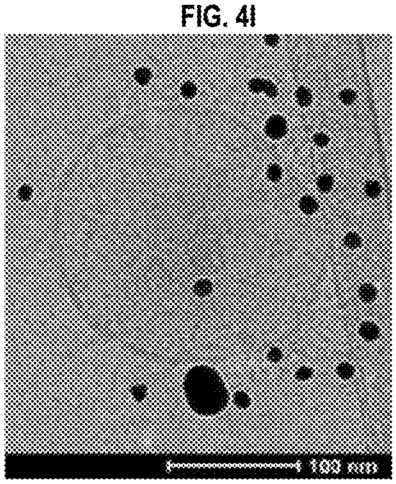
Figure 4J:
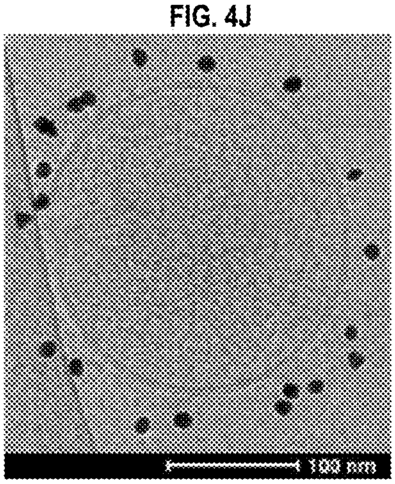
Figure 4K:
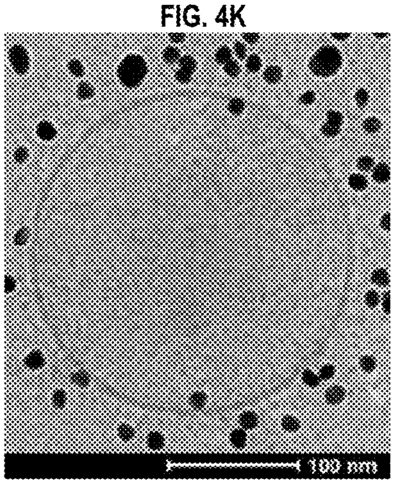

The size of MkEVs of the disclosure is compared with PFP MkEVs using flow cytometric analysis and cryo-EM analysis with CD41+ immunogold labeling. The size distribution of MkEVs of the disclosure overlapped but were different than the size distribution of PFP MkEVs and platelet-derived EVs (FIGS. 4A-4K). (FIG. 4C is adapted from Arraud et al., Journal of Thrombosis and Haemostasis 12:614-627 (2014); FIGS. 4D and 4E are found in Brisson et al., Platelets 28:263-271 (2017), all of which are incorporated by reference herein in their entireties).

Figure 5A:
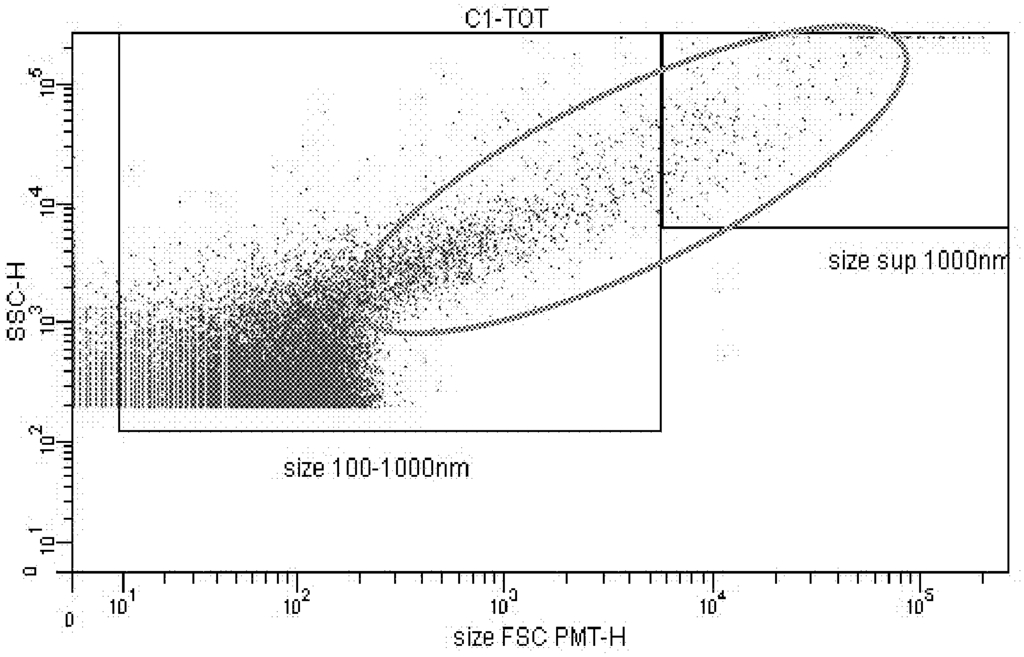
FIGS. 5A-5B are graphs of experimental data showing that size exclusion filtration effectively removes aggregates from unfiltered product.
Figure 5B:
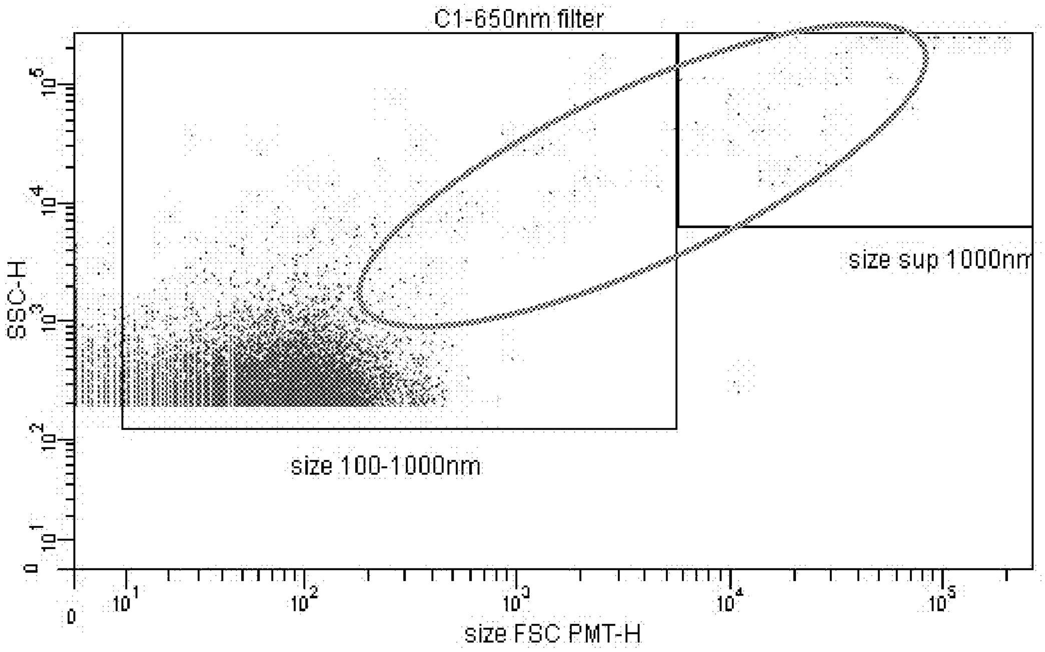

Purification of MkEVs was also examined, and size exclusion filtration was found to effectively remove aggregates from unfiltered product. For example, post-harvest filtration with a 650 nm size exclusion filter was found to successfully clear large aggregate material (observed by EM in frozen MkEV samples) (FIG. 5B) compared to unfiltered MkEV product (FIG. 5A).

Example 2: MV Manufacturing Process and Release of Product for In Vivo Gene Delivery This example is related to processes for standardizing and scaling manufacturing and isolating MkEVs from primary human CD34+ HSCs. MkEVs were characterized and inter-batch variability and release testing was performed. Gene loading and transfection efficiency for MkEVs was defined, which allows for tracking in vivo biodistribution and efficacy, and defining product parameters for gene delivery applications.

For clinical entry, MkEV manufacture must meet release criteria including standardization of tissue sourcing, manufacturing, yield, testing, and storage. MkEV quality and inter-batch variability regarding identity, purity, efficacy, and yield was defined and used to define product release criteria. MkEVs met or exceed minimum quality and storage requirements.

MkEV manufacture from primary human CD34+ cells were adapted to ~400 mL batch cultures (approx. 1200 $cm^2$ of culture area, which is equivalent to ~5× T225s) to yield ~8e10 MkEVs per batch. MkEVs underwent testing to assess identity & purity (biomarker expression, % composition) and yield (total MkEV events per batch). Table 1 shows examples of MkEV release specifications.

TABLE 1

Examples of MkEV release specifications

| TEST | METHOD | SPECIFICATIONS |
|---|---|---|
| Identity/ Purity | | |
| Size | Nanoparticle analyzer | ≥95% 100-600 nm |
| DNA | High sensitivity flow cytometry | ≥95% DRAQ5 negative |
| CD41 | High sensitivity flow cytometry | ≥50% positive |
| Yield | | |
| MV Events | Nanoparticle analyzer | ≥1e10 per batch |

Standardization and scale processes to manufacture and isolate MkEVs from primary human CD34+ HSCs: Primary human CD34+ hematopoietic stem cells (HSCs) were utilized. Initial isolation, enrichment, and banking of HSCs (90-95% purity) was performed and qualified according to FDA guidance using a range of assays to demonstrate identity, sterility, viability and bank stability. HSCs were mobilized from donor marrow to the blood by granulocyte-colony stimulating factor, and collected from peripheral blood by apheresis, and tested for Chagas, CMV, HepB, HepC, HIV-1/HIV-2 Plus 0, HTLV I/II, Syphilis, HBV, HCV, and WNV prior to banking (COVID-19 testing is included). HSC vials were cryopreserved in clinically approved media prior to shipping and exhibit viability post thawing. In a non-limiting example, HSC vials were cryopreserved in clinically approved media prior to shipping and exhibit viability post thawing.

Process Flow for Initial Stage MkEV Production: A scalable, cGMP-compatible process to manufacture MVs from HSCs was utilized. MkEV production was divided into 2 discontinuous segments: (A) HSC expansion, megakaryocyte differentiation and MkEV production, and (B) MV isolation/concentration by tangential flow filtration and vial filling (1.5e8 MVs/mL). MkEV vials were cryopreserved for banking. Centralized manufacturing is intended for HSC expansion and MkEV production/processing/filling.

Segment A: Primary human CD34+ HSCs at a 5e6 cells/batch underwent ~30-fold biomass expansion during cell culture to yield ~1.5e8 megakaryocytes/batch. CD34+ HSC differentiation to megakaryocyte progenitor occurred over a period of 7-9 days. Each megakaryocyte yielded between 500-1500 MVs, resulting in a total batch yield of ~7.5e10 MkEVs/batch prior to harvesting from supernatant.

Segment B: MkEVs were isolated/concentrated by tangential flow filtration (differential centrifugations as alternative if necessary) to reduce volume to ~500 mL. MkEVs were packaged at a concentration of ~1.5e8 MkEVs/mL to yield ~500 vials/batch.

Example 3: Characterization of MkEVs and Performance of Inter-Batch Variability and Release Testing MkEVs were collected from batch processing. High sensitivity flow cytometry was used to determine surface biomarker expression (CD41, CD62P, CLEC-2, LAMP-1 (CD107A)), organelle content (mitochondria), and phospholipid composition (phosphatidylserine) in combination with a nuclear dye (DRAQ5) to distinguish from nucleated cells. Total fluorescence intensity was calculated after subtraction of a fluorophore-conjugated IgG antibody specificity control. The forward and side light scatter of MkEVs were examined to evaluate size distribution, purity, and aggregation. Size-defined nanoparticles served as a gating control. MkEV size and total batch yield were determined using a nanoparticle analyzer (Nanosight, Malvern Instruments).

MkEV protein content (Alix and TSG101) was determined by ELISA and DNA content measured to estimate potential contamination by cell debris and nuclei. MkEV integrity and purity was confirmed by cryo-electron microscopy and immunogold labeling and permit further determination of surface molecules (CD41, phosphatidylserine). These experiments were repeated a number of times per batch for a number of independent MkEV batches. In a non-limiting example, the experiments were repeated at least 3 times per batch for a minimum of 3 independent MkEV batches. MkEVs/PEVs from human whole blood were used as a positive control.

Figure 6A:
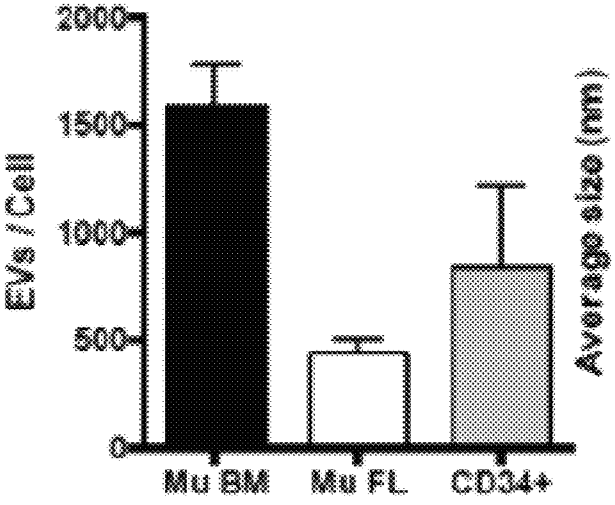
FIGS. 6A-6H are graphs of experimental data showing EV characterization. EVs were collected from media containing mature, cultured MKs 24 hours after megakaryocyte isolation and purification. Isolated human platelets were stimulated with either thrombin (0.1 U/mL) and collagen (1 μg/mL) (traditional platelet agonists) or LPS (5 μg/mL). EV number/platelet and size were measured via nanoparticle tracking analysis (FIGS. 6A, 6B, 6E, and 6F) and CD41 receptor positivity and amount by electron microscopy (FIGS. 6C, 6D, 6G, and 6H).
Figure 6B:
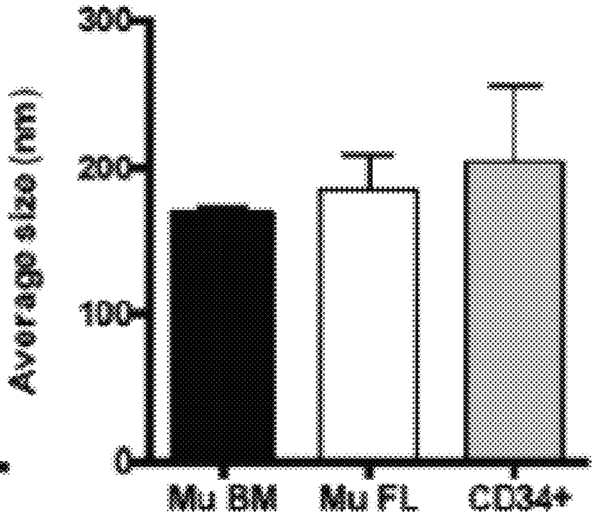
Figure 6C:
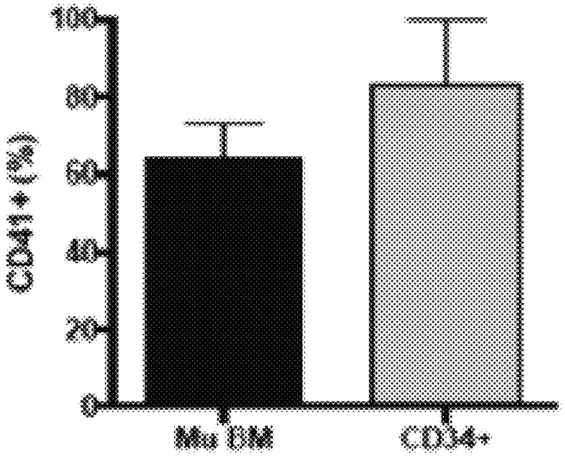
Figure 6D:
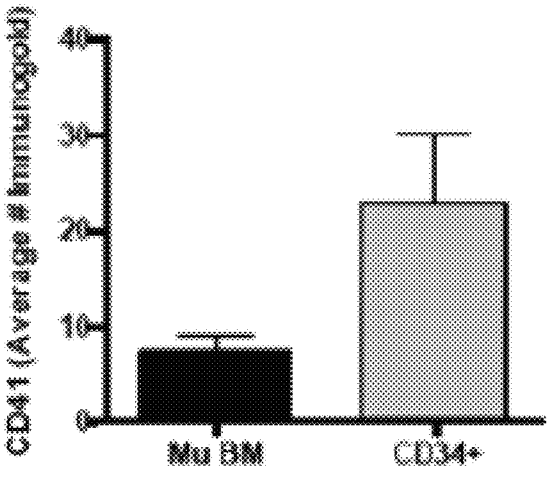
Figure 6E:
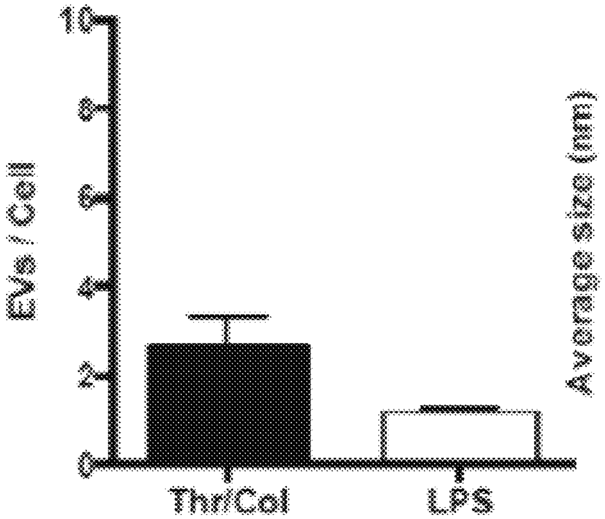
Figure 6F:
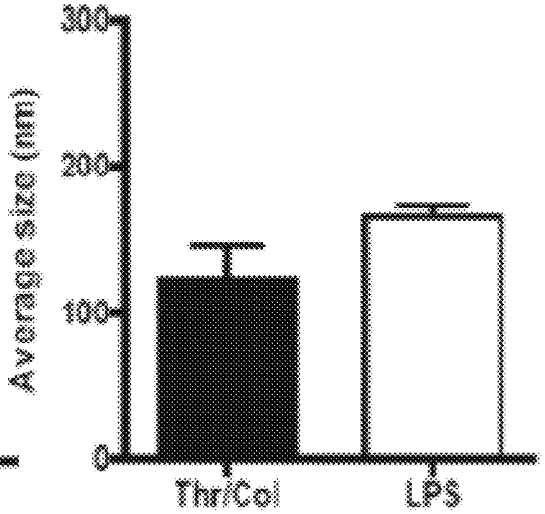
Figure 6G:
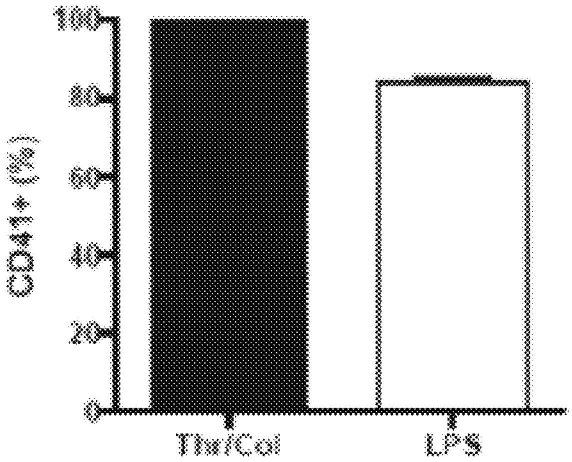
Figure 6H:
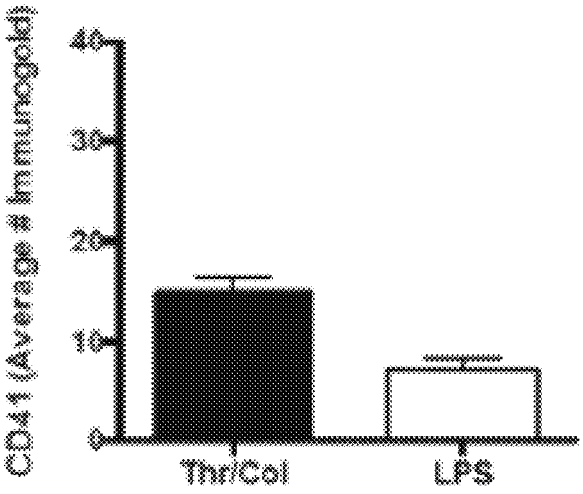

MkEVs were collected or generated from megakaryocytes and platelets, respectively, and characterized using nanoparticle tracking analysis in conjunction with immunogold labelling and electron microscopy to quantify CD41+ expression. Human CD34+-derived megakaryocytes produced between 500-1500 MkEVs per megakaryocyte (FIG. 6A), which was partway between murine bone marrow and fetal liver cell culture controls, with a similar average size of ~200 nm/MkEV (FIG. 6B). While the percentage of CD41+ MkEVs from human CD34+-derived megakaryocyte cultures were comparable to murine bone marrow-derived MkEVs, human MkEVs had more CD41-bound gold particles by immunogold electron microscopy (FIGS. 6C-6D). Human platelets activated with traditional agonists (thrombin and collagen) and inflammatory stimuli (LPS, to mimic an in vivo model) generated a similar number of EVs/platelet (FIG. 6E) and were larger in size than MkEVs (FIG. 6F) (for FIGS. 6A-6F see French et al., Blood Advances, 4:3011-3023 (2020), which is incorporated by reference herein in its entirety). Platelet-derived EVs may also contain mitochondria and other organelles (unlike MkEVs) due to their larger size. The percentage of CD41+ PEVs, and relative expression of CD41-bound gold particles by PEVs were compared to human MkEVs, and murine MkEV controls (FIGS. 6G-6H).

Figure 7A:
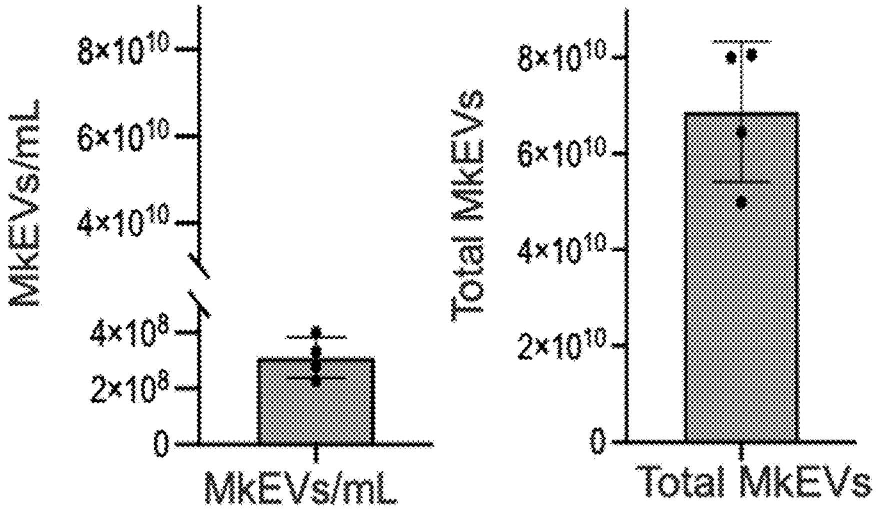
FIGS. 7A-7B show minimal inter-batch variability in MkEV yield as indicated by average MkEVS/mL (FIG. 7A, left) and total MkEV yield (FIG. 7A, right). In addition, MkEV surface marker expression was similar between batches (FIG. 7B)
Figure 7B:
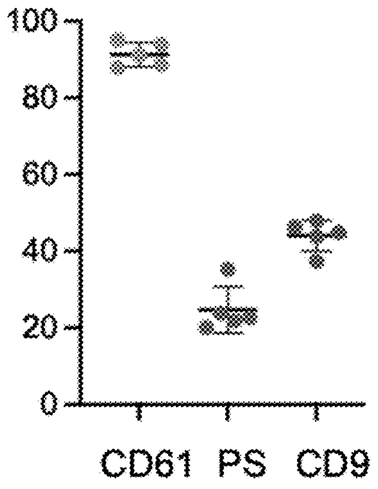

To evaluate inter-batch consistency, MkEVs were collected or generated from megakaryocytes and characterized using flow cytometry to quantify CD41+ expression. There was minimal inter-batch variability in total number of MkEVs/mL and total MkEVs produced per batch (FIG. 7A) and surface marker expression on manufactured MkEVs (FIG. 7B).

Example 4: Define Gene Loading for MkEVs

These examples describe data related to successful loading of diverse cargo into MkEVs.

Figure 11A:
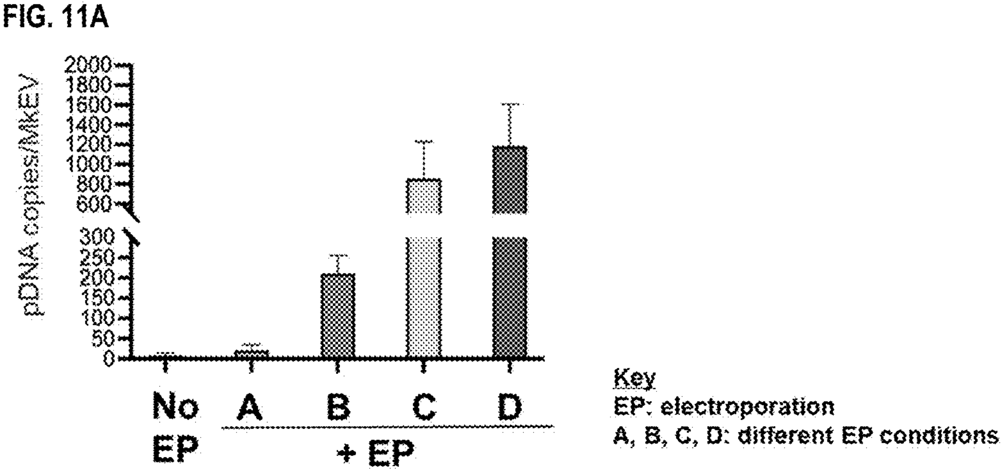
FIGS. 11A-11B show experimental data demonstrating successful loading of FANCA-encoding pDNA (FIG. 11A) and Cas9 (FIG. 11B) into MkEVs.

In one example, a 9.8 kb pDNA encoding wildtype human FANCA was electroporated (EP) into MkEVs. Different electroporation conditions allowed for reproducible titration of cargo loading. In order to quantify only the pDNA copies that were successfully internalized and therefore protected within the MkEV, MkEVs were treated with DNase following electroporation in order to remove any free and EV-associated cargo. The protected, internalized pDNA cargo was then extracted and quantified by qPCR. The amount of loaded pDNA in nanograms (ng) was calculated based on a standard curve run in parallel, and number of pDNA copies/MkEV was calculated. As shown in FIG. 11A, reproducibly titrated amounts of pDNA were loaded into the MkEVs, from as few as 10 copies of pDNA to >1000 copies of pDNA dependent on the electroporation condition.

Figure 11B:
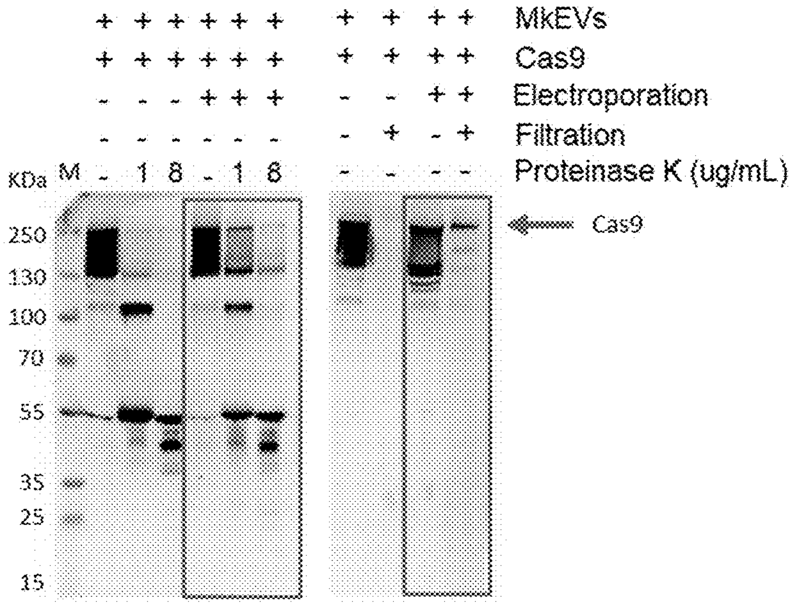

In another example, Cas9 was loaded into MkEVs. MkEVs were electroporated with Cas9, and either treated with proteinase K to remove any un-internalized cargo (free cargo and vesicle surface-associated cargo), or treated with filtration to remove any free cargo, and then analyzed by western blotting for quantification of Cas9. Controls included MkEVs plus Cas9 without electroporation±Proteinase K±filtration. Cas9 was present in electroporated MkEVs, but not in control un-electroporated MkEVs, following filtration, indicating the successful vesicle association and/or internalization of protein cargo. Similarly, Cas9 was present in electroporated MkEVs, but not in control un-electroporated MkEVs following proteinase K digestion indicating both successful internalization and protection of loaded protein cargo following electroporation (FIG. 11B).

In a non-limiting example, to define gene loading efficiency, ~500 bp, 3,000 bp, and 6,000 bp plasmid DNA are conjugated to a Cy5 fluorescent label using the Label IT Tracker Cy5 (Mirus); 4-10 label molecules per plasmid, as previously described. MkEVs re electroporated with Cy5+ labeled DNA at a ratio of $250\times10^3$ (DNA/MV) in 100 μL (15 min, 37 C) using a MaxCyte VLX—a scalable cGMP compliant electroporation system that can transfect up to 200 billion cells per batch for commercial manufacturing. MkEVs are washed to ameliorate nucleic acid of MkEV aggregation and incubated on ice for 20 min to recover, and subsequently centrifuged to remove large aggregates generated during electroporation. MkEVs are washed in PBS and resuspended in co-culture medium for transfection studies. To define pDNA copy number, pDNA are purified from loaded MkEVs using the QIAprep Spin Miniprep Kit (Qiagen), and its concentration is quantified using the Qubit dsDNA HS Assay Kit (Invitrogen).

$$\text{Loading efficiency (\%)} = Cy5 + MV\#/\text{Total } MV\#$$

$$pDNA \text{ copy\#} = \left[\text{Loaded } pDNA\ (ng) * 10\^{}9/\text{Molecular Weight}\right] * \text{Avogadro's Number}$$

Cy5 refers to the number of Cy5-positive megakaryocyte vesicles; MV # refers to the number of megakaryocyte vesicles; Loaded pDNA refers to the amount of pDNA loaded into the MVs; Molecular Weight refers to the molecular weight of the pDNA.

pDNA copy number is confirmed by quantitative PCR amplification of portion of plasmid DNA and amplicons visualized by gel electrophoresis. To define in vitro transfection efficiency MkEVs are co-cultured with CD34+ HSCs at a ratio of 25, 50, 100 MkEVs per HSC and centrifuged at 600×g for 30 min at 37° C., using previously described methods (Kao and Papoutsakis, Science Advances 4:1-11 (2018), which is incorporated by reference herein in its entirety). The percentage of Cy5+ HSCs is quantified at 24, 48, and 72 hours by flow cytometry. To define nuclear transfection efficiency nuclei are isolated for HSCs at 24 hrs as previously described, and the percent of Cy5+ nuclei quantified by flow cytometry.

Loading efficiencies per MkEV are expected to be proportionate to pDNA size; and ~50-60% transfection efficiencies. Loading efficiency and capacity of DNA in EVs are expected to be dependent on DNA size, with linear DNA molecules less than 1000 bp in length being more efficiently associated with MkEVs compared to larger linear DNAs and plasmid DNAs using this approach. If pDNA loading efficiencies are limiting, these studies are repeated with linear DNA and results compared to historical studies in other MkEVs. Other non-limiting methods for loading genetic material into MkEVs include sonication, saponin permeabilization, hypotonic dialysis, cholesterol conjugation, and megakaryocyte microinjection/transfection. Transfection efficiency studies inform in vivo dosing strategy.

Example 5: Biodistribution Data Related to MkEVs

This example provides data related to biodistribution data of MkEVs, including delivery of cargo-loaded MkEVs, targeting of MkEVs ex vivo, and in vivo MkEV biodistribution data.

Confocal microscopy was performed to determine the internalization of MkEV-delivered cargo by primary HSPCs. First, bone marrow was harvested from wild type mice and subjected to red cell lysis using $NH_4Cl$ (STEMCELL Technologies) and lineage depletion (STEMCELL Technologies). HSPCs were isolated by fluorescence-activated cell sorting (FAGS) and defined as Lineage depleted CD150+ CD48− cells. MkEVs were loaded with GFP-tagged Cas9 (Sigma) and guide RNA (Sigma), pre-formed to RNP. HSPCs were cocultured with loaded MkEVs for 18 h. Following the incubation period, unfixed cells were transferred onto a microscope slide and imaged using a Zeiss 780 confocal microscope and a ×63 objective. Zen Black Software was utilized for image capture and processing.

Co-cultures were conducted using primary wild type whole bone marrow cells post red cell lysis using $NH_4Cl$ (STEMCELL Technologies). MkEVs were either loaded with GFP-tagged Cas9 or labelled with DiD Vybrant dye (Invitrogen). DiD labelling was performed according to manufacturer's instructions, followed by 2× wash steps. Loaded or labelled MkEVs were co-cultured with 1e6 whole bone marrow cells for 24 h. Co-cultures were subsequently analysed by flow cytometry (LSR Fortessa X-20, BD Bioscience) using the following antibodies: CD3, CD11b, CD19, GR-1, TER119, CD45R/B220, 7AAD, cKit, Sca-1. Flow cytometry data analysis was conducted using FlowJo (version 10.8.1, BD Bioscience).

Figure 8:
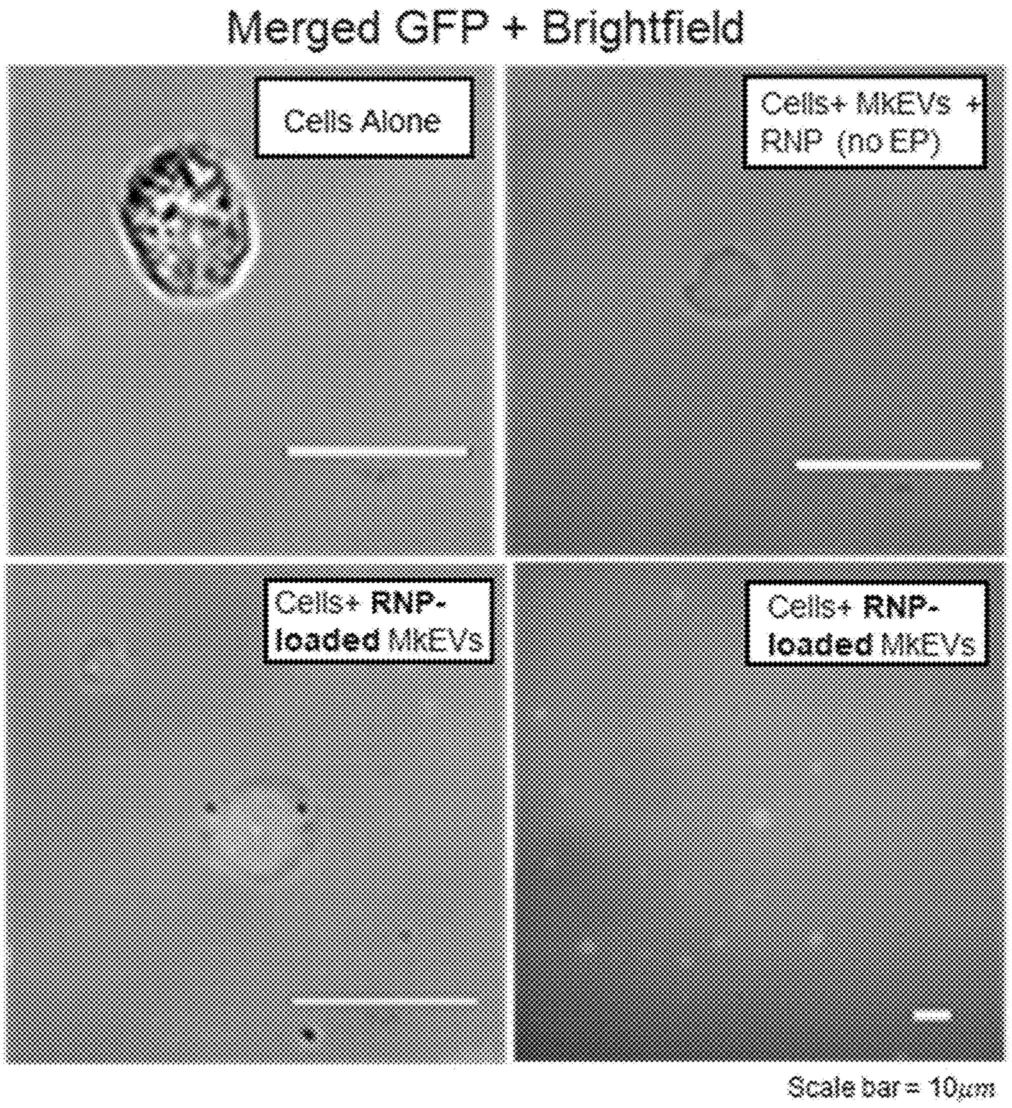
FIG. 8 shows confocal microscopy images of HSPCs (Lineage depleted CD150+CD48− murine bone marrow cells) cocultured with MkEVs loaded with GFP-tagged Cas9 ribonucleoprotein (RNP). Cells cocultured with the cargo-loaded MkEVs were GFP-positive indicating cellular uptake of the GFP-tagged Cas9 loaded MkEVs. In contrast, control samples including cells alone and cells cocultured with MkEVs plus RNP (prior to co-culture with cells, the MKEVs were mixed with RNP but not loaded by electroporation, (no EP)) showed no GFP positivity. These data indicate successful delivery of RNP cargo-loaded MkEVs into HSPCs.

Confocal microscopy images of HSPCs (Lineage depleted CD150+CD48− murine bone marrow cells) cocultured with MkEVs loaded with GFP-tagged Cas9 ribonucleoprotein (RNP) were obtained (FIG. 8). Cells cocultured with the cargo-loaded MkEVs showed GFP-positive cells, indicating cellular uptake of the GFP-tagged Cas9 loaded MkEVs. In contrast, control samples including cells alone and cells cocultured with MkEVs that were mock loaded with RNP (no electroporation (no EP)) showed no GFP positivity. These data indicate successful delivery of RNP cargo-loaded MkEVs into HSPCs.

Figure 9A:
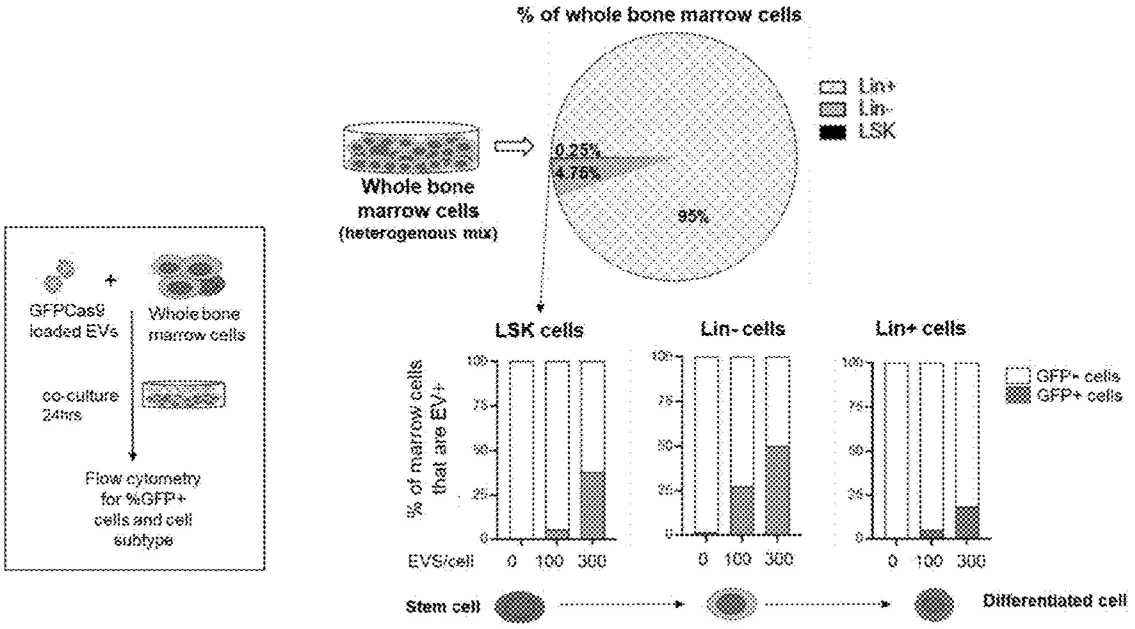
FIGS. 9A-9C show preferential targeting of MkEVs for hematopoietic stem and progenitor cells ex vivo. MkEVs that were loaded with either a GFP-tagged Cas9 protein (FIG. 9A) or labeled with a lipophilic fluorescent dye, DiD (FIG. 9B) were cocultured with primary whole bone marrow derived from wild type mice. Following 24-hours in co-culture, cells were analyzed by flow cytometry for the % of cells that were GFP+ or DID+ (i.e., MkEV+). In addition, the percent of Lineage positive (Lin+), Lineage negative (Lin−), and Lineage negative/c-Kit+/Sca-1+ (LSK) cells were simultaneously determined using fluorescently labeled antibodies against Lineage positive markers, Sca-1, and c-Kit cell surface proteins. The percentage of each subtype of cells in the heterogenous whole bone marrow population is shown in FIG. 9A. For cells cocultured with GFP-tagged Cas9 loaded MkEVs (as shown by the bar graphs in FIG. 9A), despite the vast majority (95%) of the cells in culture being Lin+ cells (differentiated cells), only up to 23% of these cells were positive for MkEVs. In contrast, while <5% were the hematopoietic stem and progenitor cells (Lin− cells), almost 50% of these cells were positive for MkEVs at the 300 EVs per cell dose. Finally, for the rarest and most pluripotent hematopoietic stem cells evaluated in these cultures, the LSK cells, making up only 0.25% of the population, almost 40% of this population were positive for MKEVs. These data indicate the preferential ex vivo targeting of bone marrow-derived hematopoietic stem and progenitor cells. Similarly, as shown in FIG. 9B, for whole bone marrow cells cocultured with DiD-labeled MkEVs; only 20% of Lin+ cells were positive for MkEVs. In contrast, 30% of the rarer population of Lin− cells were positive for MkEVs. Finally, for the rarest and most pluripotent hematopoietic stem cells evaluated in these cultures (LSKs), up to 48% of this population were positive for MKEVs. There were no significant changes in the percentage of total Lin+ and Lin− cells in the whole bone marrow cultures across all the conditions of MkEV co-culture when compared to controls (FIG. 9C).
Figure 9B:
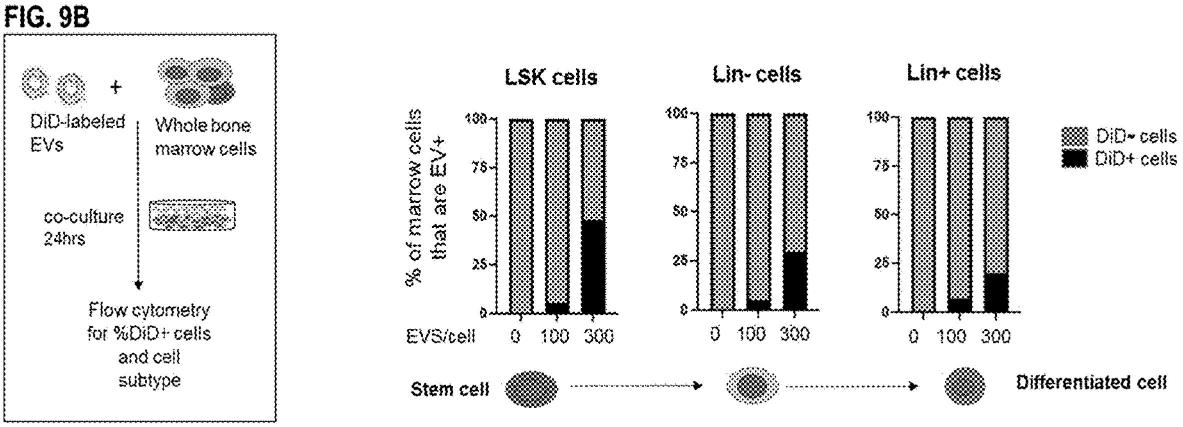
Figure 9C:
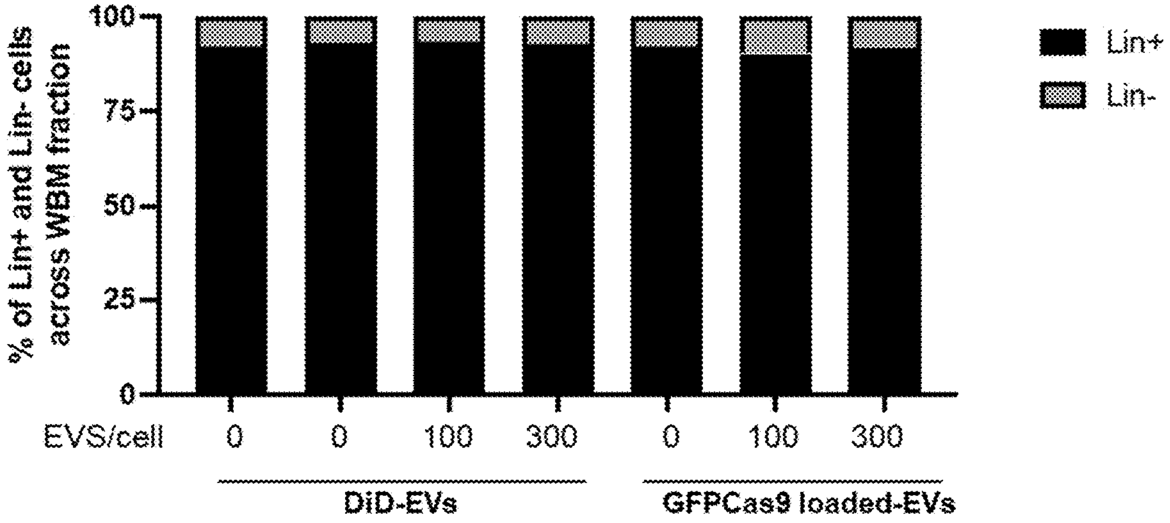

As shown in FIGS. 9A-9C, MkEVs preferentially target hematopoietic stem and progenitor cells ex vivo. MkEVs that were loaded with either a GFP-tagged Cas9 protein (FIG. 9A) or labeled with a lipophilic fluorescent dye, DiD (FIG. 9B). Loaded and DiD-labeled MkEVs were then cocultured with primary whole bone marrow derived from wild type mice. Following 24-hours in co-culture, cells were analyzed by flow cytometry for the % of cells that were GFP+ or DiD+ (i.e., MkEV+). The percent of cells that were GFP+ or DID+, indicating cell uptake/association with MkEVs was quantified by flow cytometry. In addition, the percent of Lineage positive (Lin+), Lineage negative (Lin−), and Lineage negative/c-Kit+/Sca-1+ (LSK) cells were simultaneously determined using fluorescently labelled antibodies against Lineage positive markers, Sca-1, and c-Kit cell surface proteins. The percentage of each subtype of cells in the heterogenous whole bone marrow population is shown in FIG. 9A. For cells cocultured with GFP-tagged Cas9 loaded MkEVs (as shown by the bar graphs in FIG. 9A), despite the vast majority (95%) of the cells in culture being Lin+ cells (differentiated cells), only up to 23% of these cells were positive for MkEVs. In contrast, while <5% were the hematopoietic stem and progenitor cells (Lin− cells), almost 50% of these cells were positive for MkEVs at the 300 EVs per cell dose. Finally, for the rarest and most pluripotent hematopoietic stem cells evaluated in these cultures, the LSK cells, making up only 0.25% of the population, almost 40% of this population were positive for MKEVs. These data indicate the preferential ex vivo targeting of bone marrow-derived hematopoietic stem and progenitor cells. Similarly, as shown in FIG. 9B, for whole bone marrow cells cocultured with DiD-labeled MkEVs; only 20% of Lin+ cells were positive for MkEVs. In contrast, 30% of the rarer population of Lin− cells were positive for MkEVs. Finally, for the rarest and most pluripotent hematopoietic stem cells evaluated in these cultures (LSKs), up to 48% of this population were positive for MKEVs. There were no significant changes in the percentage of total Lin+ and Lin− cells in the whole bone marrow cultures across all the conditions of MkEV co-culture when compared to controls (FIG. 9C), indicating lack of toxicity.

Figure 10A:
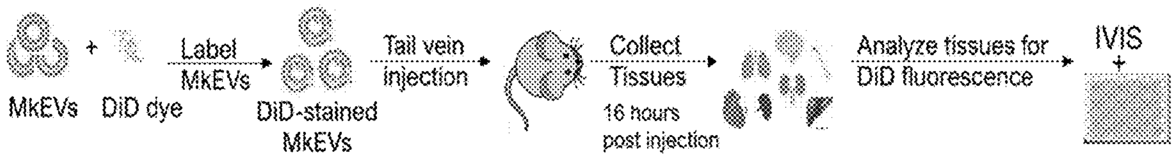
FIGS. 10A-10K show in vivo biodistribution of fluorescently-labeled MkEVs following in vivo delivery to wild type mice. The experimental design is shown in FIG. 10A (n=3-5 mice/group). Fluorescently-labeled MkEVs were injected intravenously via tail vein into wild type mice, and tissues were harvested and analyzed for fluorescence 16 hours post injection.
Figure 10B:
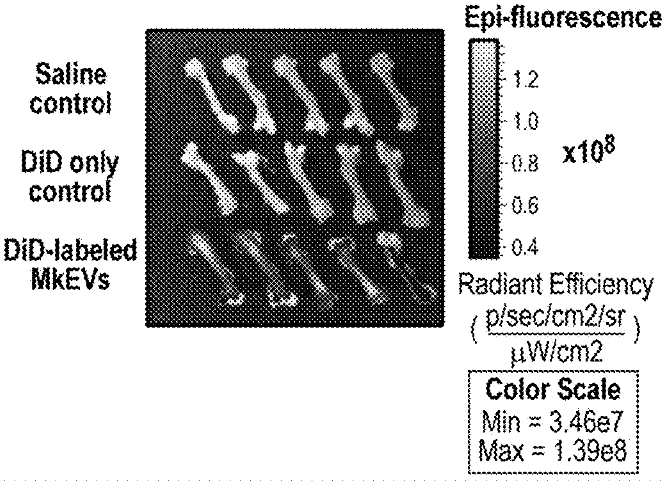
Figure 10C:
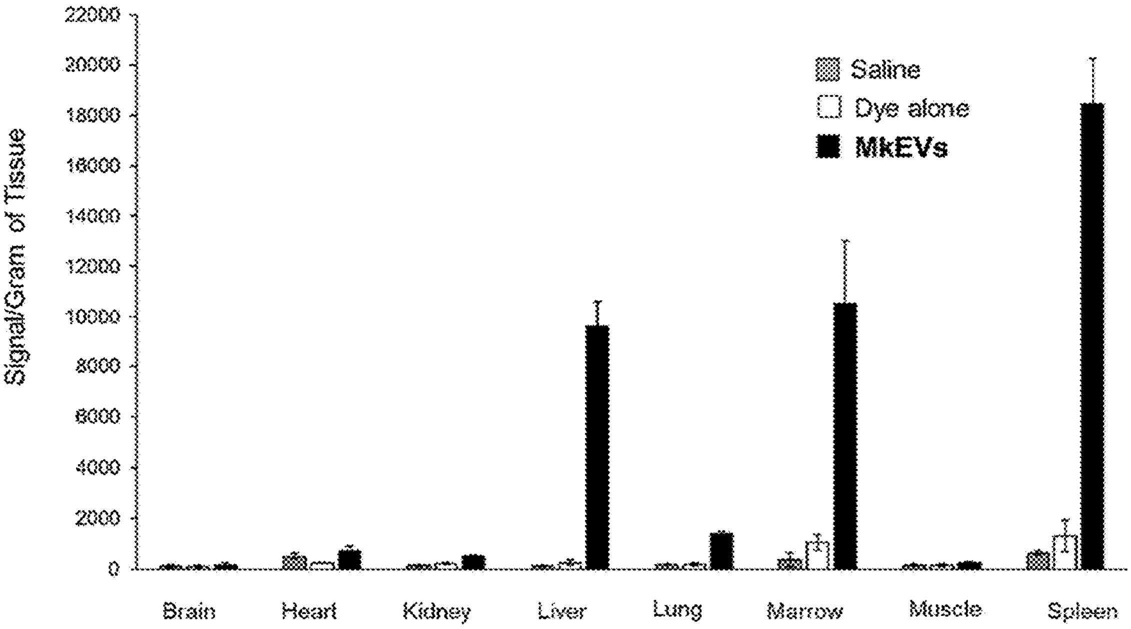
Figure 10D:
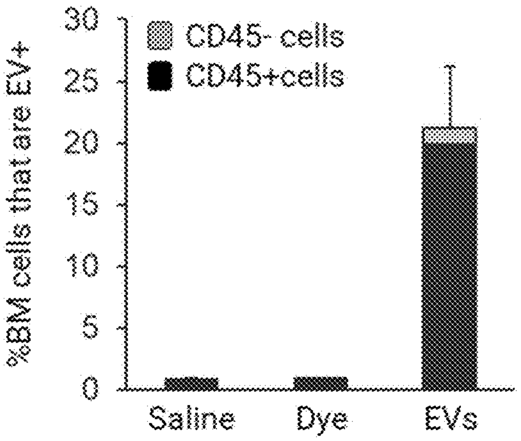
Figure 10E:
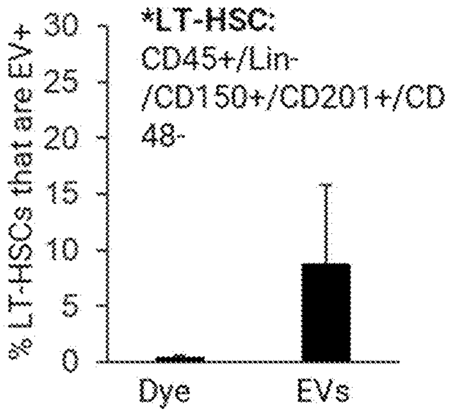
Figure 10F:
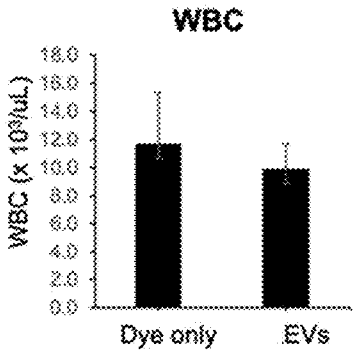
Figure 10G:
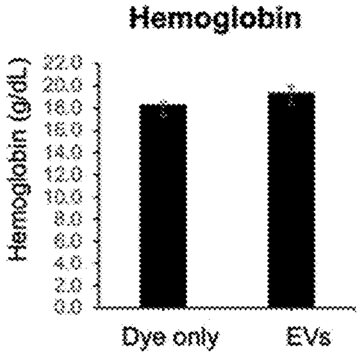
Figure 10H:
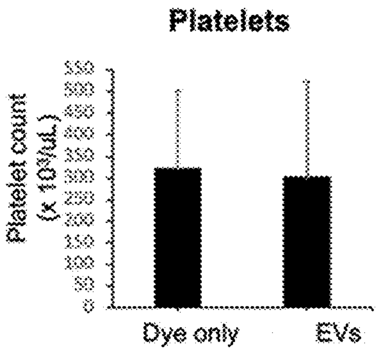
Figure 10I:
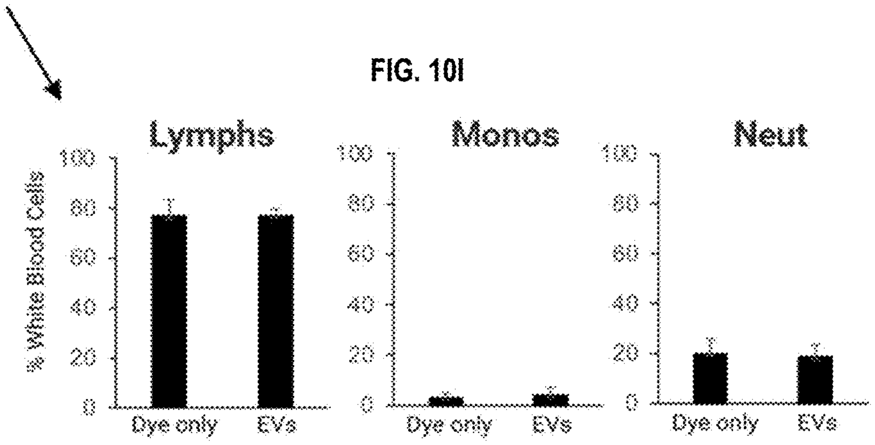
Figure 10J:
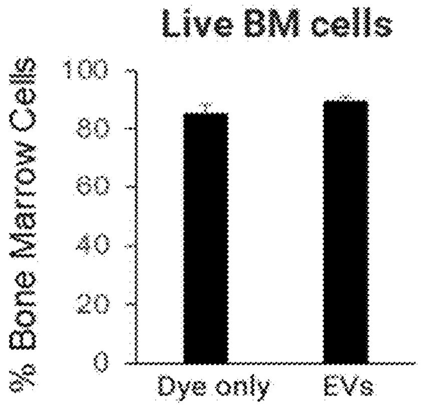
Figure 10K:
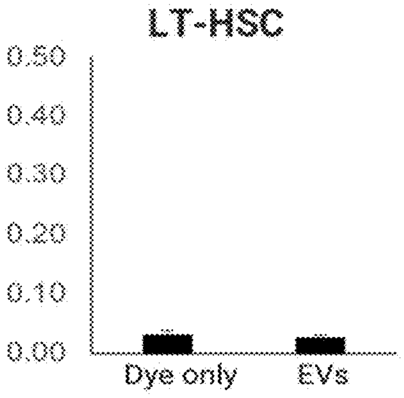

As shown in FIGS. 10A-10K, in vivo biodistribution of fluorescently-labeled MkEVs was examined following in vivo delivery to wild type mice. The experimental design is shown in FIG. 10A (n=3-5 mice/group). Fluorescently-labeled MkEVs were injected intravenously via tail vein into wild type mice, and tissues were harvested and analyzed for fluorescence 16 hours post injection. FIG. 10B shows fluorescent signal detected by IVIS in femurs dissected from mice. N=5 mice/group. Fluorescence in each homogenized tissue, as assayed by plate reader and normalized by tissue weight (FIG. 10C). As shown in FIG. 10C, there was significant in vivo MkEV targeting to the bone marrow following injection. FIGS. 10D and 10E show graphs of experimental data of bone marrow cells stained using antibodies against CD45, Lineage markers, CD150, CD201, and CD48 are analyzed by flow cytometry to determine the % of hematopoietic (CD45+ cells; FIG. 10D) and % of very primitive long-term hematopoietic stem cells (CD45+/Lin−/CD150+/CD201+/CD48− cells; FIG. 10E) that were positive for MkEVs. MkEVs preferentially target the hematopoietic cells within the bone marrow (FIG. 10D) and within that compartment, are targeting the very rare (<0.03% of marrow cells) long-term hematopoietic stem cells (FIG. 10E). There was no evidence of toxicity with regards to the hematopoietic compartment as indicated by lack of change in the peripheral white blood cell count (FIG. 10F), hemoglobin (FIG. 10G), platelet count (FIG. 10H), WBC differential (FIG. 10I), or % of CD45+ and CD45− cells (FIG. 10J), or % of the long-term hematopoietic stem cells in the marrow (FIG. 10K) 16 hours following MkEV injection.

Example 6: Use of Megakaryocyte-Derived Extracellular Vesicles (MkEVs) as a Therapeutic Delivery Vehicle in PA In a non-limiting example, MkEVs were generated by obtaining human primary CD34+ HSCs sourced from peripheral blood. The human primary CD34+ cells were differentiated into megakaryocytes, and the MkEVs were isolated from the megakaryocytes. The MkEVs were loaded with therapeutic cargo. In a non-limiting example, the cargo was plasmid DNA encoding a wild type FANCA protein. The plasmid DNA was loaded into MkEVs using electroporation, and the cargo-loaded MkEVs were injected intravenously into FANCA−/− mice. The injected MkEVs home to bone marrow, deliver their cargo to hematopoietic stem cells and restore FANCA protein expression. Successful gene correction and restoration of FANCA protein expression and function is demonstrated by western blotting, increased mitomycin C resistance, and/or restoration of FAN CD function.

Figure 12A:
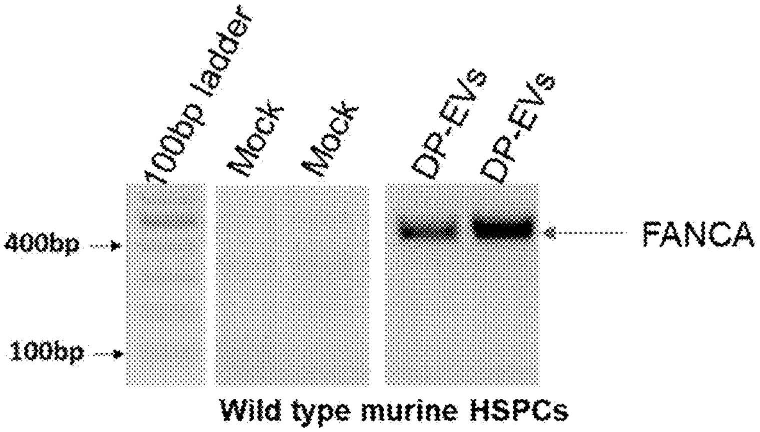
FIGS. 12A-12B show experimental data demonstrating successful delivery of MkEVs loaded with a pDNA encoding wild type FANCA to murine hematopoietic stem and progenitor cells (HSPCs). Murine bone marrow lineage-depleted HSPCs from wild type mice were co-cultured with the MkEVs that were cargo loaded with pDNA encoding the wild type human FANCA (Drug product (DP)-EVs). Following 48 hours in co-culture, human FANCA mRNA (amplicon length 413 bp) was quantified by qPCR.
Figure 12B:
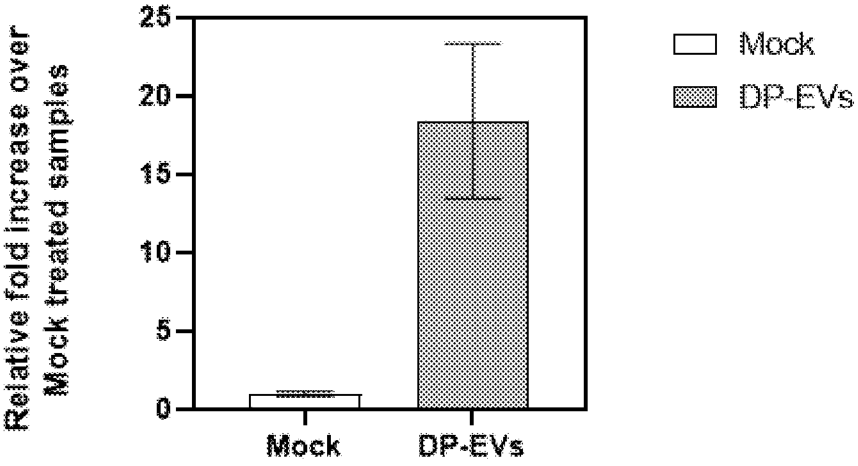
Figure 13A:
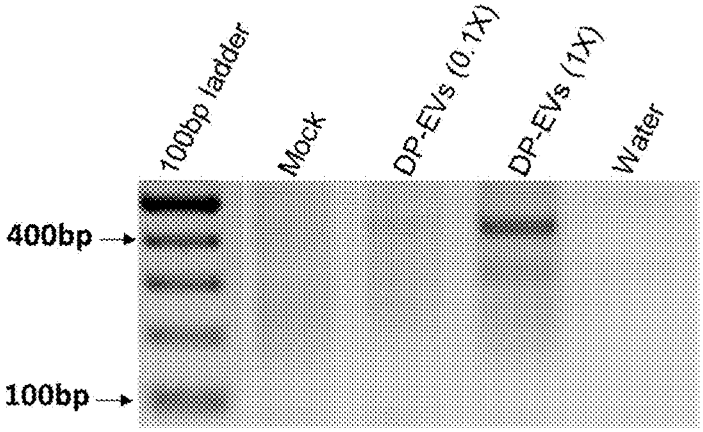
FIGS. 13A-13B show experimental data demonstrating that MkEVs loaded with pDNA encoding the wild type FANCA successfully lead to FANCA mRNA expression in a dose dependent manner. Murine bone marrow lineage depleted cells isolated from wild type mice were co-cultured with the MkEVs that were cargo loaded with pDNA encoding the wild type human FANCA (Drug product (DP)-EVs). Following 48 hours in co-culture, human FANCA mRNA (amplicon length 413 bp) was quantified by qPCR.
Figure 13B:
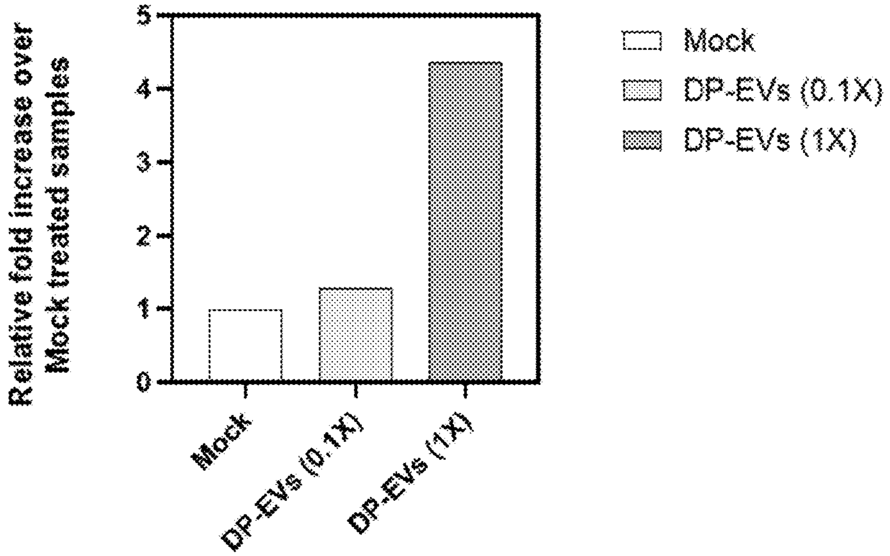

In another non-limiting example, the cargo was a pDNA encoding a wild type human FANCA protein. Murine Lineage-depleted cells were harvested from mouse bone marrow and co-cultured with pDNA-loaded MkEVs (drug product (DP)-EVs). Up to 48 hours following co-culture, total RNA was extracted from the cells and the pDNA-encoded human FANCA mRNA was quantified using qPCR. There was strong expression of human FANCA mRNA in those cells exposed to the cargo-loaded MkEVs (FIG. 12A) while cells treated with the mock-loaded MkEVs (electroporated without cargo) showed no human FANCA expression. Quantification by densitometry indicated this increase was 18.5-fold more mRNA expression in cells treated with the cargo-loaded MkEVs than mock-loaded MkEVs (FIG. 12B). When cells were co-cultured with MkEVs loaded with one tenth the dose of pDNA encoding human FANCA, there was a dose-dependent decrease in the amount of human FANCA mRNA in the co-cultured cells (FIG. 13A). This was confirmed by densitometry readings showing a 1.3 and 4.4× increase in FANCA mRNA expression in the cells treated with low dose and high dose DP-EVs, respectively, when compared to mock-treated cells (FIG. 13B)

Figure 14A:
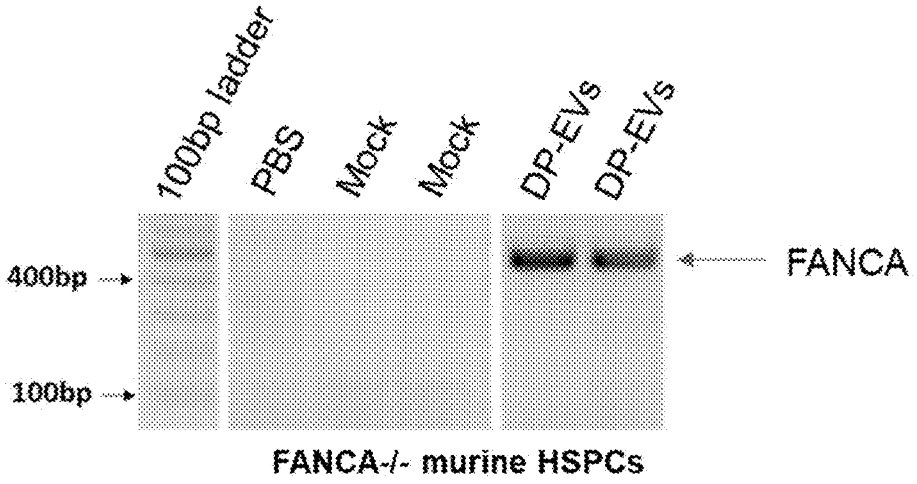
FIGS. 14A-14B show experimental data demonstrating successful restoration of FANCA mRNA expression in FANCA-deficient murine HSPCs. MkEVs loaded with pDNA encoding wild type FANCA restore FANCA mRNA expression in FANCA−/− hematopoietic stem and progenitor cells (HSPCs). Murine bone marrow lineage depleted cells isolated from FANCA−/− mice were co-cultured with the MkEVs that were cargo loaded with pDNA encoding the wild type human FANCA (Drug product (DP)-EVs). Following 48 hours in co-culture, human FANCA mRNA (amplicon length 413 bp) was quantified by qPCR.
Figure 14B:
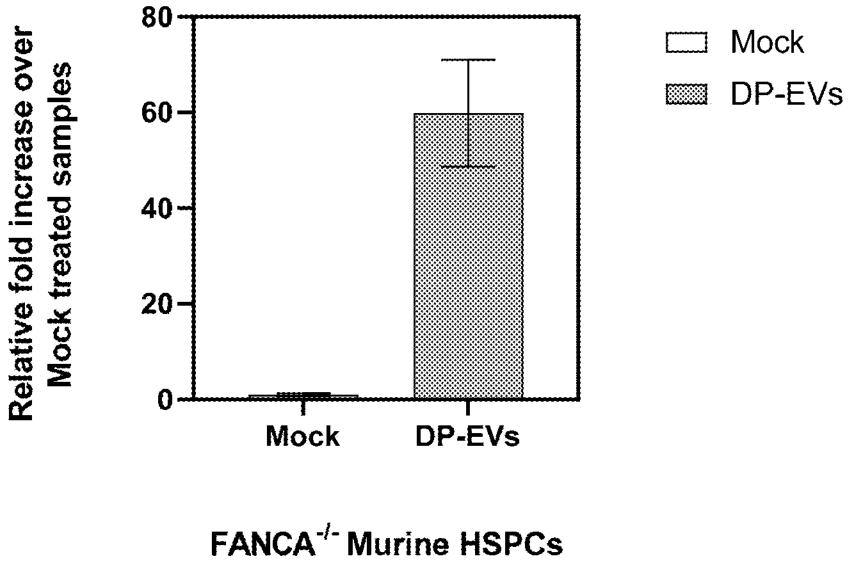

In another non-limiting example, MkEVs loaded with pDNA encoding the wild type human FANCA were co-cultured with murine bone marrow lineage depleted cells isolated from FANCA−/− mice. Following 48 hours in co-culture, human FANCA mRNA (amplicon length 413 bp) was quantified by qPCR. As shown in FIG. 14A, cells devoid of any endogenous FANCA expression showed strong expression of human FANCA from MkEV-mediated delivery of the pDNA when cocultured with the DP-EVs. In contrast, the mock control (cells co-cultured with MkEVs processed in parallel but without an pDNA cargo loaded) showed no FANCA expression. Densitometry readings indicated an 60× increase in FANCA mRNA expression in the cells treated with DP-EVs compared to mock treated cells. (FIG. 14B).

In another non-limiting example, hematopoietic cells are derived from FA patients. Hematopoietic stem and progenitor cells carrying a FA-specific mutation, or primary CD34+ cells from FA-A patients are transfected with the cargo-loaded MkEVs ex vivo. Successful gene correction and restoration of FANCA protein expression and function is demonstrated by qPCR, western blotting, increased mitomycin C resistance, and/or restoration of FAN CD function.

In another non-limiting example, the cargo is a pDNA encoding a wild type FANCA protein. Hematopoietic stem and progenitor cells carrying a FA-specific mutation, or primary CD34+ cells from FA-A patients are transfected with the cargo-loaded MkEVs ex vivo and these MkEV-exposed CD34+ cells are injected intravenously into immunocompromised mice, e.g., Non-obese diabetic (NOD) immunodeficient Cg-Prkdcscid Il2rgtm1Wjl/SzJ mice (NSG) mice. Successful gene correction and restoration of FANCA protein expression and function is demonstrated, for example, by western blotting, increased mitomycin C resistance, and/or restoration of FANCD function, increased engraftment, contribution to peripheral blood, and/or proliferative advantage.

Figure 15:
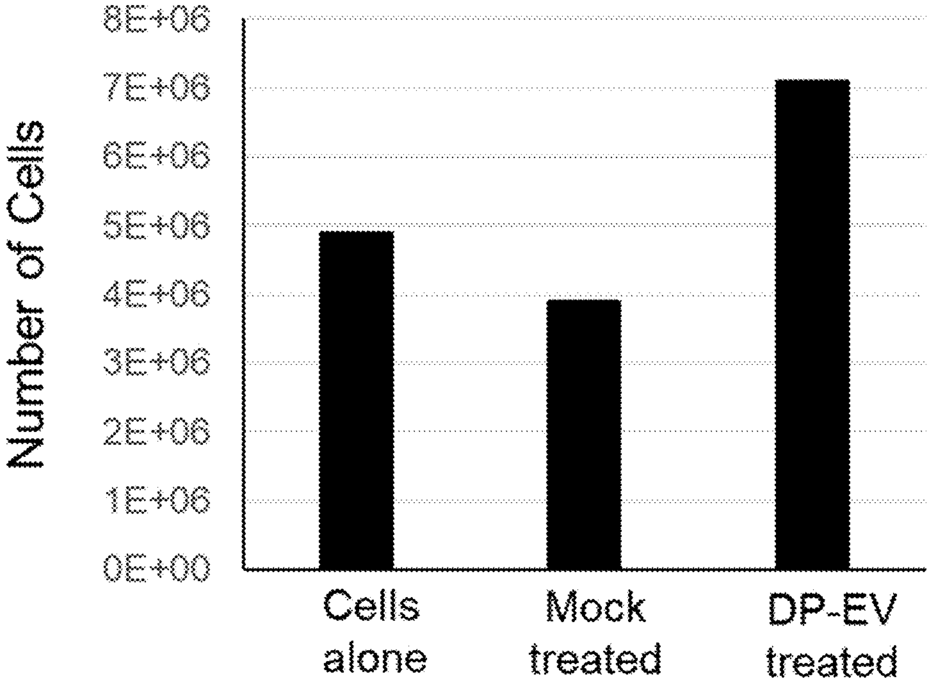
FIG. 15 shows experimental data demonstrating functional benefit in FANCA-deficient cells co-cultured with FANCA-corrective RNP-loaded MkEVs. For these experiments, MkEVs were loaded with a GFP-tagged Cas9 and gRNA targeting a FANCA mutation (drug product (DP)-EVs). This RNP construct can induce therapeutic indels in the mutated FANCA gene. The RNP-loaded EVs (DP-EVs)

In another non-limiting example, the cargo is a gene editing complex comprised of CRISPR/Cas9 and a guide RNA to correct a FANCA mutation. In this example, FA-A patient derived hematopoietic cells were transfected with cargo-loaded MkEVs in vitro. Successful gene editing and restoration of FANCA expression was evidenced by functional gain of proliferative advantage in the transfected cells when compared to untreated cells or cells treated with mock EVs (FIG. 15). This proliferative advantage of cells with restoration of wild type FANCA is a very well-documented phenomenon (Rio, P. et al. *Nat Med* 25, 1396-1401 (2019), Román-Rodriguez, F. J. et al. *Cell Stem Cell* 25, 607-621.e7 (2019), Nicoletti, E. et al. *Ann Hematol* 99, 913-924 (2020), and Rio, P. et al. *Blood* 130, 1535-1542 (2017). In another non-limiting example, hematopoietic stem and progenitor cells carrying a FA-specific mutation, or FA-A patient-derived cells are transfected with the cargo-loaded MkEVs ex vivo. Successful gene editing are determined by functional next generation sequencing and restoration of functional FANCA protein. MkEV-exposed CD34+ cells are then maintained in cell culture and re-assessment for indels by next generation sequencing to reveal a proliferative advantage and normal in vitro differentiation patterns of successfully edited cells.

In another non-limiting example, the cargo is a gene editing complex comprising CRISPR/Cas9 and a guide RNA to correct a FANCA mutation. Hematopoietic stem and progenitor cells carrying a FA-specific mutation, or primary CD34+ cells from FA-A patients are transfected with the cargo-loaded MkEVs ex vivo and these MkEV-exposed CD34+ cells are injected intravenously into immunocompromised mice, e.g., Non-obese diabetic (NOD) immunodeficient Cg-Prkdcscid Il2rgtm1Wjl/SzJ mice (NSG) mice. Indels are measured pre and post engraftment by NGS. Alterations in engraftment and contribution to peripheral blood, and proliferative advantage, and/or resistance to mitomycin C is measured.

In another non-limiting example, the cargo is a gene editing complex comprising CRISPR/Cas9 and a guide RNA to correct a FANCA mutation. Human bone marrow xenograft mouse models are generated with hematopoietic stem and progenitor cells, hematopoitiec stem and progenitor cells carrying a FA-specific mutation, or primary CD34+ cells from FA-A patients. Cargo-loaded MkEVs are injected intravenously into the human bone marrow xenograft mice. The injected MkEVs home to bone marrow, deliver their cargo to hematopoietic stem cells and successfully edit the FANCA gene. Successful gene editing and restoration of FANCA protein expression and function is demonstrated by western blotting, increased mitomycin C resistance, and/or restoration of FANCD function. Indels are measured pre and post engraftment by NGS. Alterations in engraftment and contribution to peripheral blood is measured.

EQUIVALENTS

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties. The publications discussed herein are provided solely for their disclosure prior to the filing date of the present application. Nothing herein is to be construed as an admission that the present disclosure is not entitled to antedate such publication by virtue of prior disclosure.

As used herein, all headings are simply for organization and are not intended to limit the disclosure in any manner. The content of any individual section may be equally applicable to all sections.

What is claimed is:

1. A method for modifying a cell the method comprising:

(a) contacting the cell with a composition comprising a plurality of substantially purified megakaryocyte-derived extracellular vesicles (MkEVs) comprising a lipid bilayer membrane surrounding a lumen, wherein:

the MkEVs lumen comprises a cargo comprising an agent suitable for modifying the cell; and/or, a cargo comprising an agent suitable for modifying the cell is associated with the surface of the MkEVs; and the lipid bilayer membrane comprises two proteins associated with or embedded within, wherein the two proteins are (i) CD31 and (ii) CD47, and (b) modifying the cell to provide a functional Fanconi anemia (FA) related gene and/or to repair a mutated functional FA-related gene therein.

2. The method of claim 1, wherein the lipid bilayer membrane further comprises one or more proteins selected from the group consisting of CD18, CD43, CD11b, CD62P, CD41, CD61, CD21, CD51, CLEC-2, LAMP-1 (CD107a), CD63, CD42b, CD9, CD147, CD32a, CD54, and GPVI;

and/or the lipid bilayer membrane comprises phosphatidylserine.

3. The method of claim 2, wherein:

less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD62P and/or greater than about 40%, or greater than about 50%, or greater than about 60%, or greater than about 70%, or greater than about 80%, or greater than about 90%, or greater than about 95% of the megakaryocyte-derived extracellular vesicles comprise a lipid bilayer membrane comprising CD41 and/or greater than about 40%, or greater than about 50%, or greater than about 60%, or greater than about 70%, or greater than about 80%, or greater than about 90%, or greater than about 95% of the megakaryocyte-derived extracellular vesicles comprise a lipid bilayer membrane comprising CD61 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD147 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD31 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD47 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD32a and/or greater than about 40%, or greater than about 50%, or greater than about 60%, or greater than about 70%, or greater than about 80%, or greater than about 90%, or greater than about 95% of the megakaryocyte-derived extracellular vesicles comprise a lipid bilayer membrane comprising CD9 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD63.

4. The method of claim 1, wherein:

less than about 70%, or less than about 60%, or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising phosphatidylserine (PS) and/or less than about 20%, or less than about 15%, or less than about 10%, or less than about 5% of the megakaryocyte-derived extracellular vesicles comprise a lipid bilayer membrane comprising LAMP-1 (CD107a).

5. The method of claim 1, wherein about 90% or more, or about 95% or more, or about 97% or more, or about 99% or more the megakaryocyte-derived extracellular vesicles are substantially of a diameter in the range between about 100 nm to about 600 nm, between about 30 nm to about 100 nm, or between about 100 nm to about 300 nm.

6. The method of claim 1, wherein the megakaryocyte-derived extracellular vesicles are substantially free of autologous DNA, megakaryocytes, and/or platelets.

7. The method of claim 1, wherein the megakaryocyte-derived extracellular vesicles are suitable for homing to:

a hematopoietic stem cell in vivo and/or in vitro and/or bone marrow in vivo and/or in vitro and/or a lymphatic cell in vivo and/or in vitro and/or a regulatory T cell in vivo and/or in vitro.

8. The method of claim 1, wherein the megakaryocyte-derived extracellular vesicles are derived from a human pluripotent stem cell, or wherein the human pluripotent stem cell is an embryonic stem cell (ESC), or wherein the human pluripotent stem cell is an induced pluripotent stem cell (iPS), or wherein the human pluripotent stem cell is a primary CD34+ hematopoietic stem cell sourced from peripheral blood comprising granulocyte colony-stimulating factor-mobilized adult peripheral blood (mPB) or from cord blood.

9. The method of claim 1, wherein the megakaryocyte-derived extracellular vesicles are isolated from megakaryocytes, which are generated in the absence of added erythropoietin, and/or or in the presence thrombopoietin.

10. The method of claim 1, wherein;

the composition is a pharmaceutical composition further comprising a pharmaceutically acceptable excipient or carrier and/or the cargo is in the lumen and/or the cargo is associated with the surface of the megakaryocyte-derived extracellular vesicles and/or the cargo and/or the agent suitable for modifying the cell comprise(s) one or more therapeutic agents wherein the therapeutic agent is a small molecule therapeutic agent, or a biologic therapeutic agent.

11. The method of claim 10, wherein the therapeutic agent comprises a vaccine, an immunogenic antigen, a nucleic acid therapeutic agent, small molecule therapeutic agent, or a biologic therapeutic agent used for gene therapy, wherein the biologic therapeutic agent encodes a functional protein or a recombinant protein.

12. The method of claim 11, wherein the functional protein or the recombinant protein comprises a wild-type protein, a fusion protein, a cytokine, an antigen, and a peptide, an antibody or an antibody fragment.

13. The method of claim 11, wherein the nucleic acid therapeutic agent expresses a wild-type functional FA gene, and/or comprises a nucleic acid encoding a functional FA-related gene, or a protein product thereof, or a nucleic acid encoding a gene-editing protein capable of creating a functional FA-related gene, or a protein product thereof, or a ribonucleoprotein gene-editing complex capable of creating a functional FA-related gene or a protein product thereof.

14. The method of claim 11, wherein the nucleic acid therapeutic agent is selected from one or more non-autologous and/or recombinant nucleic acid constructs selected from mRNA, tRNA, rRNA, siRNA, microRNA, regulating RNA, non-coding and coding RNA, linear DNA, plasmid DNA, or DNA fragments, and wherein the one or more non-autologous and/or recombinant nucleic acid constructs are incorporated into a vector.

15. The method of claim 14, wherein the vector is an expression vector, a plasmid, a phagemid, a phage derivative, a cosmid, or a viral vector, wherein the expression vector comprises an expression control sequence operatively linked to a nucleotide sequence, wherein the viral vector comprises an adenovirus vector, an adeno-associated virus vector, a poxvirus vector, a retrovirus vector, a lentivirus vector, a sendai virus vector, herpes simplex virus vector, a cytomegalovirus vector, or chimeric viral vectors.

16. The method of claim 11, wherein the nucleic acid therapeutic agent encodes a gene-editing protein, and/or associated elements for gene-editing functionality wherein the gene-editing protein is selected from a zinc finger (ZF), transcription activator-like effector (TALE), meganuclease, and clustered regularly interspaced short palindromic repeat (CRISPR)-associated protein, wherein the CRISPR-associated protein is selected from Cas9, xCas9, Cas12a (Cpf1), Cas13a, Cas14, CasX, CasY, a Class 1 Cas protein, a Class 2 Cas protein, MAD7, and gRNA complexes thereof.

17. The method of claim 10, wherein the therapeutic agent comprises a FA-related gene or a fragment thereof comprising FANCA, FANCB, FANCC, FANCD1 (BRCA2), FANCD2, FANCE, FANCF, FANCG, FANCI, FANCJ (BRIP1), FANCL, FANCM, FANCN (PALB2), FANCO (RAD51C), FANCP (SLX4), FANCQ (ERCC4), FANCR (Rad51), FANCS (BRCA1), FANCT (UBE2T), FANCU (XRCC2), FANCV (REV7) and FANCW (RFWD3).

18. The method of claim 10, wherein the therapeutic agent increases or restores the FA-related gene expression and/or levels and/or function of one or more FA-related proteins, wherein the FA-related proteins comprise FANCA, FANCB, FANCC, FANCD1 (BRCA2), FANCD2, FANCE, FANCE, FANCG, FANCI, FANCJ (BRIP1), FANCL, FANCM, FANCN (PALB2), FANCO (RAD51C), FANCP (SLX4), FANCQ ERCC4), FANCR (Rad51), FANCS (BRCA1), FANCT (UBE2T), FANCU (XRCC2), FANCV (REV7) and FANCW (RFWD3).

19. A method for treating Fanconi anemia (FA), the method comprising:

(a) obtaining a plurality of substantially purified megakaryocyte-derived extracellular vesicles;

(b) incubating the plurality of substantially purified megakaryocyte-derived extracellular vesicles with a therapeutic agent to allow the therapeutic agent to populate the lumen of the megakaryocyte-derived extracellular vesicle and/or associate with the surface of the megakaryocyte-derived extracellular vesicle and yield a deliverable therapeutic agent, wherein the therapeutic agent is capable of treating FA; and (c) administering the deliverable therapeutic agent to a patient or contacting the deliverable therapeutic agent with a biological cell in vitro and administering the contacted biological cell to a patient, wherein the megakaryocyte-derived extracellular vesicles are substantially purified and comprise a lipid bilayer membrane surrounding a lumen, the megakaryocyte-derived extracellular vesicle lumen comprises the therapeutic agent and/or is associated with the surface of the megakaryocyte-derived extracellular vesicle; and the lipid bilayer membrane comprises two proteins associated with or embedded within, wherein the two proteins are (i) CD31 and (ii) CD47.

20. A method for treating Fanconi anemia (FA), the method comprising:

a. obtaining a plurality of substantially purified megakaryocyte-derived extracellular vesicles; the megakaryocyte-derived extracellular vesicles comprising a lipid bilayer membrane surrounding a lumen, wherein:

the lipid bilayer membrane comprises two proteins associated with or embedded within, wherein the two proteins are (i) CD31 and (ii) CD47;

b. incubating the plurality of substantially purified megakaryocyte-derived extracellular vesicles with a therapeutic agent to allow the therapeutic agent to populate the lumen of the megakaryocyte-derived extracellular vesicle and/or associate with the surface of the megakaryocyte-derived extracellular vesicle and yield a deliverable therapeutic agent, wherein the therapeutic agent is capable of increasing or restoring the FA-related gene expression and/or levels and/or function of one or more FA-related proteins; and, c. administering the deliverable therapeutic agent to a patient or contacting the deliverable therapeutic agent with a biological cell in vitro and administering the contacted biological cell to a patient, thereby restoring or increasing FA-related gene expression in the patient to reach a normal level of a patient not afflicted with FA.

* * * * *